United States Patent
Liao et al.

(10) Patent No.: US 10,326,087 B2
(45) Date of Patent: Jun. 18, 2019

(54) COMPOUND AND ORGANIC ELECTRONIC DEVICE COMPRISING THE SAME

(71) Applicant: Nichem Fine Technology Co., Ltd., Jhubei, Hsinchu County (TW)

(72) Inventors: Liang-Di Liao, Jhubei (TW); Shwu-Ju Shieh, Jhubei (TW); Chi-Chung Chen, Jhubei (TW)

(73) Assignee: Nichem Fine Technology Co., Ltd., Jhubei, Hsinchu County (TW)

( * ) Notice: Subject to any disclaimer, the term of this patent is extended or adjusted under 35 U.S.C. 154(b) by 217 days.

(21) Appl. No.: 15/416,616

(22) Filed: Jan. 26, 2017

(65) Prior Publication Data
US 2017/0213972 A1    Jul. 27, 2017

Related U.S. Application Data

(60) Provisional application No. 62/287,724, filed on Jan. 27, 2016.

(51) Int. Cl.
*H01L 51/50* (2006.01)
*H01L 51/00* (2006.01)
(Continued)

(52) U.S. Cl.
CPC ........ *H01L 51/0085* (2013.01); *C07C 211/61* (2013.01); *C07C 255/51* (2013.01);
(Continued)

(58) Field of Classification Search
None
See application file for complete search history.

(56) References Cited

FOREIGN PATENT DOCUMENTS

| CN | 103833507 | * 12/2013 | ............ C09K 11/06 |
|----|-----------|-----------|--------------------------|
| CN | 103833507 | 6/2014 | |
| CN | 103833507 A † | 6/2014 | |
| CN | 103936720 | 7/2014 | |
| CN | 103936720 A † | 7/2014 | |

(Continued)

OTHER PUBLICATIONS

Evidence-10: Supporting Information for: Switching of Non-Helical Overcrowded Heptafulvalene Derivatives, pp. 1-59, by Jiye Luo et al., Publication Date: 2011, which is 1H NMR spectrum (p. 30) in Supporting Information from Evidence-9. Pages/Lines Cited: p. 30.†

(Continued)

*Primary Examiner* — Gregory D Clark
(74) *Attorney, Agent, or Firm* — Muncy, Geissler, Olds & Lowe, P.C.

(57) ABSTRACT

A novel compound is disclosed, which is represented by the following Formula (I):

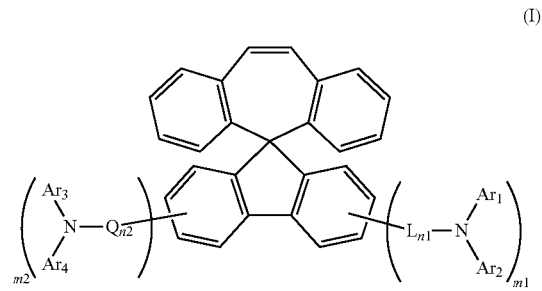

(I)

wherein $Ar_1$, $Ar_2$, $Ar_3$, $Ar_4$, L, Q, n1, n2, m1, and m2 represent the same as defined in the specification. In addition, an organic electronic device is also disclosed, and an organic layer therein comprises the novel compound of the present invention.

11 Claims, 16 Drawing Sheets

(51) Int. Cl.

| | | |
|---|---|---|
| *C07F 15/00* | (2006.01) | |
| *C09K 11/06* | (2006.01) | |
| *C07C 255/51* | (2006.01) | |
| *C07D 213/06* | (2006.01) | |
| *C07D 213/22* | (2006.01) | |
| *C07D 213/57* | (2006.01) | |
| *C07D 235/18* | (2006.01) | |
| *C07D 239/26* | (2006.01) | |
| *C07D 239/74* | (2006.01) | |
| *C07D 251/24* | (2006.01) | |
| *C07C 211/61* | (2006.01) | |
| *C07D 223/14* | (2006.01) | |
| *C07D 307/91* | (2006.01) | |
| *C07D 313/06* | (2006.01) | |
| *C07D 213/38* | (2006.01) | |
| *H01L 51/42* | (2006.01) | |

(52) U.S. Cl.
CPC ......... *C07D 213/06* (2013.01); *C07D 213/22* (2013.01); *C07D 213/38* (2013.01); *C07D 213/57* (2013.01); *C07D 223/14* (2013.01); *C07D 235/18* (2013.01); *C07D 239/26* (2013.01); *C07D 239/74* (2013.01); *C07D 251/24* (2013.01); *C07D 307/91* (2013.01); *C07D 313/06* (2013.01); *C07F 15/0033* (2013.01); *C09K 11/06* (2013.01); *H01L 51/006* (2013.01); *H01L 51/0056* (2013.01); *H01L 51/0057* (2013.01); *H01L 51/0061* (2013.01); *H01L 51/0067* (2013.01); *H01L 51/0072* (2013.01); *H01L 51/5016* (2013.01); *C07C 2603/18* (2017.05); *C07C 2603/98* (2017.05); *C07C 2603/99* (2017.05); *C09K 2211/1007* (2013.01); *C09K 2211/1029* (2013.01); *C09K 2211/1033* (2013.01); *C09K 2211/185* (2013.01); *H01L 51/0058* (2013.01); *H01L 51/0073* (2013.01); *H01L 51/42* (2013.01); *H01L 51/5056* (2013.01); *H01L 51/5072* (2013.01); *H01L 51/5088* (2013.01); *H01L 51/5096* (2013.01); *Y02E 10/549* (2013.01)

(56) References Cited

FOREIGN PATENT DOCUMENTS

| CN | 106432107 A | † | 2/2017 | |
| --- | --- | --- | --- | --- |
| KR | 10-2011-0041730 | * | 4/2011 | ............ C09K 11/06 |
| KR | 1020110041730 A | † | 4/2011 | |
| KR | 10-2012-0048125 | * | 2/2012 | ............ C09K 11/06 |
| KR | 10-2012-0047038 | | 5/2012 | |
| KR | 10-2012-0048125 | | 5/2012 | |
| KR | 10-2013-0110347 | | 10/2013 | |
| KR | 10-2013-0140303 | | 12/2013 | |
| KR | 1020130110347 A | † | 10/2014 | |

OTHER PUBLICATIONS

Evidence-9: Switching of non-helical overcrowded tetrabenzoheptafulvalene derivatives, pp. 2029-2034, by Jiye Luo et al., Chemical Science, Publication Date: Jul. 21, 2011. Pages/Lines Cited: p. 2031 printed on bottom right corner, left col.†

Evidence-8: Doubly Ortho-linked cis-4,4'-Bis(diarylamino)stilbene/ Fluorene Hybrids as Efficient Non-doped, Sky-blue Fluorescent Materials for Optoelectronic Applications, pp. S1-S22, by Yi Wei et al., 2007, which is 1H NMR spectrum (p. S16) in Supporting Information from Evidence-7. Pages/Lines Cited: S16 printed on top right corner.†

Evidence-7: Doubly Ortho-Linked cis-4,4'-Bis(diarylamino)stilbene/ Fluorene Hybrids as Efficient Nondoped, Sky-Blue Fluorescent Materials for Optoelectronic Applications, pp. 7478-7479, by Yi Wei et al., J. Am. Chem. Soc., Publication Date: May 25, 2007. Pages/Lines Cited: p. 7478 printed on bottom left corner, right col.†

Evidence-6: Doubly Ortho-linked Quinoxaline/Diphenylfluorene Hybrids as Bipolar, Fluorescent Chameleons for Optoelectronic Applications, pp. S1-S23, by Chien-Tien Chen et al., Publication Date: 2006, which is 1H NMR spectrum (p. S20) in Supporting Information from Evidence-5. Pages/Lines Cited: S20 printed on top right corner.†

Evidence-5: Doubly Ortho-Linked Quinoxaline/Diphenylfluorene Hybrids as Bipolar, Fluorescent Chameleons for Optoelectronic Applications, pp. 10992-10993, Chien-Tien Chen et al., J. Am. Chem. Soc., Publication Date: Aug. 8, 2006. Pages/Lines Cited: p. 10992 printed on bottom left corner, right col.†

Evidence-4: hint of step 4 "Check that the integration of the peak matches the number of hydrogens in the molecule", webpage of Golden Rules to Nuclear Magnetic Resonance Spectroscopy (NMR) Analysis, 1 page, by Dr. Madalee Gassaway, Publication Date: Oct. 23, 2017 (from http://blog.cambridgecoaching.com/golden-rules-to-nuclear-magnetic-resonance-spectroscopy-nmr-analysis-part-1-0). Pages/Lines Cited: hint of step 4, webpage of Golden Rules to Nuclear Magnetic Resonance Spectroscopy (NMR) Analysis.†

Evidence-3: Real-Time Enzyme Kinetics by Quantitative NMR Spectroscopy and Determination of the Michaelis−Menten Constant Using the Lambert‑W Function, pp. 1943-1948, by Cheenou Her et al., J. Chem. Educ., 2015. Pages/Lines Cited: p. 1946 printed on bottom, right col., lines 13-17.†

Evidence-2: Integration of 1H NMR spectra (proton) from NMR theory of Spectroscopy of Organic Chemistry Lecture Website at University of Colorado Boulder, which was built by Dr. Patty Feist et al. (from < http://www.orchemboulder.com:80/Spectroscopy/ nmrtheory/NMRtutorials.shtml> 1 page, Dec. 14, 2016, retrieved from Internet Wayback Machine < http://web.archive.org/web/ 20161214110543/http://www.orgchemboulder.com:80/Spectroscopy/ nmrtheory/NMRtutorial.shtml> on Feb. 7, 2018); Pages/Lines Cited: lines 2-3 & 4-5.†

Evidence-1: Organic Chemistry (eighth edition), Paula Yurkanis Bruice, Global Edition, pp. 660, 661, 668, 678, Publication Date: Jan. 15, 2016, Pearson Education, Inc., NJ, USA; Pages/Lines Cited: pp. 660, 661, 668, 678.†

Evidence-11: The Synthesis of Novel p-Quinone Methides: O-Dealkylation of 5-(p-Alkyloxyaryl)-10,11-dihydrodibenzo[a,d]cyclohepten-5-ols and Related Compounds, pp. 2607-2619, by Benjamin Taljaard et al., Eur. J. Org. Chem., Publication Date: Dec. 31, 2005. Pages/Lines Cited: p. 2612 printed on bottom left corner, right col.†

Evidence-12: Polycationic Ligands in Gold Catalysis: Synthesis and Applications of Extremely π‑Acidic Catalysts, pp. 18815-18823, by Javier Carreras et al., Journal of the American Chemical Society, Publication Date: Dec. 5, 2013. Pages/Lines Cited: p. 18817 printed on bottom.†

Evidence-13: Supplementary Information—Polycationic ligands in gold catalysis: Synthesis and applications of extremely π;-acidic catalysts, pp. S1-S231, by Javier Carreras et al., Publication Date: 2013, which is 1H NMR spectrum (p. S200) in Supporting Information from Evidence-12. Pages/Lines Cited: S200 printed on bottom right corner.†

Evidence-14: Doubly ortho-linked quinoxaline/triarylamine hybrid as a bifunctional, dipolar electroluminescent template for optoelectronic applications, pp. 3980-3982, Chien-Tien Chen et al., Chem. Commun, Publication Date: Jul. 8, 2005. Pages/Lines Cited: p. 3980 printed on bottom left corner.†

(56) References Cited

OTHER PUBLICATIONS

Evidence-15: Doubly Ortho-linked Quinoxaline/Triarylamine Hybrid as a Bifunctional, Dipolar Electroluminescent Template for Optoelectronic Applications, pp. 1-12, by Chen-Tien Chen et al., Publication Date: 2005, which is 1H NMR spectoscopic data (pp. 5 and 6) in Supporting Information from Evidence-14. Pages/Lines Cited: p. 5 and 6.†

\* cited by examiner
† cited by third party

COMPOUND AND ORGANIC ELECTRONIC DEVICE COMPRISING THE SAME

CROSS REFERENCE TO RELATED APPLICATION

This application claims the benefit of filing date of U. S. Provisional Application Ser. No. 62/287,724, entitled "Novel Compound and Organic Electronic Device Using the Same" filed Jan. 27, 2016 under 35 USC § 119(e)(1).

BACKGROUND

1. Field

The present invention relates to a novel compound and an organic electronic device using the same.

2. Description of Related Art

It is well known that organic light emitting device (OLED device) was initially invented and proposed by Eastman Kodak Company through a vacuum evaporation method. Tang and VanSlyke of Kodak Company deposited an electron transport material such as $Alq_3$ on a transparent indium tin oxide (abbreviated as ITO) glass formed with an organic layer of aromatic diamine thereon, and subsequently completed the fabrication of an organic electroluminescent (EL) device after a metal electrode is vapor-deposited onto the $Alq_3$ layer. The organic EL device currently becomes a new generation lighting device or display because of high brightness, fast response speed, light weight, compactness, true color, no difference in viewing angles, without using any LCD backlight plates, and low power consumption.

Recently, some interlayers such as electron transport layer and hole transport layer are added between the cathode and the anode for increasing the current efficiency and power efficiency of the OLEDs. For example, an organic light emitting diode (OLED) 1' shown as FIG. 1 is designed to consist of: a cathode 11', an electron injection layer 13', a light emitting layer 14', a hole transport layer 16', and an anode 18'.

Recently, for effectively increasing the lighting performance of OLEDs, OLED manufactures and researchers have made great efforts to develop different compounds used as the materials for the OLEDs. However, in spite of various compounds have been developed, the current phosphorescence OLEDs still cannot perform outstanding luminous efficiency and device lifetime. Accordingly, in view of the conventional or commercial materials for OLEDs still including drawbacks, the inventor of the present application has made great efforts to make inventive research thereon and eventually provided novel compounds for OLED.

SUMMARY

The object of the present disclosure is to provide a novel compound and an organic electronic device comprising the same.

According to one or more embodiments, a compound is represented by Formula (I) below:

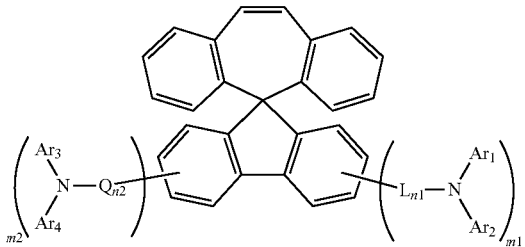

wherein,
$Ar_1$, $Ar_2$, $Ar_3$, and $Ar_4$ are each independently hydrogen, deuterium, a substituted or unsubstituted $C_1$-$C_{20}$alkyl group, a substituted or unsubstituted $C_6$-$C_{40}$aryl group, a substituted or unsubstituted $C_1$-$C_{40}$heterocyclic group, or a substituted or unsubstituted amine group; or $Ar_1$ and $Ar_2$ together with the nitrogen atom to which they are bonded is a substituted or unsubstituted $C_1$-$C_{40}$heterocyclic group; or $Ar_3$ and $Ar_4$ together with the nitrogen atom to which they are bonded is a substituted or unsubstituted $C_1$-$C_{40}$heterocyclic group;
L and Q are each independently a substituted or unsubstituted $C_6$-$C_{40}$arylene group;
n1 and n2 are each independently 0 or 1; and
m1 and m2 are each independently 0, 1 or 2, and with the proviso that m1 and m2 are not 0 at the same time.

According to one or more embodiments, an organic electronic device comprises: a first electrode; a second electrode; and an organic layer disposed between the first electrode and the second electrode, wherein the organic layer comprises the compound of the aforesaid Formula (I).

The present disclosure provides a novel compound. When the compound of the present disclosure is used in an organic electronic device, the efficiency of the organic electronic device can be improved. Especially, when the novel compound of the present disclosure is used as one material of an organic light emitting device, the luminous efficiency of the organic light emitting device can further be improved.

DETAILED DESCRIPTION

Figure 1:
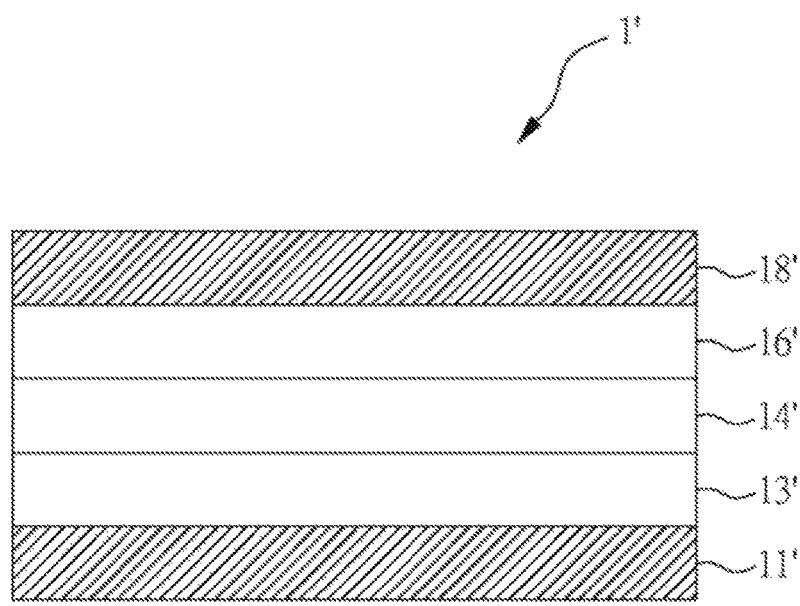
FIG. 1 is a perspective view showing an OLED device of the prior art.

Hereinafter, the present disclosure is described in detail. The present disclosure has been described in an illustrative manner, and it is to be understood that the terminology used is intended to be in the nature of description rather than of limitation. Many modifications and variations of the present disclosure are possible in light of the teachings. Therefore, it is to be understood that within the scope of the appended claims, the invention may be practiced otherwise than as specifically described.

Compound

A compound according to one exemplary embodiment may be represented by the following Formula (I).

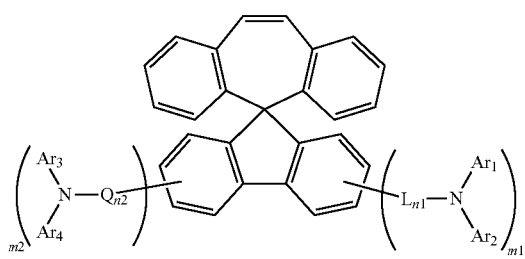

(I)

In formula (I), $Ar_1$, $Ar_2$, $Ar_3$, and $Ar_4$ may be each independently hydrogen, deuterium, a substituted or unsubstituted $C_1$-$C_{20}$alkyl group, a substituted or unsubstituted $C_6$-$C_{40}$aryl group, a substituted or unsubstituted $C_1$-$C_{40}$heterocyclic group, or a substituted or unsubstituted amine group; or $Ar_1$ and $Ar_2$ together with the nitrogen atom to which they are bonded may be a substituted or unsubstituted $C_1$-$C_{40}$heterocyclic group; or $Ar_3$ and $Ar_4$ together with the nitrogen atom to which they are bonded may be a substituted or unsubstituted $C_1$-$C_{40}$heterocyclic group;

L and Q may be each independently a substituted or unsubstituted $C_6$-$C_{40}$arylene group;

n1 and n2 may be each independently 0 or 1; and m1 and m2 may be each independently 0, 1 or 2, and with the proviso that m1 and m2 are not 0 at the same time.

According to one embodiment, $Ar_1$, $Ar_2$, $Ar_3$, and $Ar_4$ can be each independently a substituted or unsubstituted $C_6$-$C_{40}$aryl group, or a substituted or unsubstituted $C_1$-$C_{40}$heterocyclic group; or $Ar_1$ and $Ar_2$ together with the nitrogen atom to which they are bonded can be a substituted or unsubstituted $C_1$-$C_{40}$heterocyclic group; or $Ar_3$ and $Ar_4$ together with the nitrogen atom to which they are bonded can be a substituted or unsubstituted $C_1$-$C_{40}$heterocyclic group. Preferably, $Ar_1$, $Ar_2$, $Ar_3$, and $Ar_4$ are each independently a substituted or unsubstituted $C_6$-$C_{40}$aryl group, or a substituted or unsubstituted $C_1$-$C_{40}$heteroaryl group; or $Ar_1$ and $Ar_2$ together with the nitrogen atom to which they are bonded is a substituted or unsubstituted $C_1$-$C_{40}$heteroaryl group; or $Ar_3$ and $Ar_4$ together with the nitrogen atom to which they are bonded is a substituted or unsubstituted $C_1$-$C_{40}$heteroaryl group.

According to one embodiment, $Ar_1$, $Ar_2$, $Ar_3$, and $Ar_4$ may be each independently substituted or unsubstituted phenyl, substituted or unsubstituted biphenyl, substituted or unsubstituted terphenyl, substituted or unsubstituted fluorenyl, substituted or unsubstituted tribenzyloxepinyl, substituted or unsubstituted dibenzofuranyl, substituted or unsubstituted dibenzothiofuranyl, substituted or unsubstituted naphthyl, or substituted or unsubstituted tribenzyl-azepinyl group. Preferably, $Ar_1$, $Ar_2$, $Ar_3$, and $Ar_4$ are each independently unsubstituted phenyl, phenyl substituted with alkyl, unsubstituted biphenyl, unsubstituted terphenyl, unsubstituted fluorenyl, fluorenyl substituted with alkyl, unsubstituted tribenzyloxepinyl, unsubstituted dibenzofuranyl, or unsubstituted naphthyl.

According to one embodiment, m1 may be 1; and m2 may be 0 or 1. According to another embodiment, m1 may be 1 and m2 may be 0. According to further another embodiment, m1 may be 1 and m2 may be 1.

According to one embodiment, m1 may be 1; m2 may be 0; and $Ar_1$ and $Ar_2$ together with the nitrogen atom to which they are bonded may be a substituted or unsubstituted $C_1$-$C_{40}$heteroaryl group. Preferably, $Ar_1$ and $Ar_2$ together with the nitrogen atom to which they are bonded is unsubstituted tribenzyl-azepinyl group.

According to one embodiment, L and Q may be each independently substituted or unsubstituted phenylene, biphenylene, or naphthylene. Preferably, L and Q are each independently unsubstituted phenylene.

According to one embodiment, when m1 and m2 are not 0 at the same time, $-L_{n1}-NAr_1Ar_2$ and $-Q_{n2}-NAr_3Ar_4$ can be the same.

According to one embodiment, m1 and m2 are 1, and $-L_{n1}-NAr_1Ar_2$ and $-Q_{n2}-NAr_3Ar_4$ can be the same.

According to one embodiment, the compound of Formula (I) can be represented by any one of Formulas (I-1) to (I-9) below.

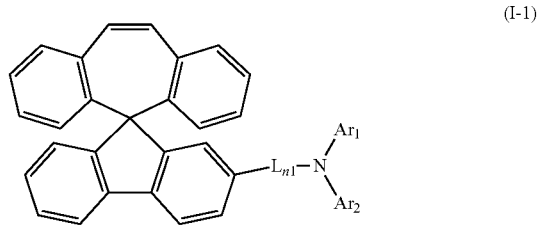

(I-1)

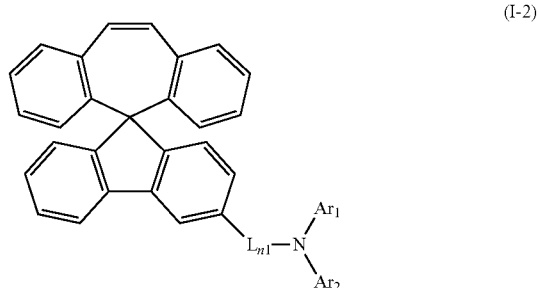

(I-2)

(I-3)
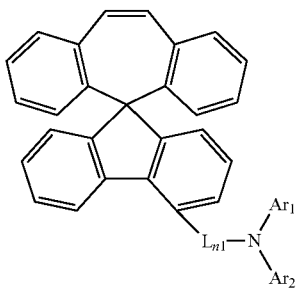
(I-4)
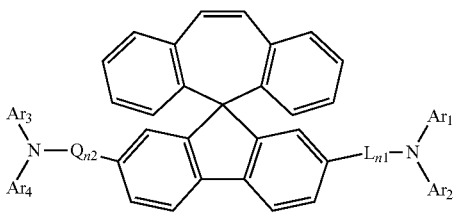
(I-5)
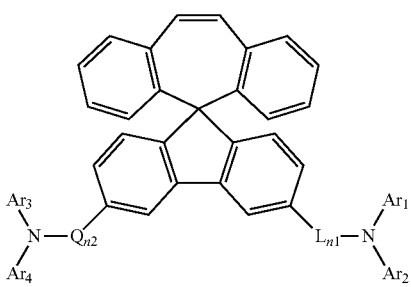
(I-6)
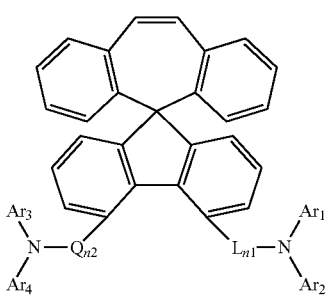
(I-7)
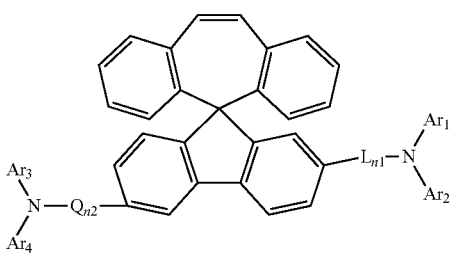
(I-8)
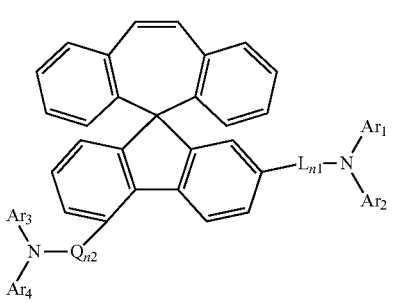
(I-9)
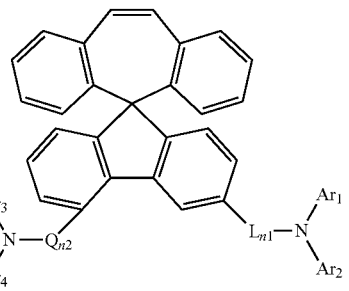
$Ar_1$, $Ar_2$, $Ar_3$, $Ar_4$, L, Q, n1, and n2 in Formulas (I-1) to (I-9) represent the same as those described above.
According to one embodiment, $-L_{n1}$-$NAr_1Ar_2$ and $-Q_{n2}$-$NAr_3Ar_4$ can be each independently selected from the group consisting of:
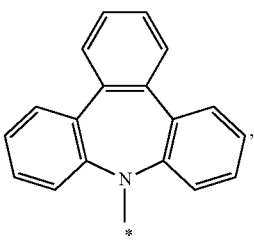
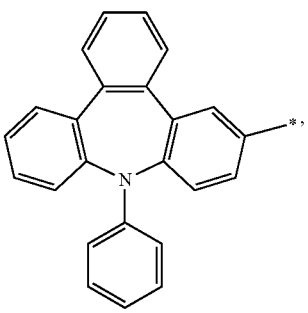
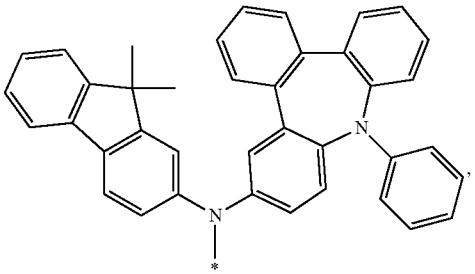
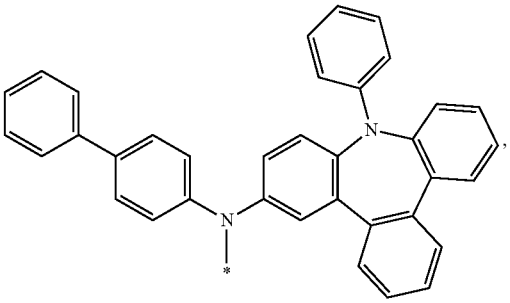

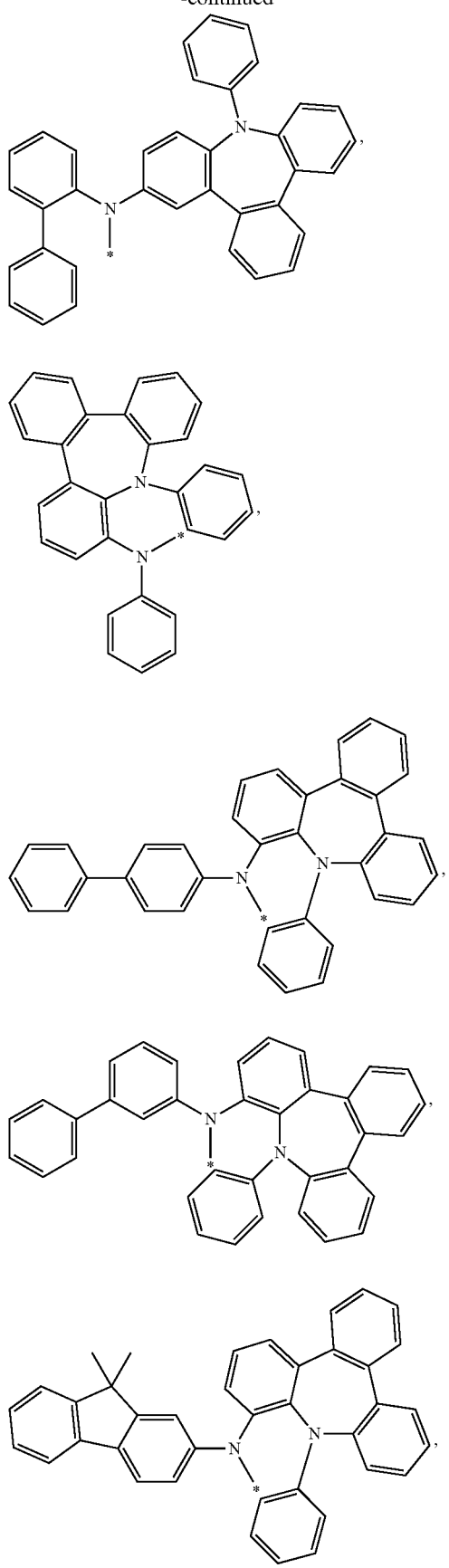
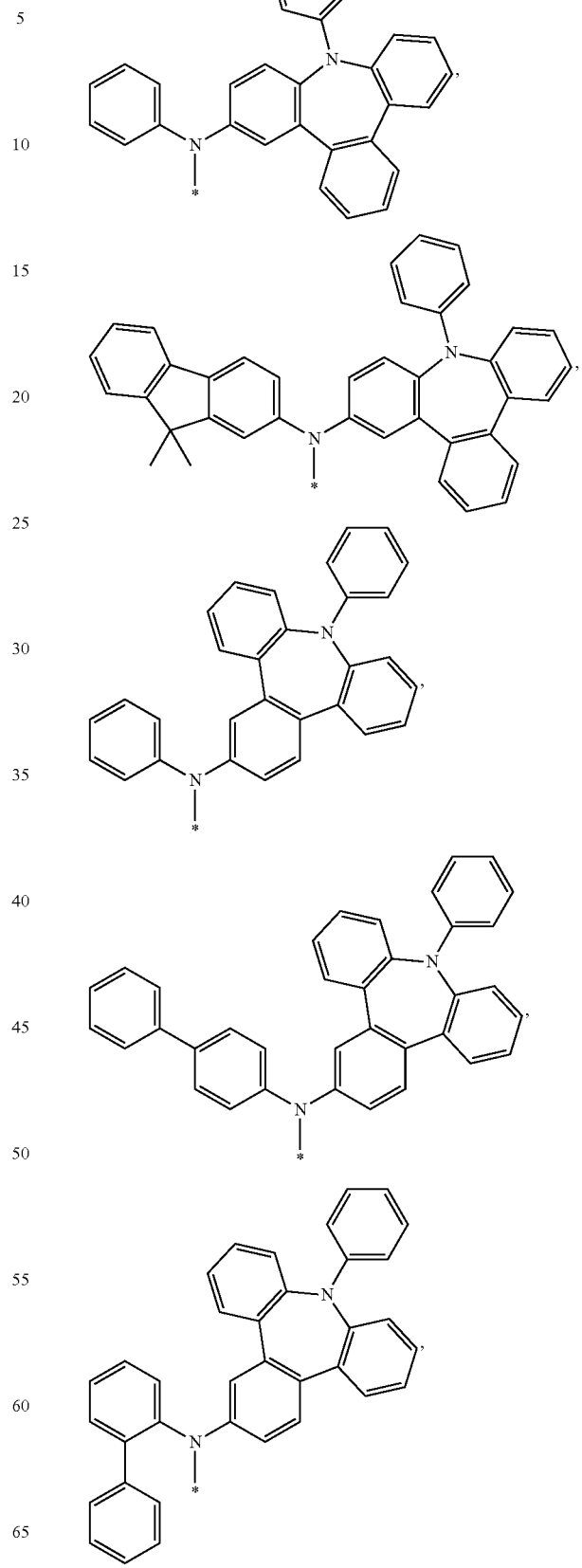

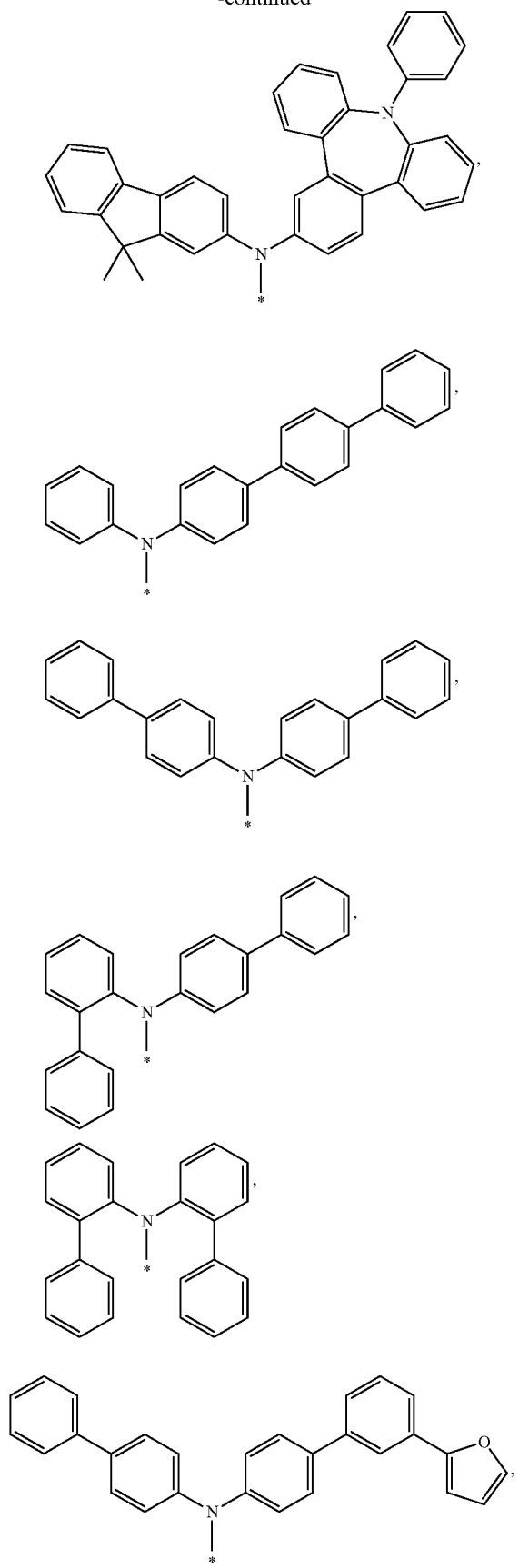

11
-continued
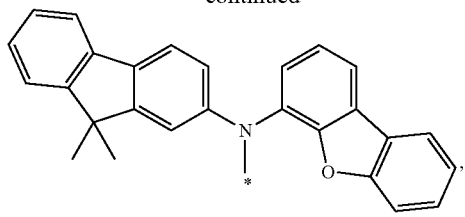
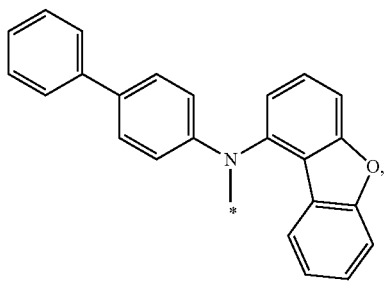
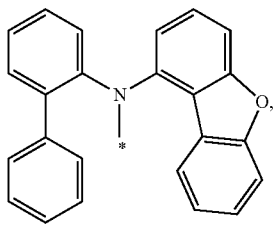
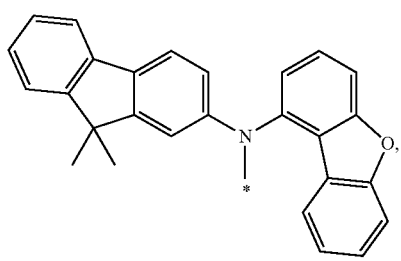
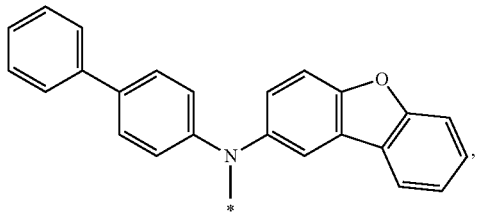
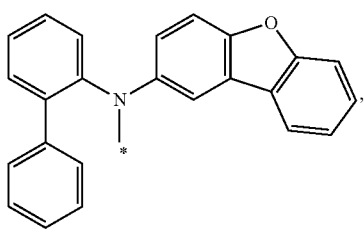
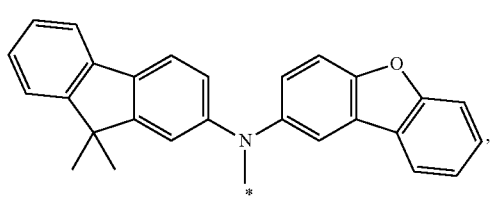
12
-continued
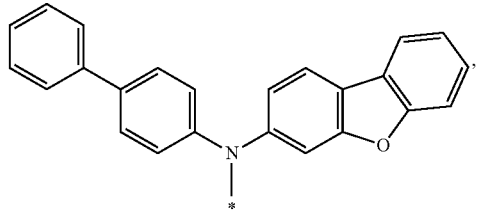
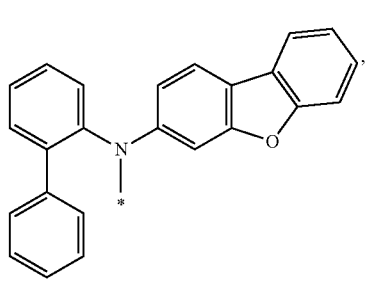
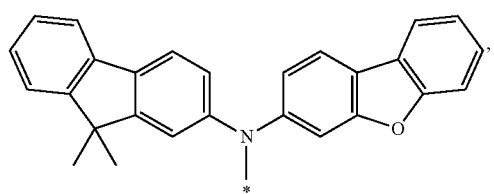
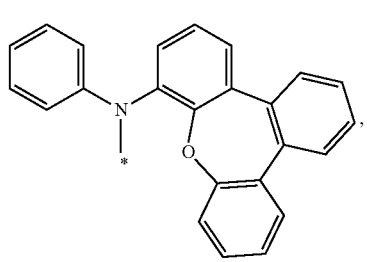
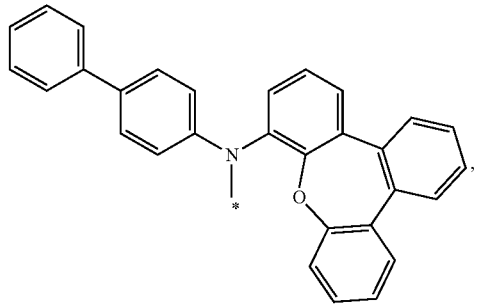
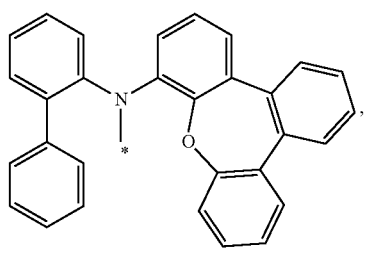

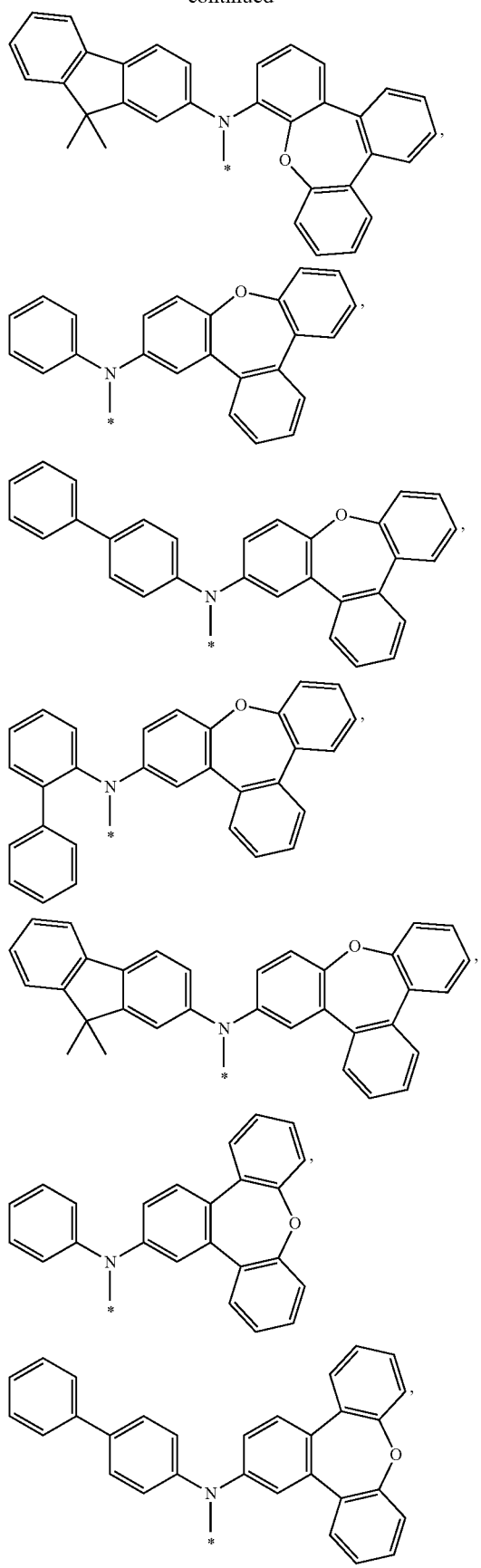
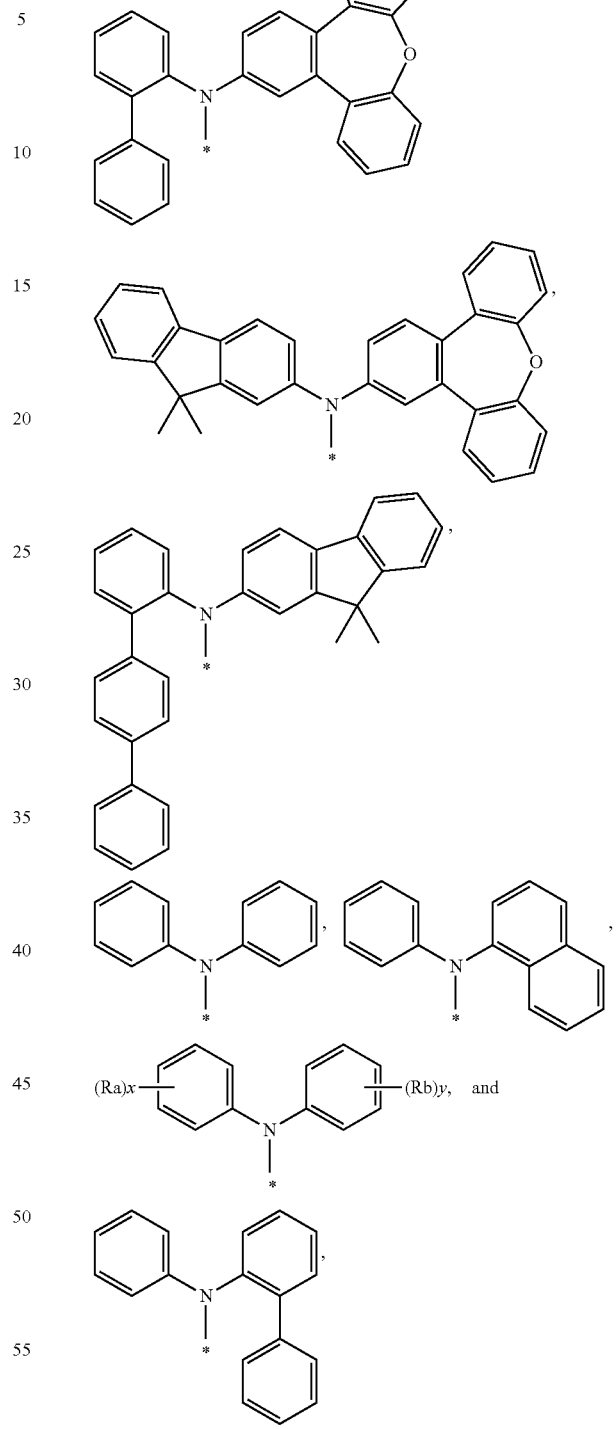
wherein * represents bonding positions, Ra and Rb are each independently $C_{1-20}$ alkyl, and x and y are each independently 1 or 2. Herein, Ra and Rb can be the same. X and y can be the same. Examples of Ra and Rb can be methyl, ethyl or propyl. In addition, n1 or n2 can be 0.
According to one embodiment, n1 is 0 and n2 is 1. According to another embodiment, n1 is 1 and n2 is 1. In these two embodiments, $L_{n1}$-$NAr_1Ar_2$ and -$Q_{n2}$-$NAr_3Ar_4$ can be each independently selected from the group consisting of:
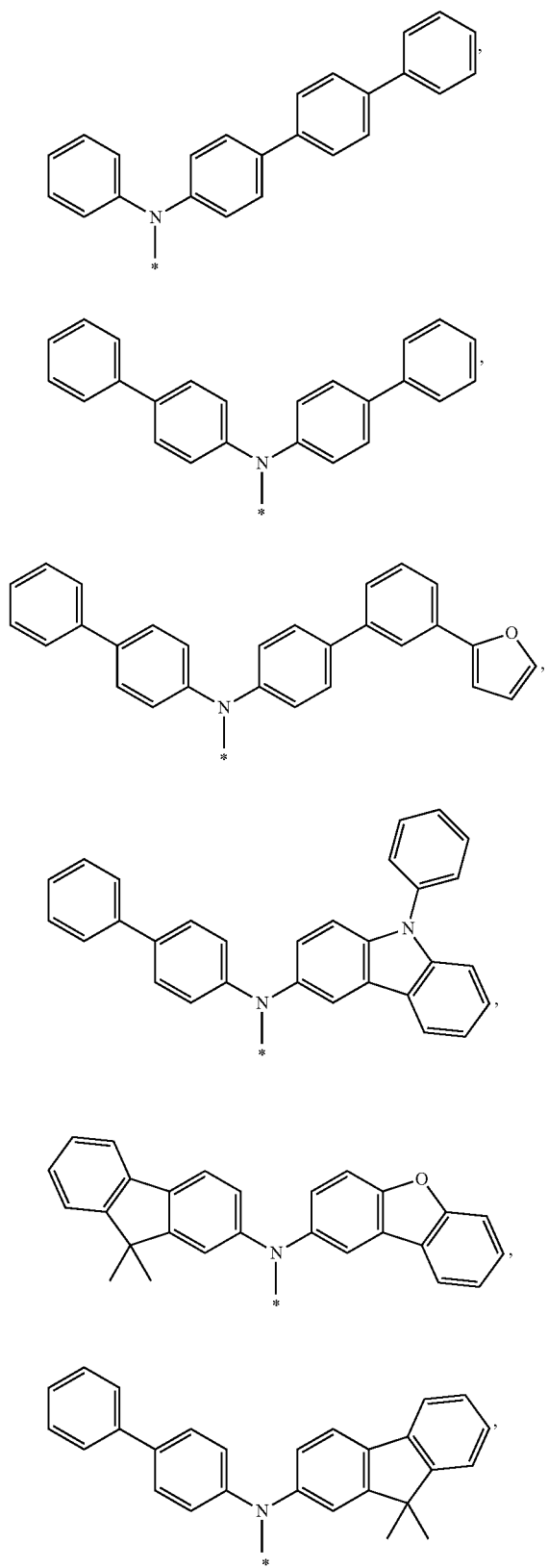
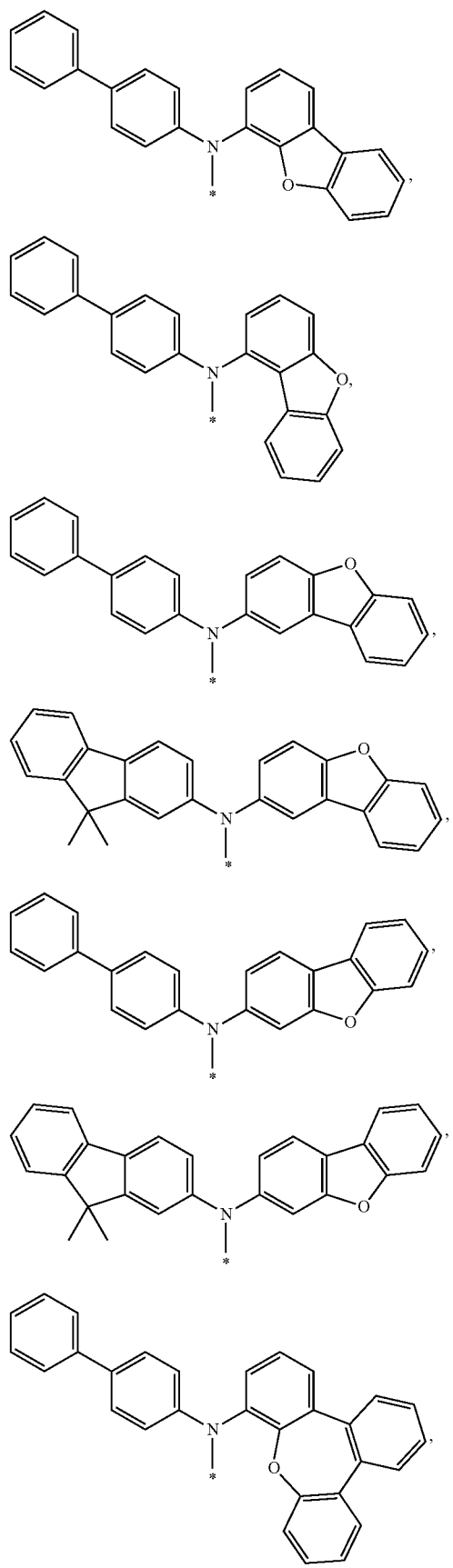

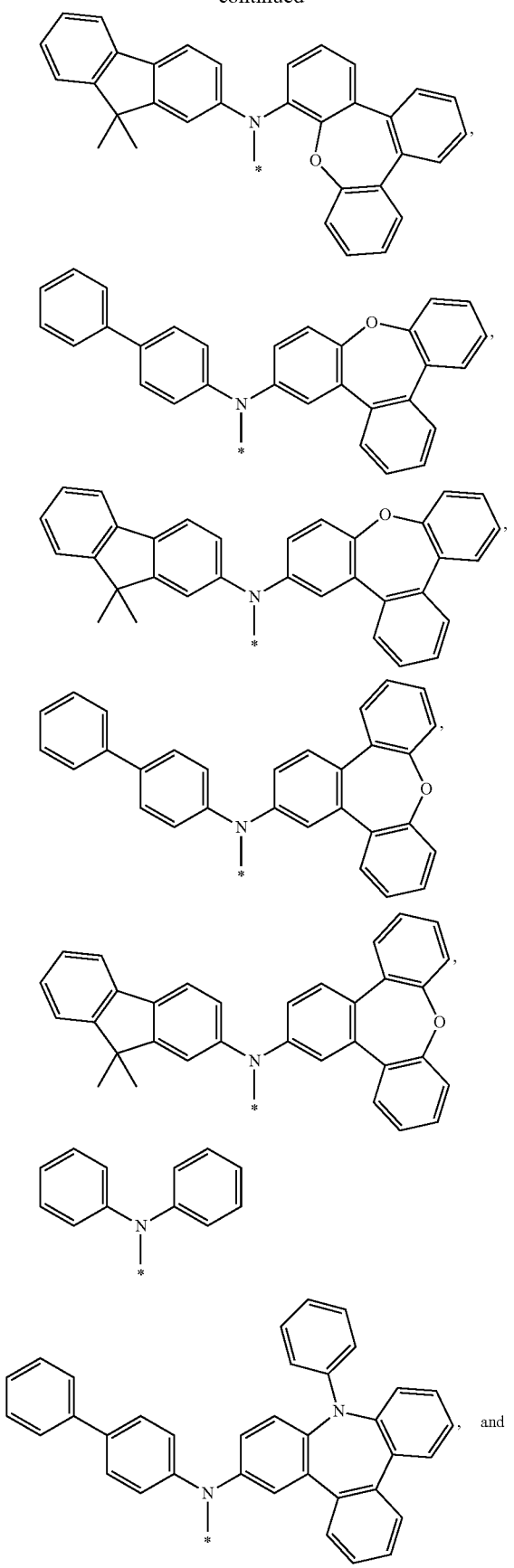

wherein * represents bonding positions. The definitions of Ra, Rb, x and y are the same as those illustrated above. In these two embodiments, L and Q can be each independently a substituted or unsubstituted $C_6$-$C_{40}$arylene group such as phenylene.

Hereinafter, substitutes of Formula (I) is described in detail. Substitutes that are not defined in the present disclosure are defined as known in the art.

In the present disclosure, the unsubstituted alkyl group can be linear or branched. Examples of the alkyl group include $C_1$-$C_{20}$alkyl, $C_{1-10}$alkyl, or $C_{1-6}$alkyl. Specific examples of the unsubstituted alkyl group include, but are not limited to, methyl, ethyl, n-propyl, iso-propyl, n-butyl, sec-butyl, iso-butyl, tert-butyl, pentyl, neo-pentyl, or hexyl. Herein, at least one hydrogen atom of the unsubstituted alkyl group may be substituted with a halogen group, an alkyl group, an alkenyl group, an alkoxy group, a cycloalkyl group, an aryl group, an arylalkyl group, an arylalkenyl group, a heterocyclic group, a nitrile group, or an acetylene group.

In the present disclosure, the unsubstituted aryl group refers to aromatic hydrocarbon group. Examples of the aryl group can be $C_6$-$C_{40}$ aryl, or $C_6$-$C_{20}$ aryl. In addition, examples of the aryl group can a monocyclic, bicyclic, tricyclic, or polycyclic aromatic hydrocarbon group; wherein two or more rings may be fused to each other or linked to each other via a single bond. Specific examples of the unsubstituted aryl group include, but are not limited to phenyl, biphenylyl, terphenyl, quarterphenyl, naphthyl, anthryl, benzanthryl, phenanthryl, naphthacenyl, pyrenyl, chrysenyl, benzo[c]phenanthryl, benzo[g]chrysenyl, triphenylenyl, fluorenyl, spirobifluorenyl, benzofluorenyl, or dibenzofluorenyl. Herein, at least one hydrogen atom of the unsubstituted aryl group may be substituted with the same substituents described above related to the alkyl group. In addition, the definition of the arylene group is similar to those stated above, and the detail description of the arylene group is not repeated herein.

In the present disclosure, the unsubstituted heterocyclic group refers to non-aromatic or aromatic hydrocarbon group. Examples of the heterocyclic group can be a $C_1$-$C_{40}$heterocyclic group, $C_2$-$C_{20}$heterocyclic group or a $C_4$-$C_{20}$heterocyclic group. In addition, examples of the heterocyclic group can be a monocyclic, bicyclic, tricyclic, or polycyclic heteroaryl or heterocycloalkyl having at least one heteroatom which is selected from the group consisting of O, S and N; wherein two or more rings may be fused to each other or linked to each other via a single bond. Specific examples of the unsubstituted heterocyclic group include, but are not limited to, pyroryl, pyrazinyl, pyridinyl, piperidinyl, indolyl, isoindolyl, imidazolyl, benzoimidazolyl, furyl, ozazolyl, thiazolyl, triazolyl, thiadiazolyl, benzothiazolyl, tetrazolyl, oxadiazolyl, triazinyl, carbazolyl, benzofuranyl, isobenzofuranyl, dibenzofuranyl, dibenzothiofuranyl, dibenzothiophenyl, quinolyl, isoquinolyl, quinoxalinyl, phenantridinyl, acridinyl, phenanthrolinyl, phenazinyl, phenothiazinyl, phenoxazinyl, oxazolyl, oxadiazoyl, furazanyl, thienyl, benzothiophenyl, tribenzyloxepinyl, thiophenyl, or benzooxazolyl. Herein, at least one hydrogen atom of the unsubstituted heterocyclic group may be substituted with the same substituents described above related to the alkyl group.

In one embodiment, two or more aryl or hetero rings may be directly linked to each other to form a spiro structure. For example, fluorenyl and tribenzo-cycloheptatrienyl may be linked to each other to form a spiro structure.

In the present disclosure, halogen includes F, Cl, Br and I; and preferably is F or Br.

In the present disclosure, the unsubstituted alkoxy group refers to a moiety that the alkyl defined above coupled with an oxygen atom. Examples of the alkoxy group can include linear or branched $C_{1-10}$alkoxy, or linear or branched $C_{1-6}$alkoxy. Specific examples of alkoxy include, but are not limited to, methoxy, ethoxy, n-propoxy, iso-propoxy, n-butoxy, iso-butoxy, sec-butoxy, tert-butoxy, pentyloxy, neopentyloxy or hexyloxy. Herein, at least one hydrogen atom of the unsubstituted alkoxy group may be substituted with the same substituents described above related to the alkyl group.

In the present disclosure, the unsubstituted cycloalkyl group refers to a monovalent saturated hydrocarbon ring system having 3 to 20 carbon atoms, or 3 to 12 carbon atoms. Specific examples of the unsubstituted cycloalkyl group include, but are not limited to, cyclopropyl, cyclobutyl, cyclopentyl, cyclohexyl, cycloheptyl, and cyclooctyl. Herein, at least one hydrogen atom of the unsubstituted cycloalkyl group may be substituted with the same substituents described above related to the alkyl group.

In the present disclosure, the unsubstituted alkenyl group can be linear or branched, and have at least one carbon-carbon double bond. Examples of the alkenyl group include $C_1$-$C_{20}$alkenyl, $C_{1-10}$alkenyl, or $C_{1-6}$alkenyl. Specific examples of the unsubstituted alkenyl group include, but are not limited to ethenyl, propenyl, propenylene, allyl, or 1,4-butadienyl. Herein, at least one hydrogen atom of the unsubstituted alkenyl group may be substituted with the same substituents described above related to the alkyl group.

Examples of the compound of Formula (I) may include any one of the following compounds (1) to (212).

(1)

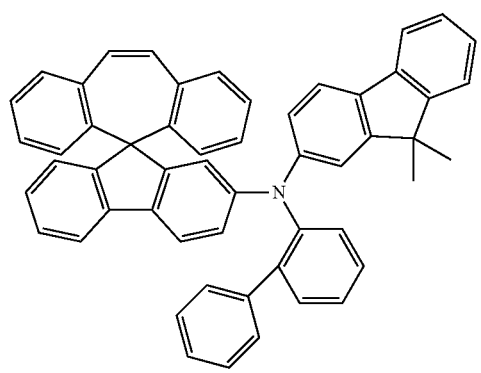

(2)

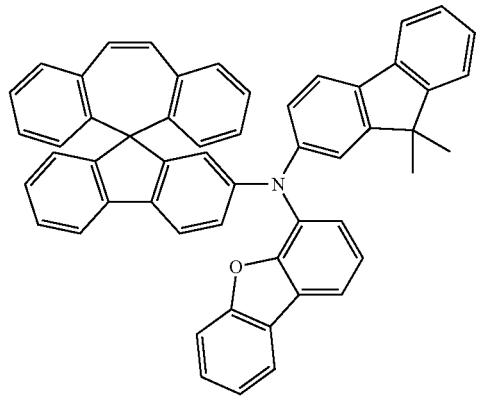

(3)

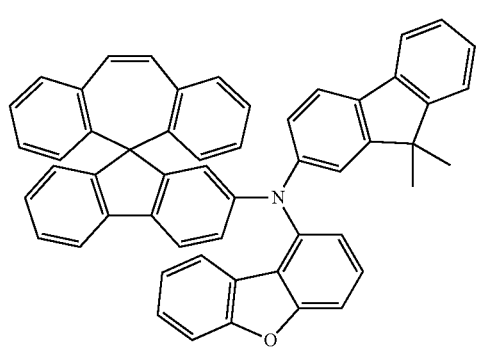

(4)

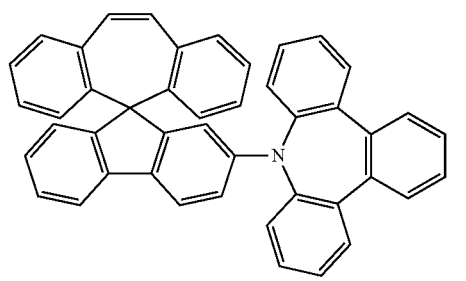

(5)

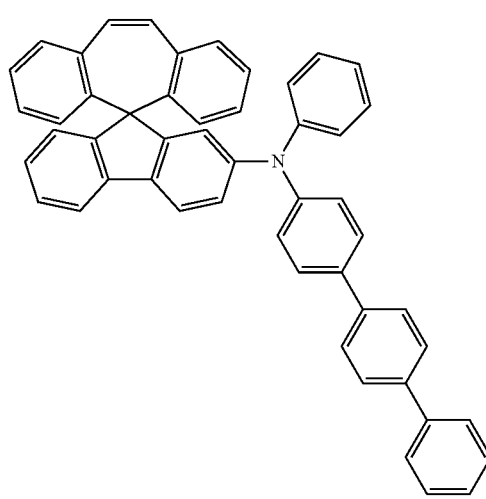

-continued
(6)
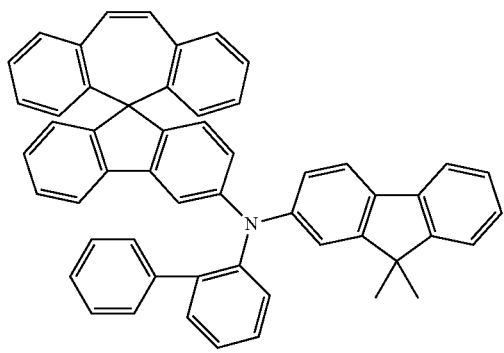
(7)
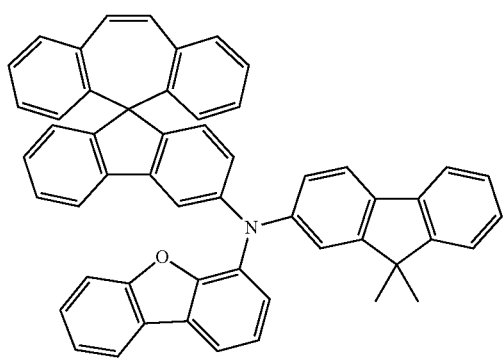
(8)
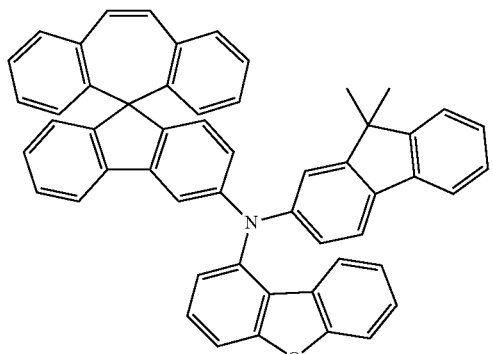
(9)
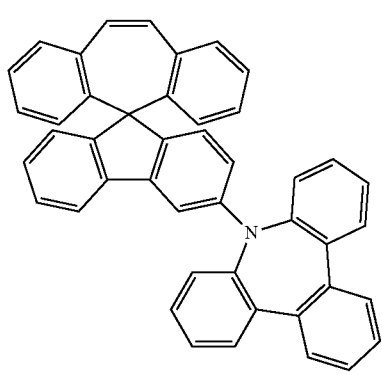
-continued
(10)
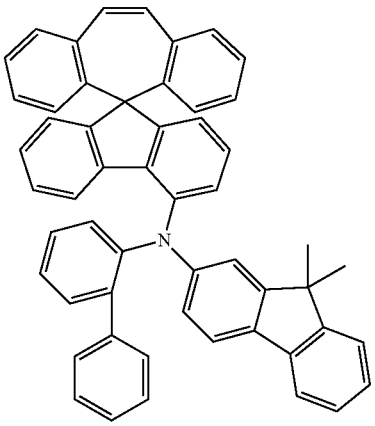
(11)
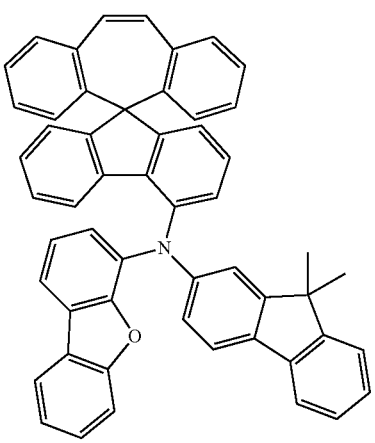
(12)
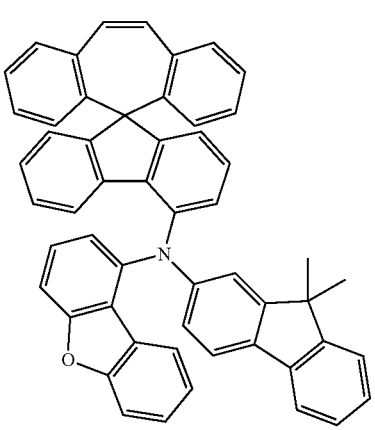

(13)
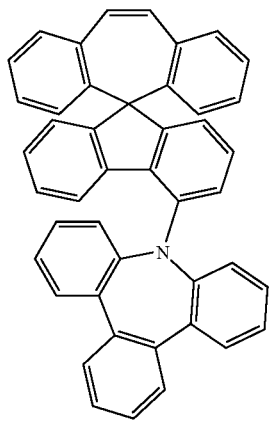
(14)
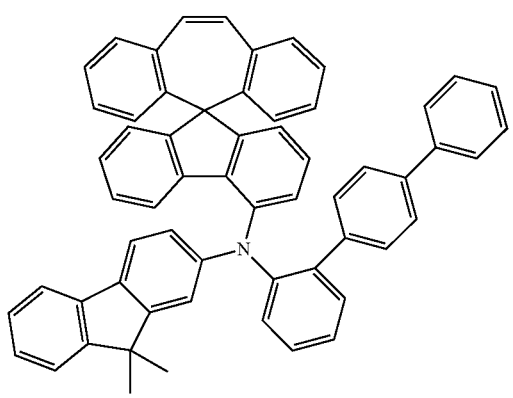
(15)
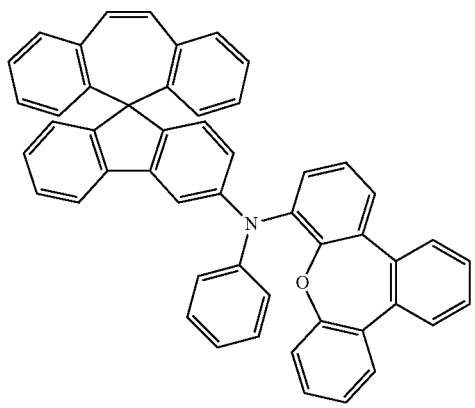
(16)
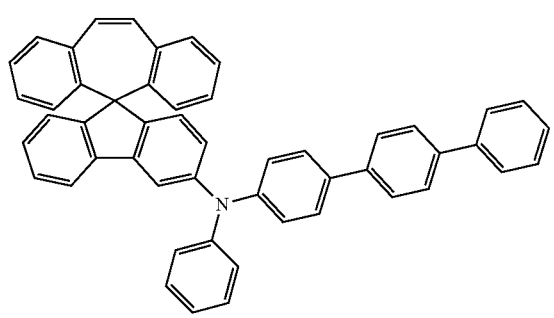
(17)
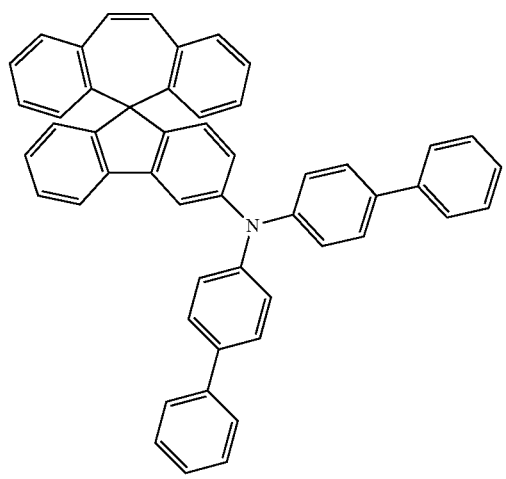
(18)
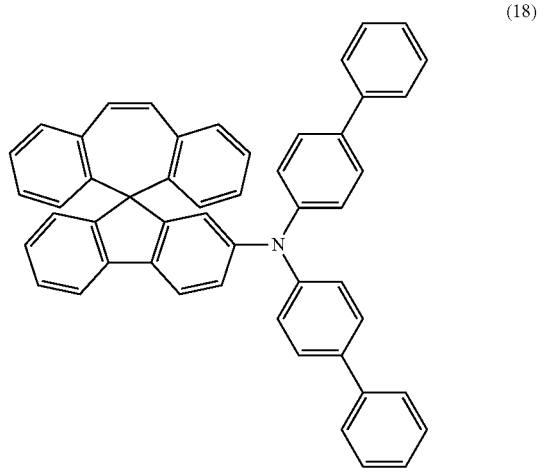
(19)
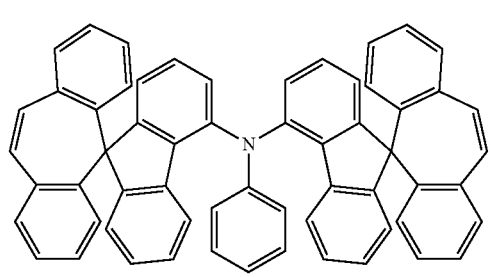

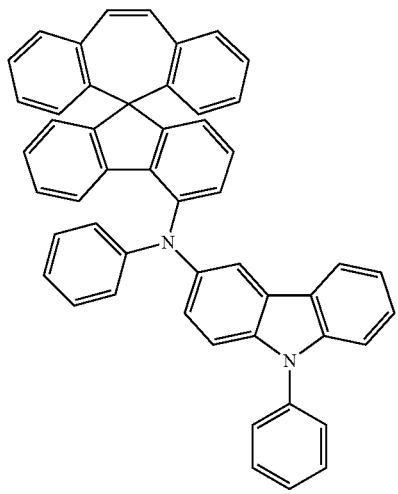
(20)
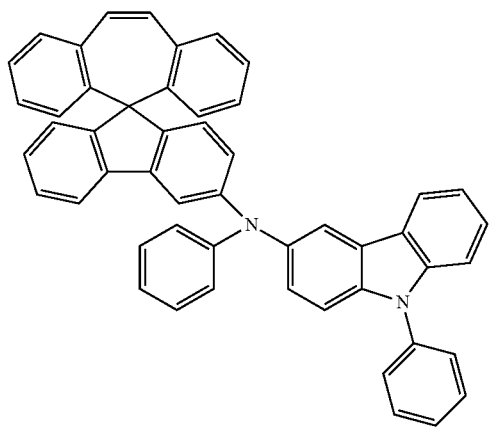
(23)
(21)
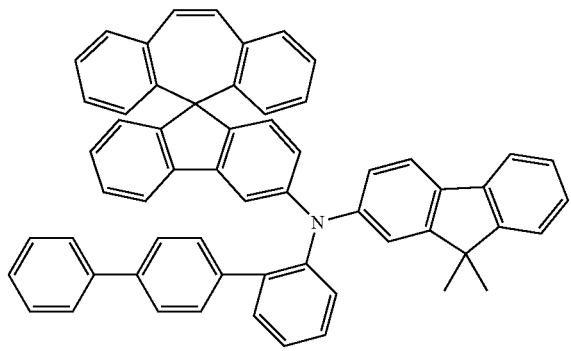
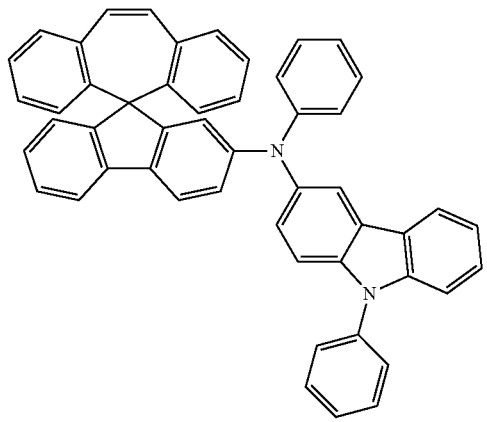
(24)
(22)
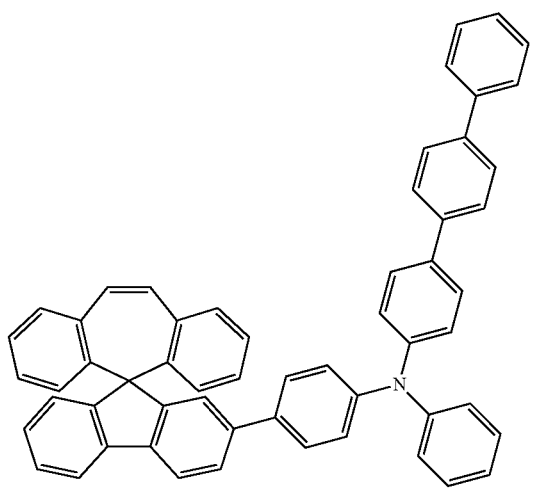
(25)

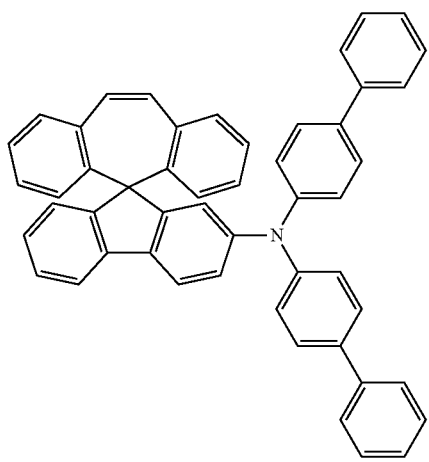
(26)
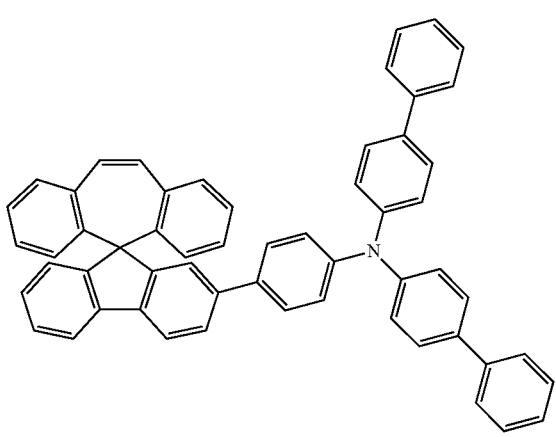
(27)
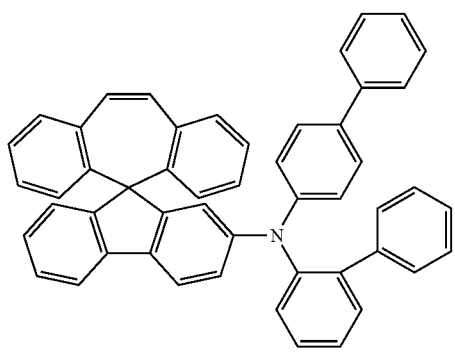
(28)
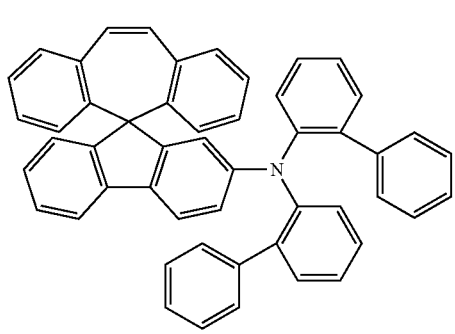
(29)
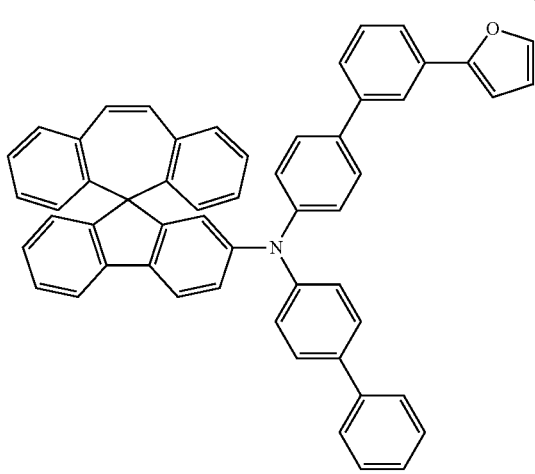
(30)
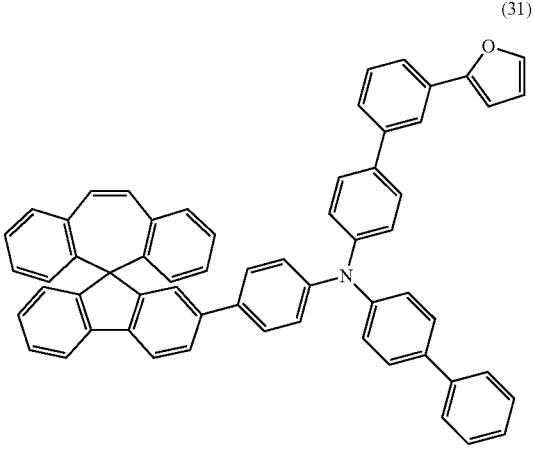
(31)
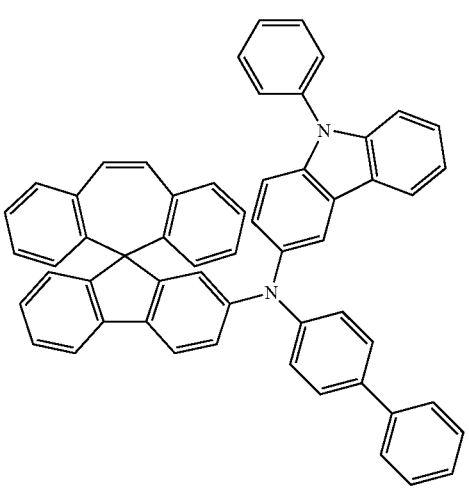
(32)

-continued
(33)
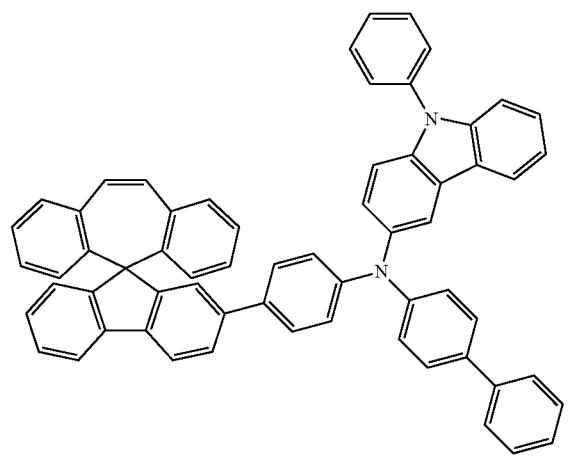
(34)
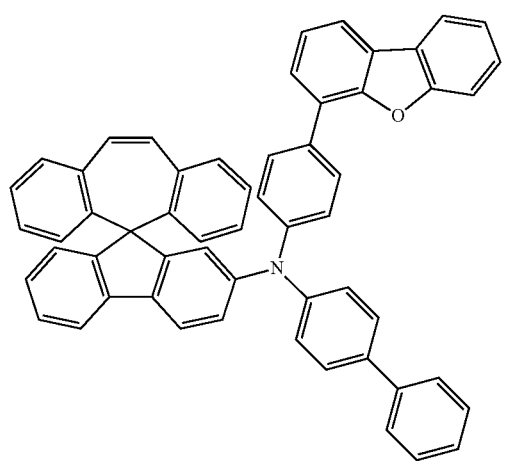
(35)
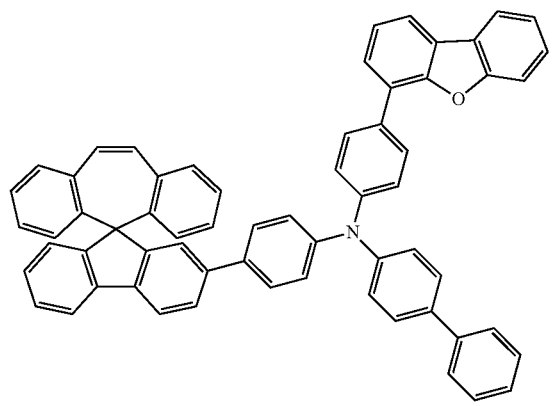
-continued
(36)
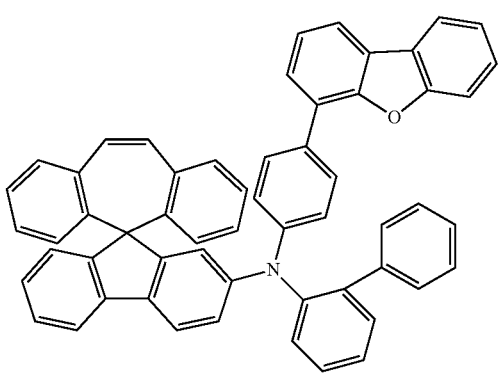
(37)
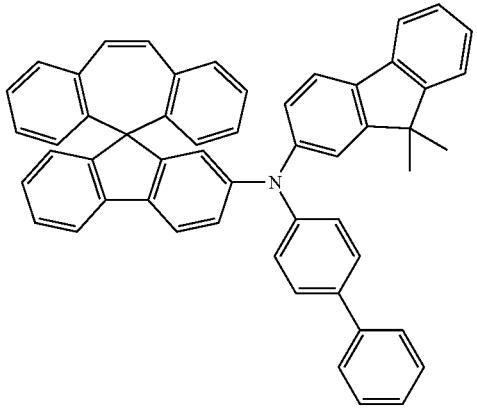
(38)
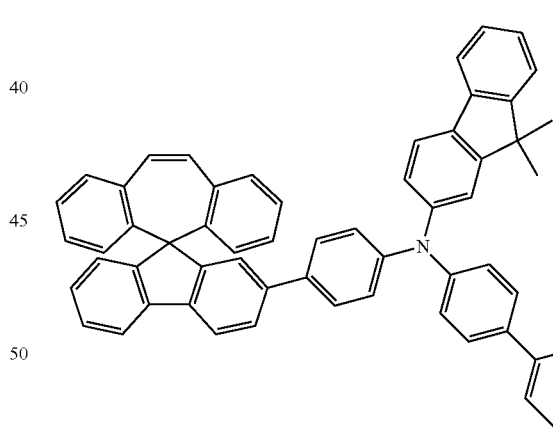
(39)
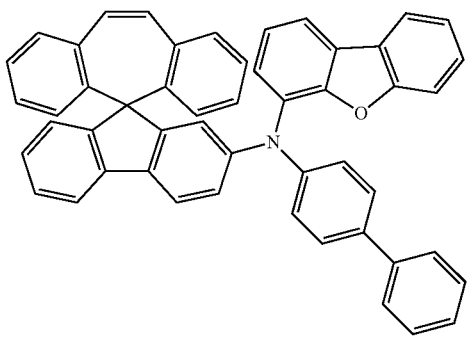

(40)
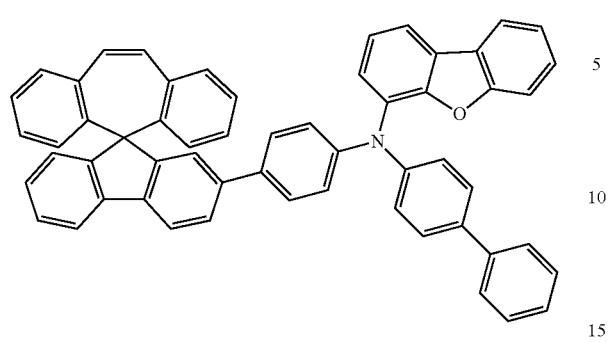
(41)
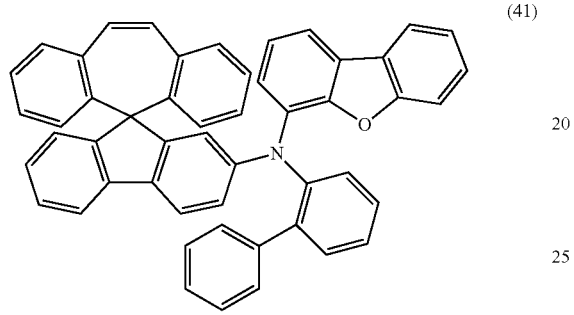
(42)
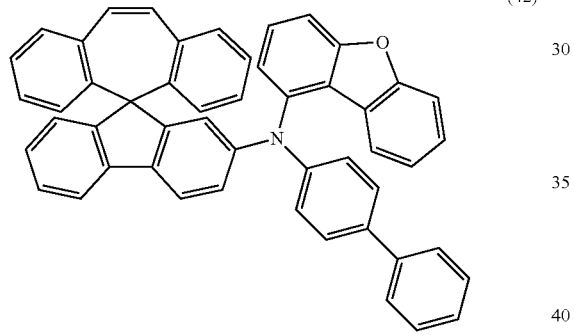
(43)
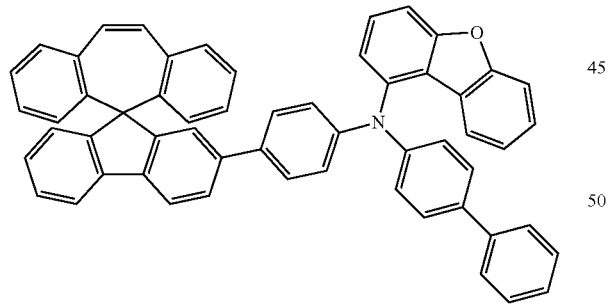
(44)
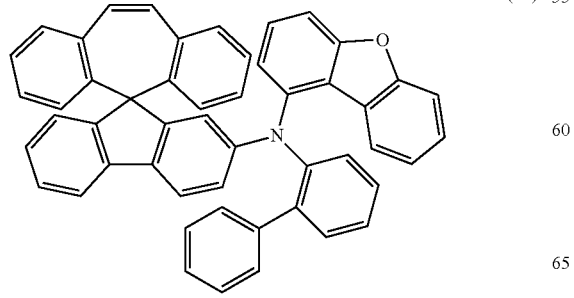
(45)
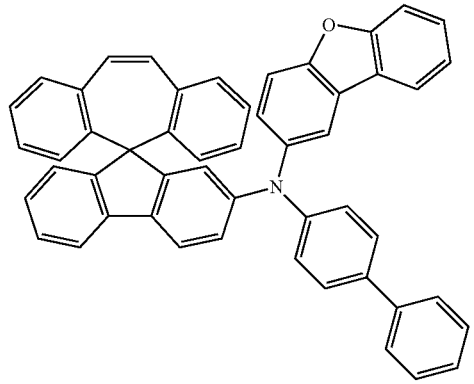
(46)
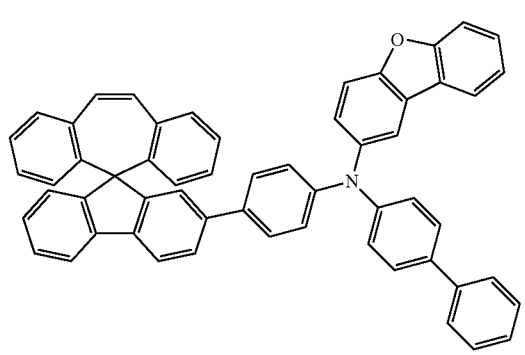
(47)
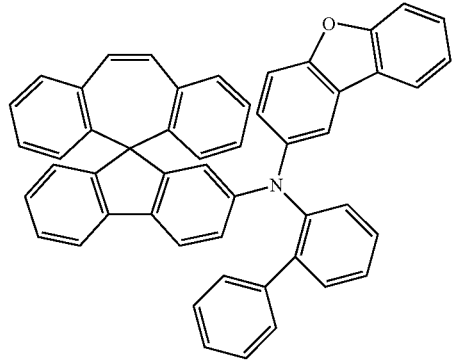
(48)
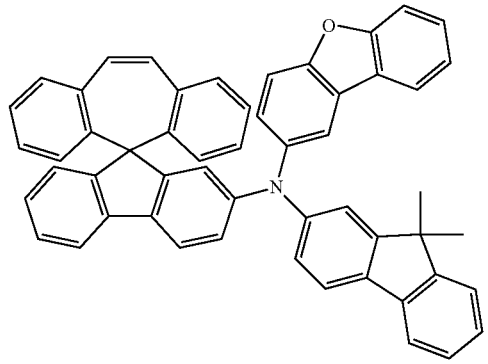

(49)
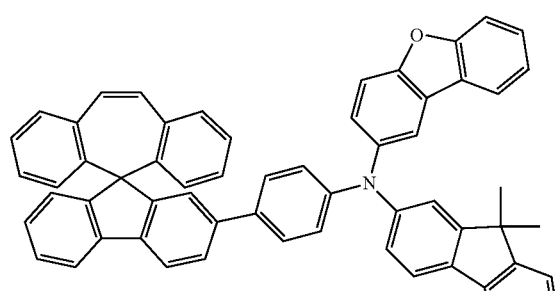
(50)
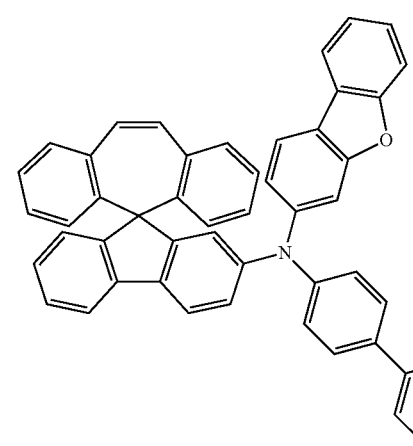
(51)
(52)
(53)
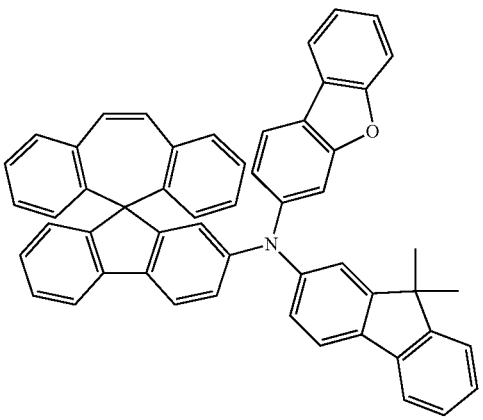
(54)
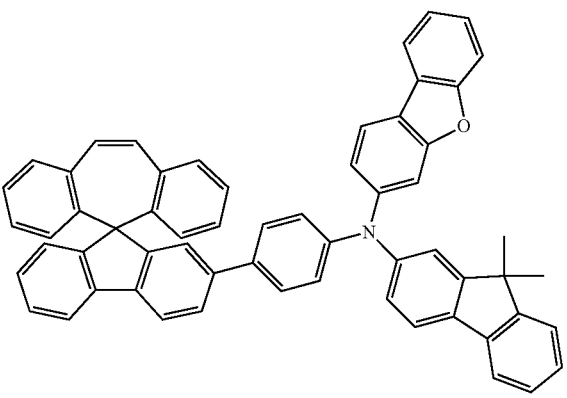
(55)
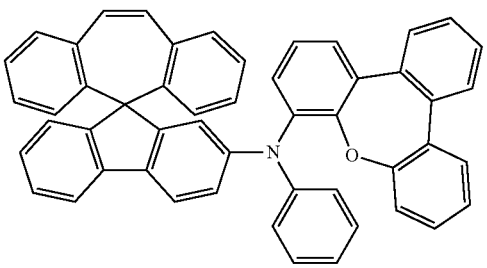
(56)
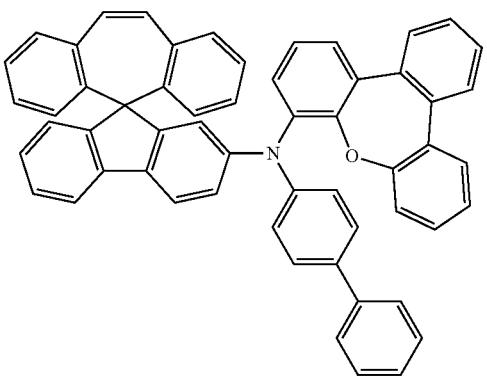

(57)
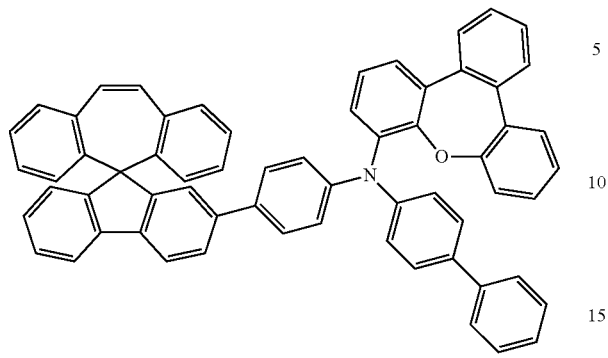
(58)
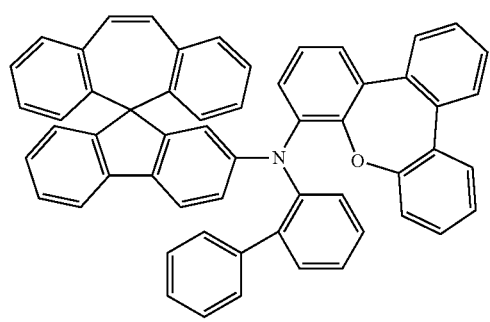
(59)
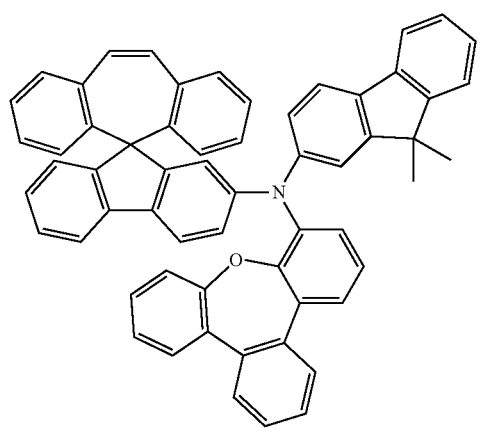
(60)
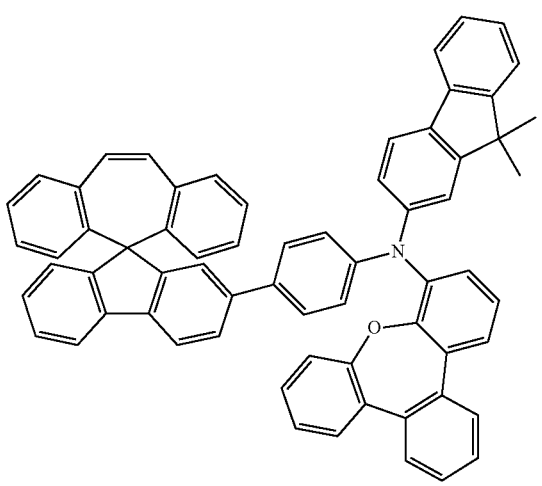
(61)
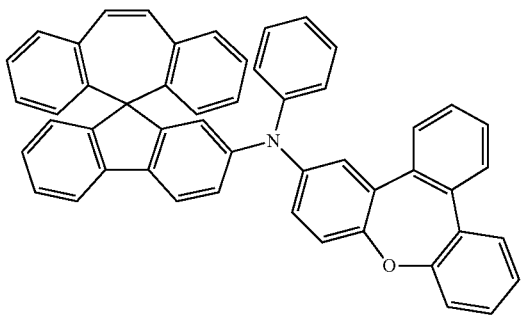
(62)
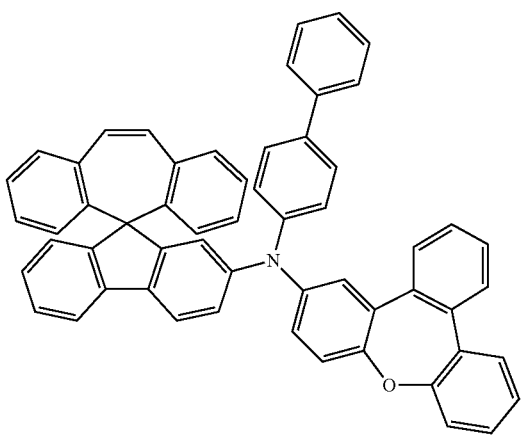
(63)
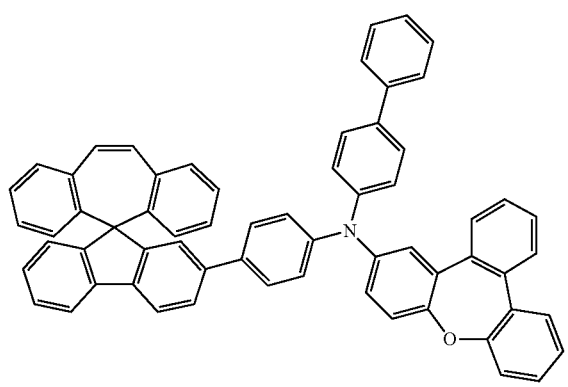
(64)
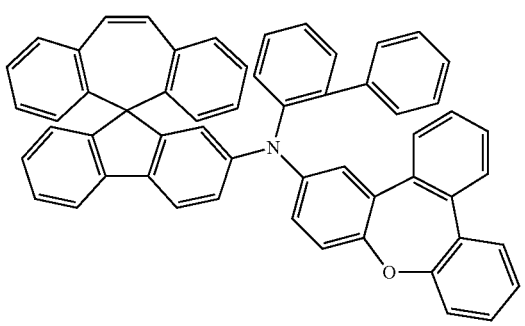

(65)
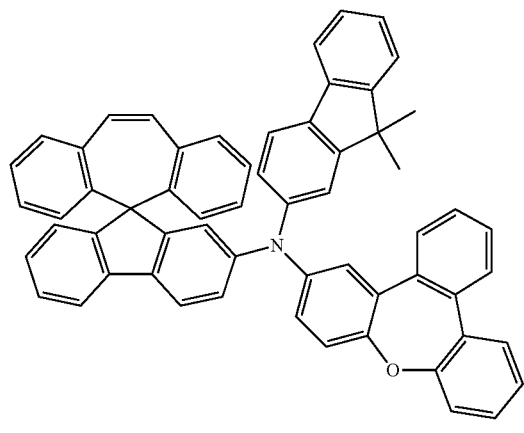
(68)
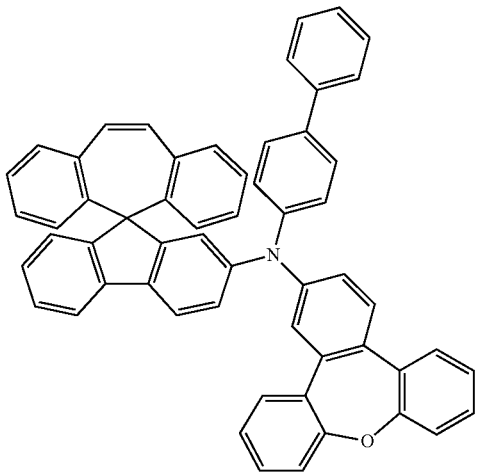
(66)
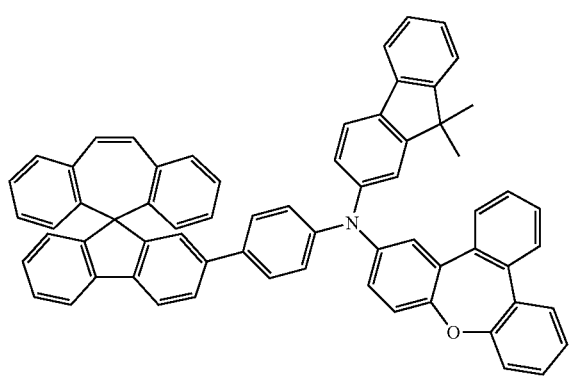
(69)
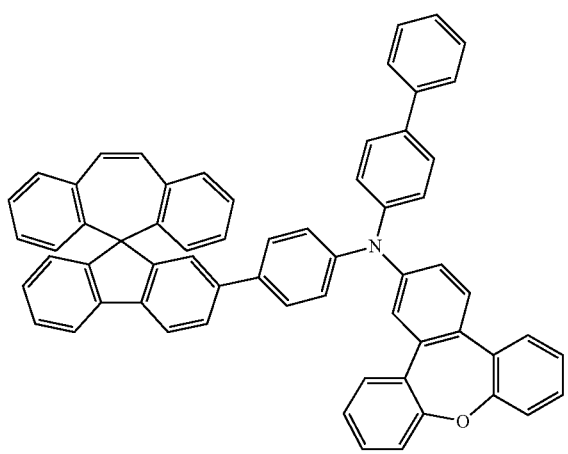
(67)
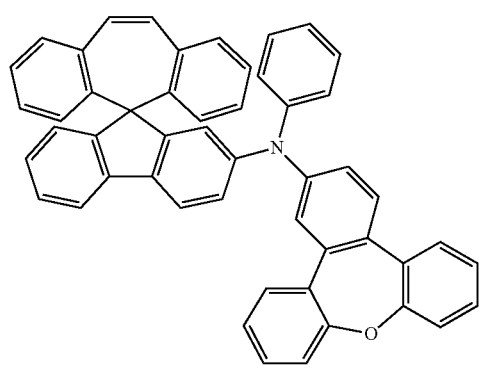
(70)
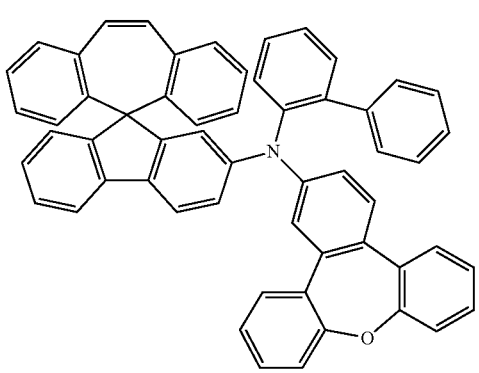

(71)
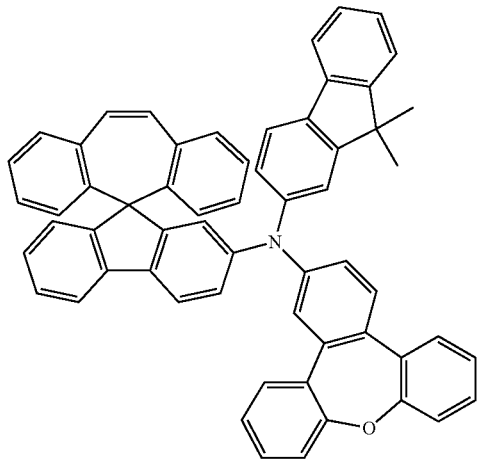
(72)
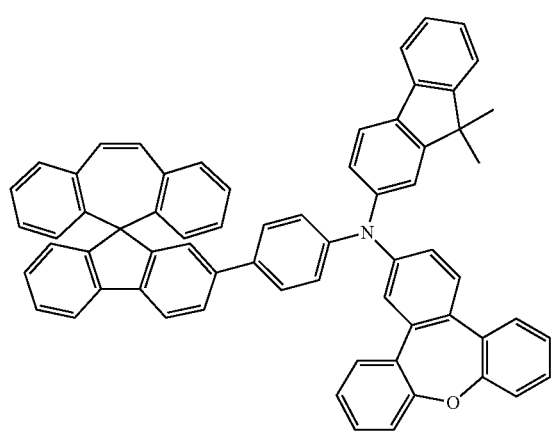
(73)
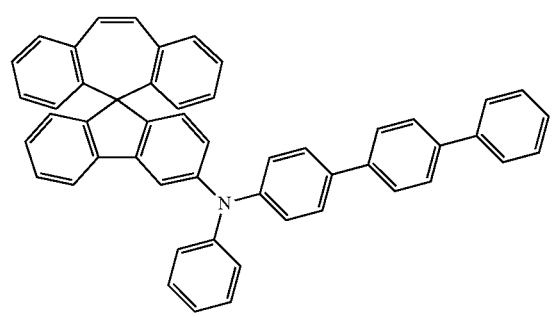
(74)
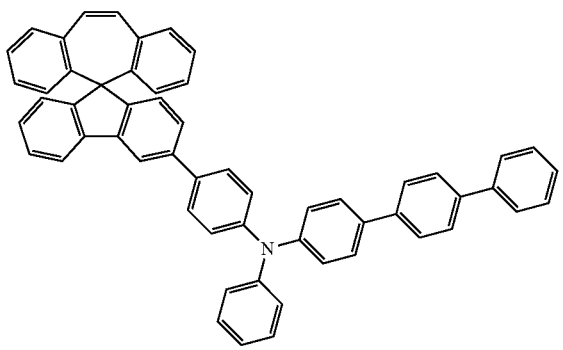
(75)
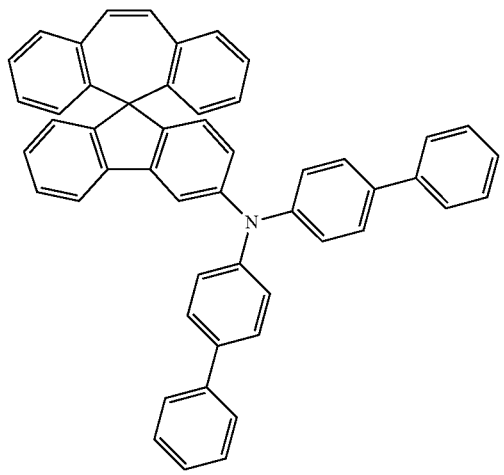
(76)
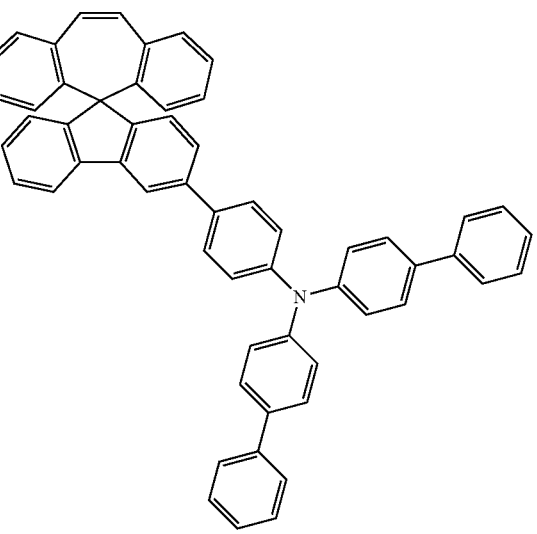
(77)
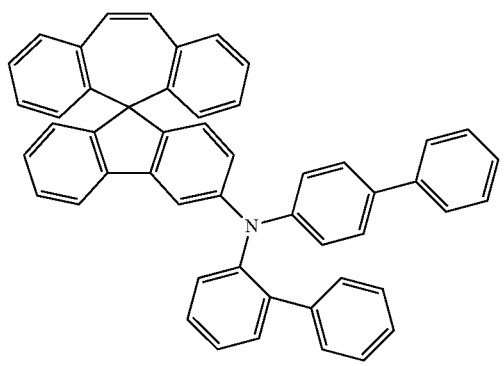

(78)
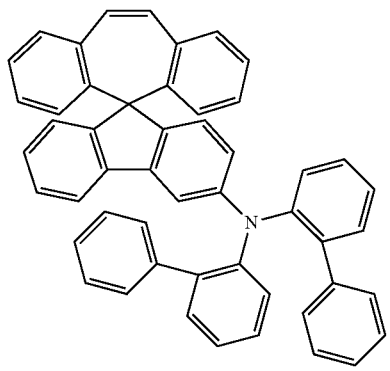
(81)
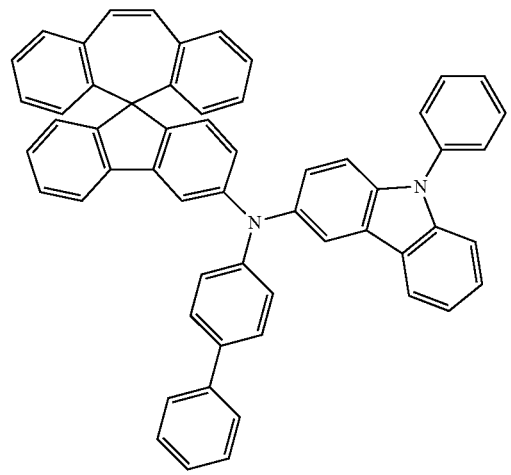
(79)
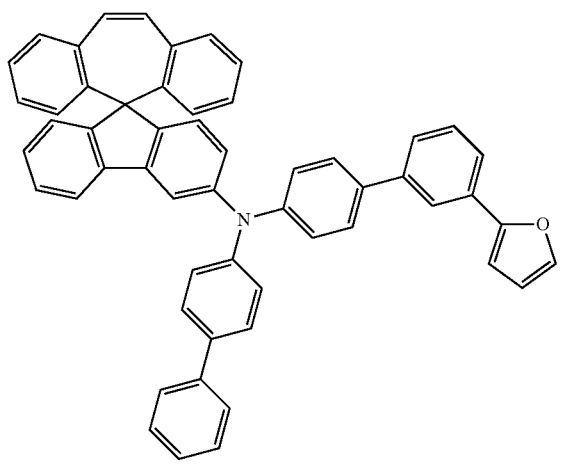
(82)
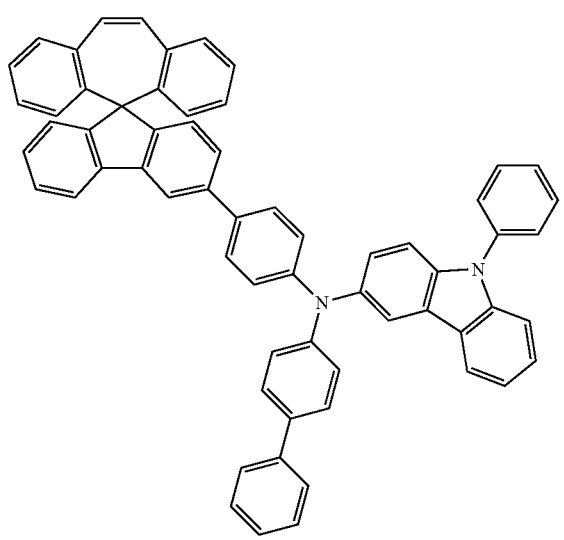
(80)
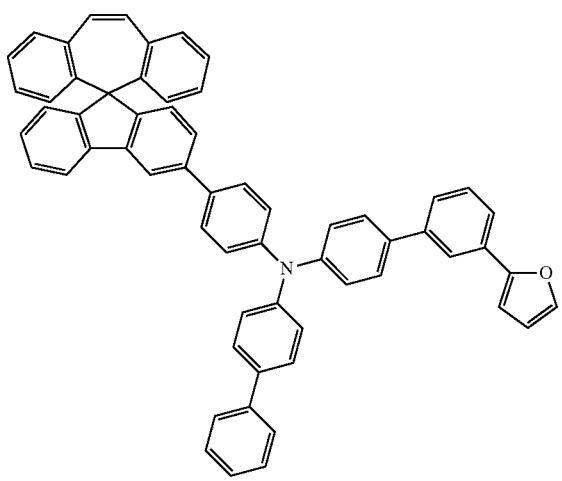
(83)
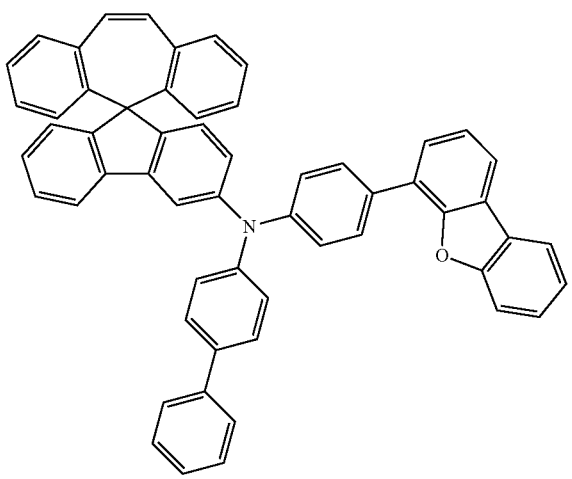

(84)
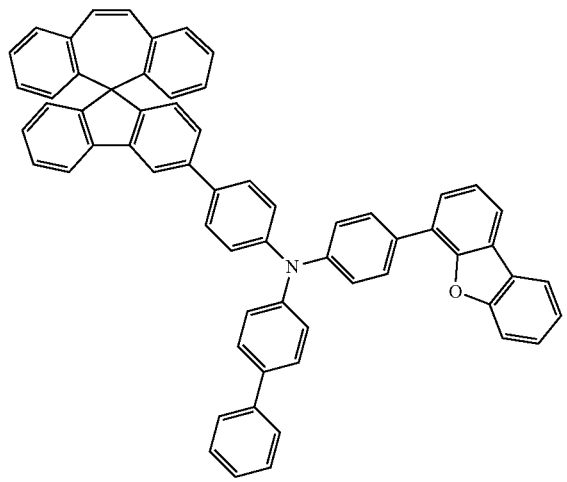
(85)
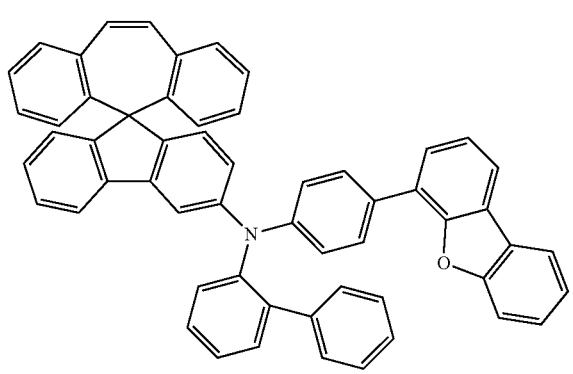
(86)
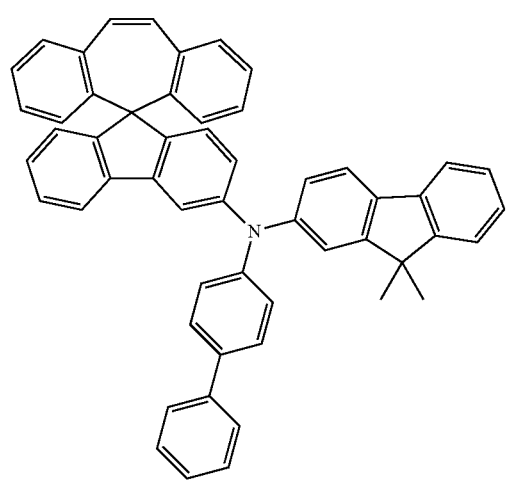
(87)
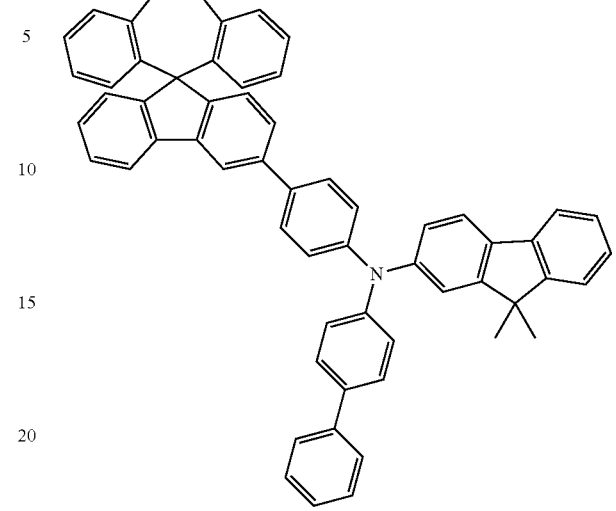
(88)
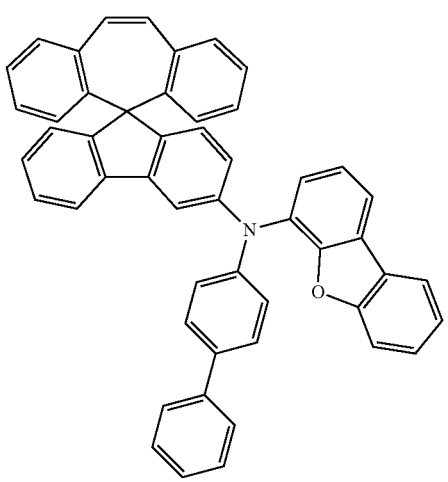
(89)
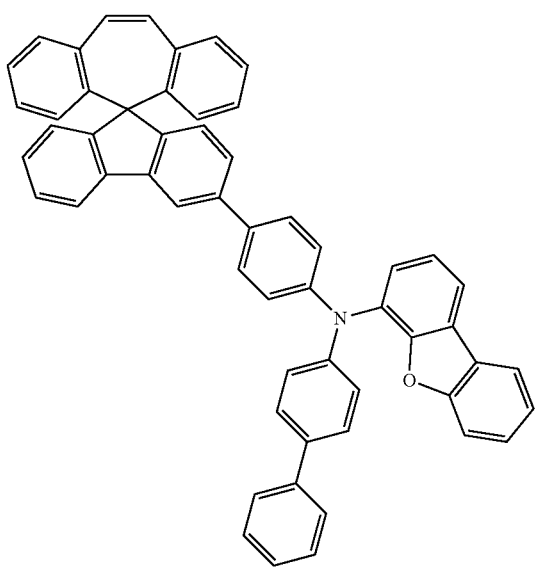

(90)
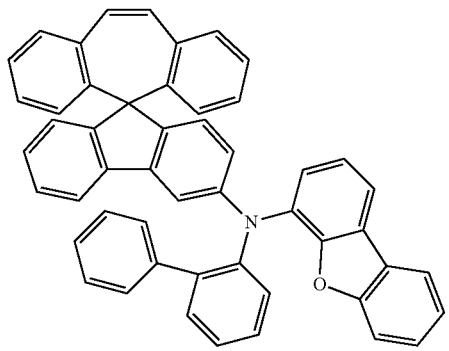
(91)
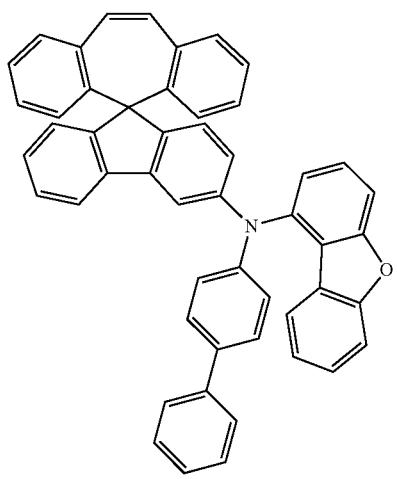
(92)
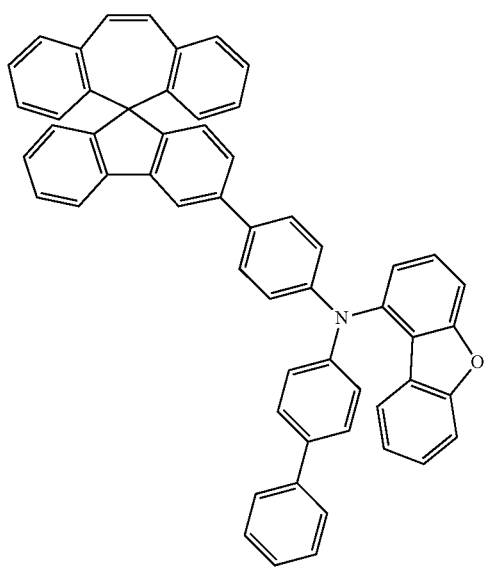
(93)
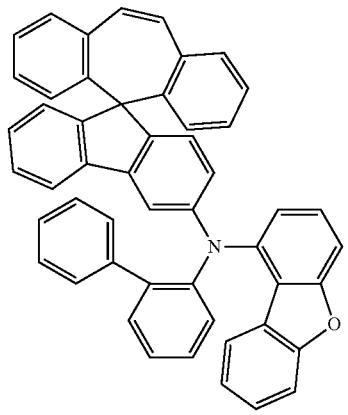
(94)
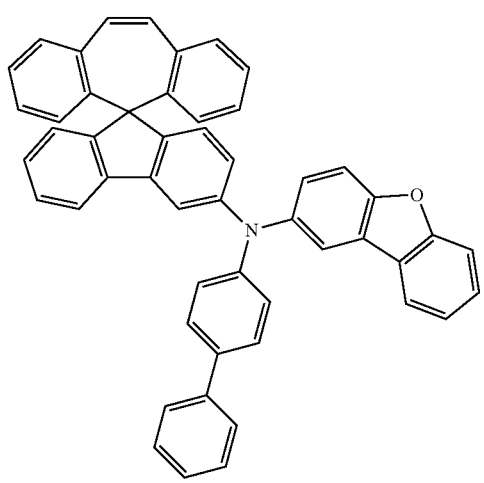
(95)
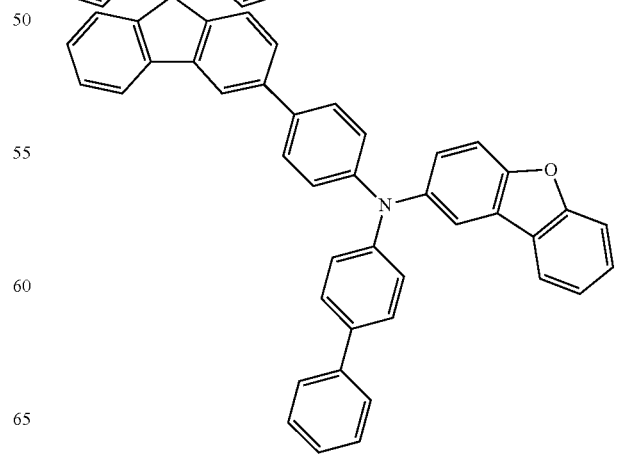

(96)
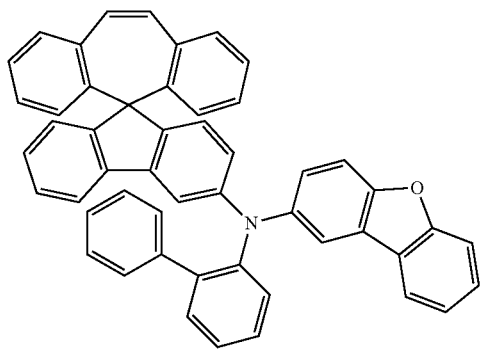
(97)
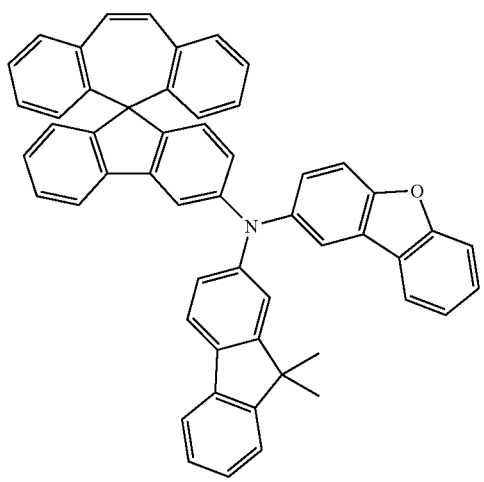
(98)
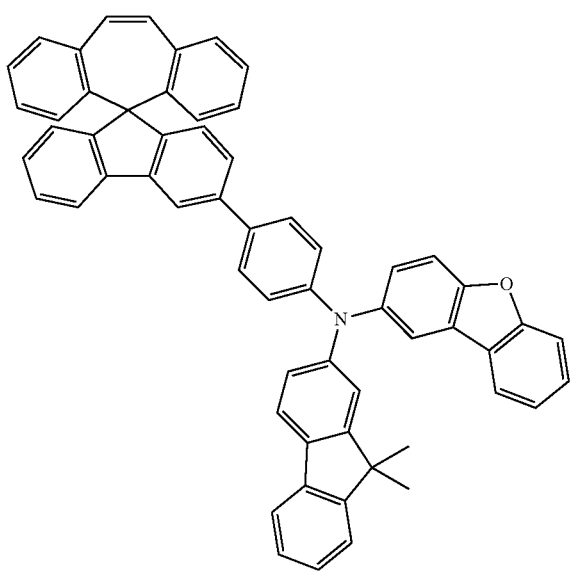
(99)
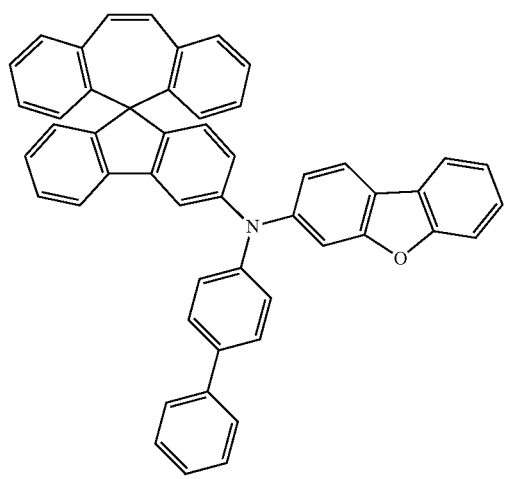
(100)
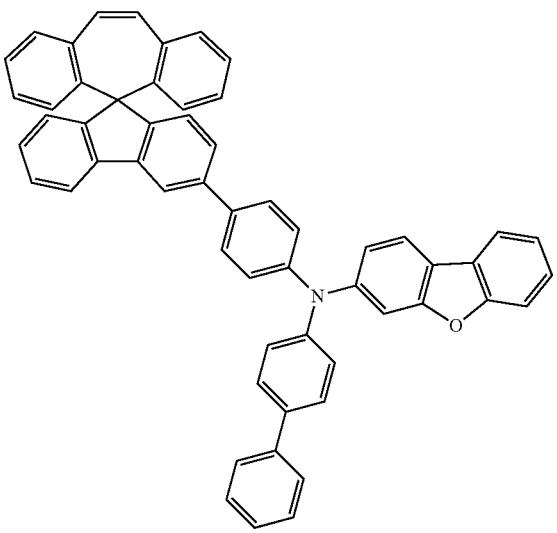
(101)
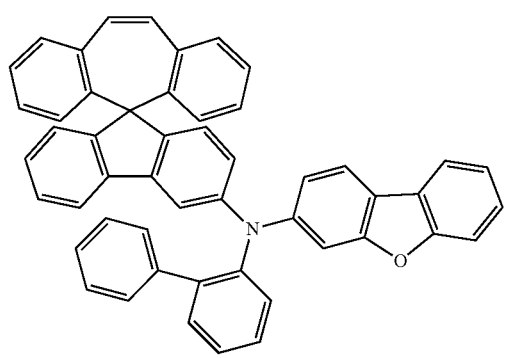

(102)
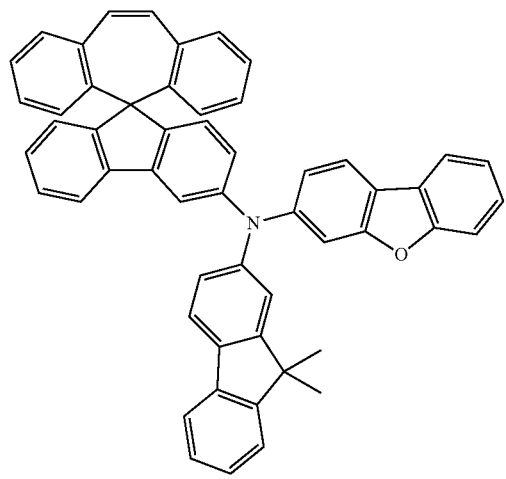
(103)
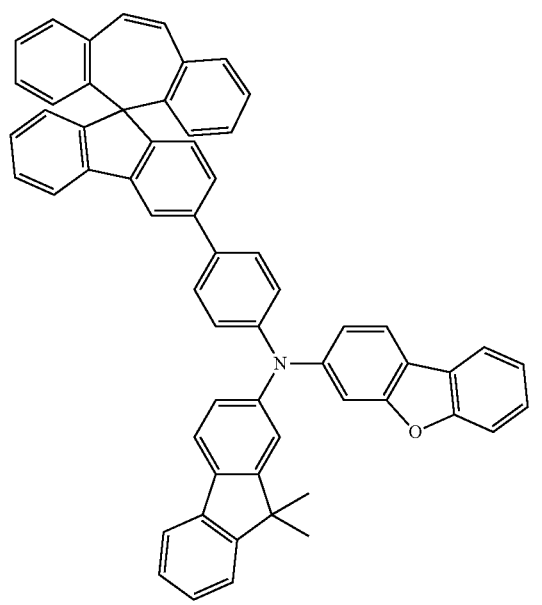
(104)
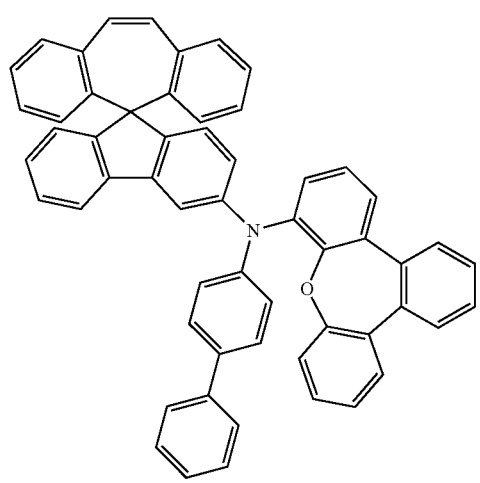
(105)
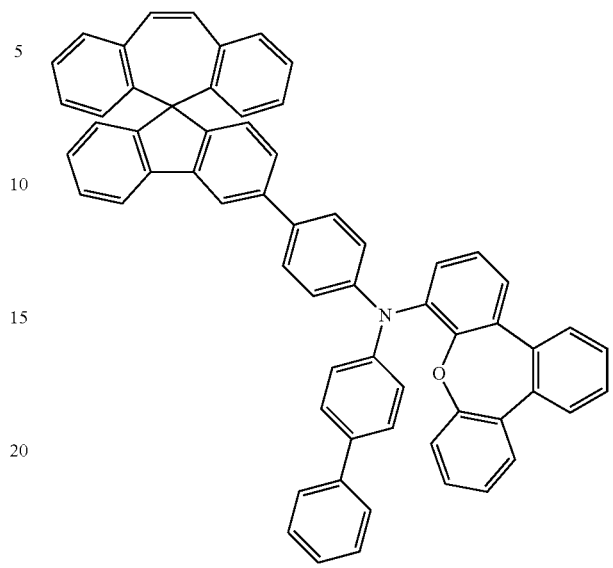
(106)
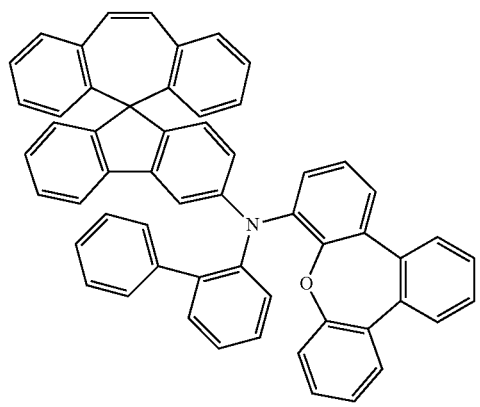
(107)
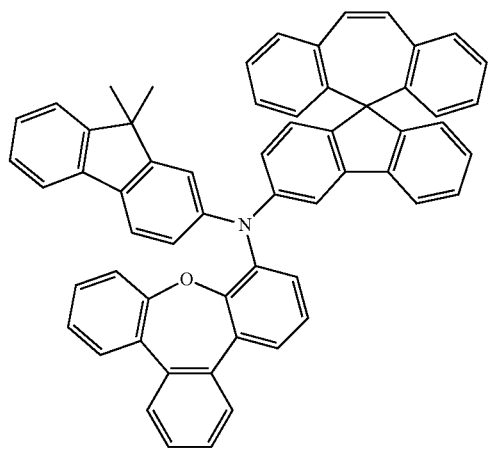

(108)
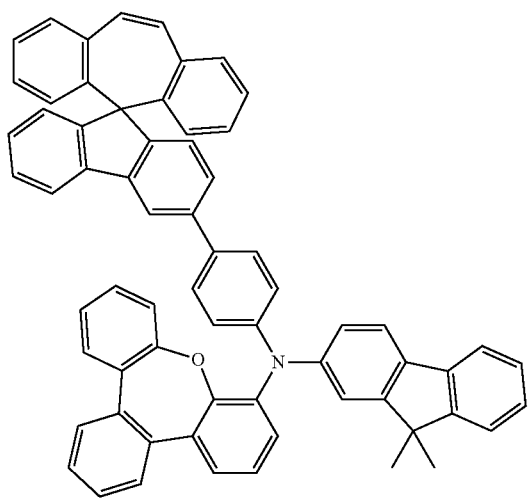
(109)
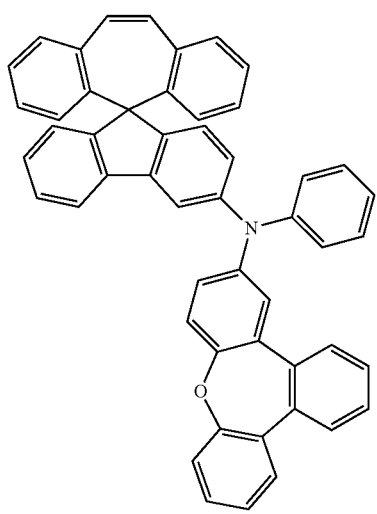
(110)
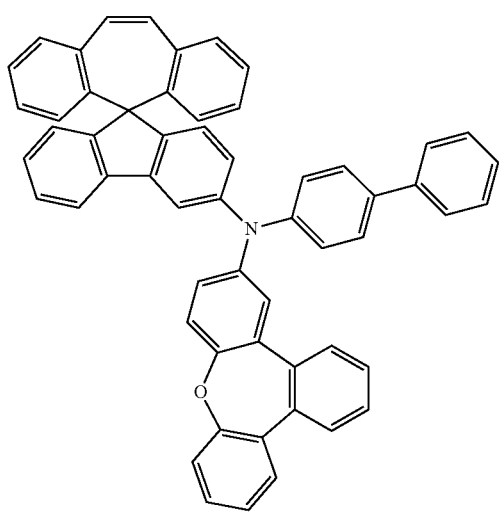
(111)
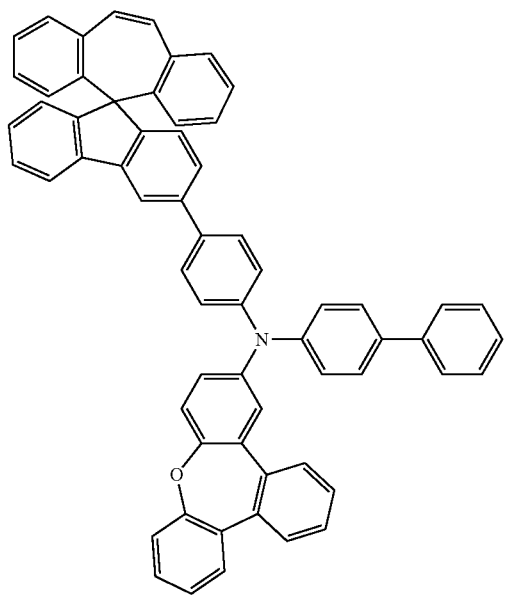
(112)
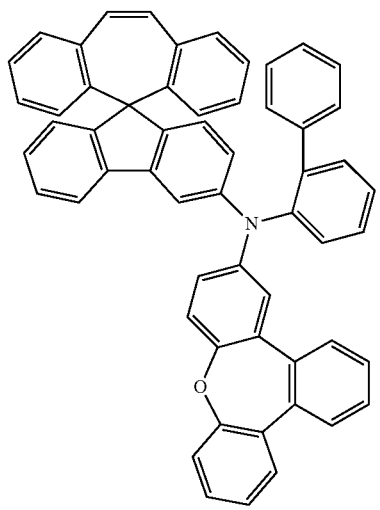
(113)
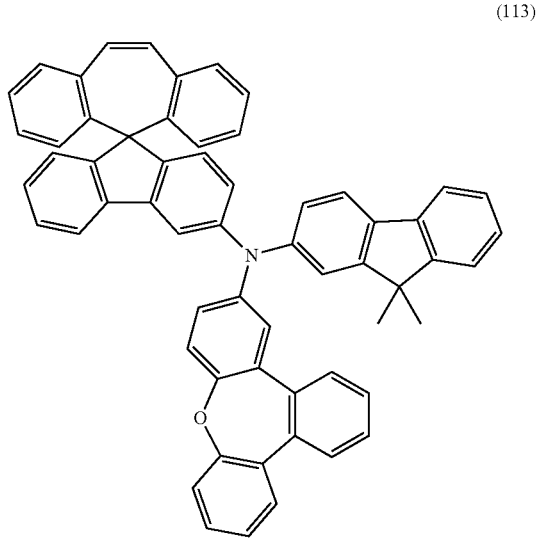

(114)
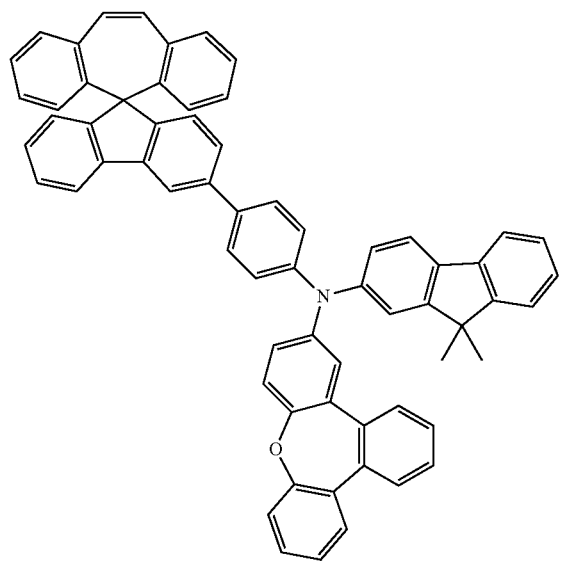
(115)
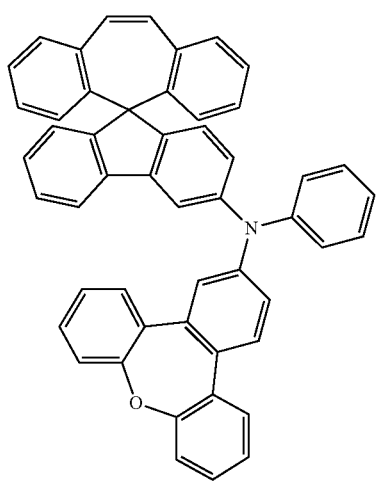
(116)
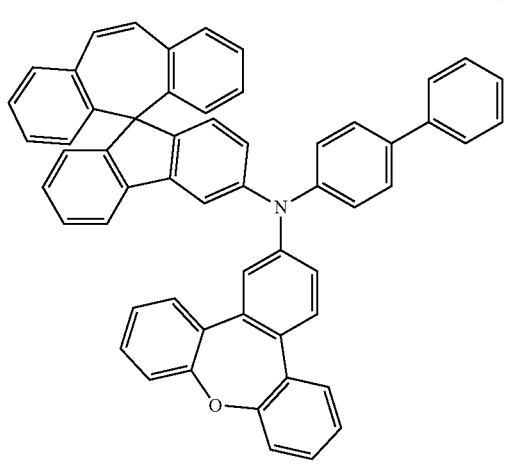
(117)
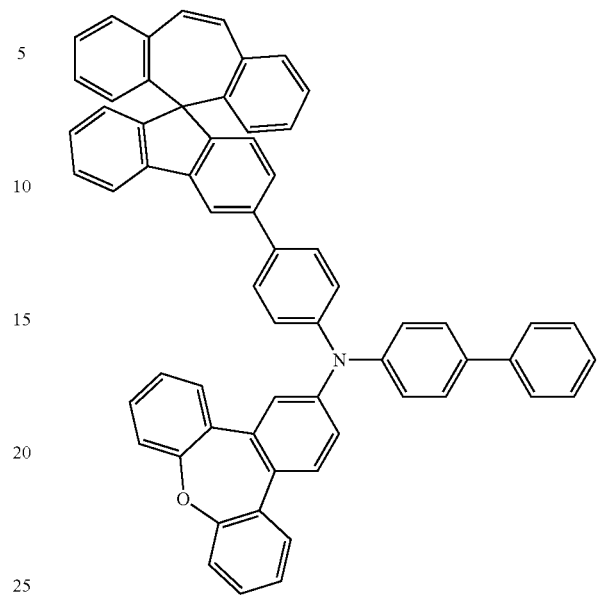
(118)
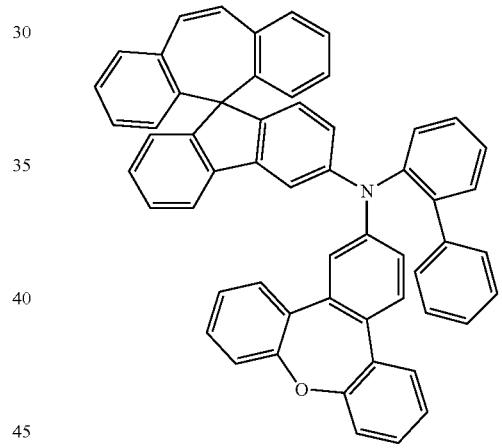
(119)
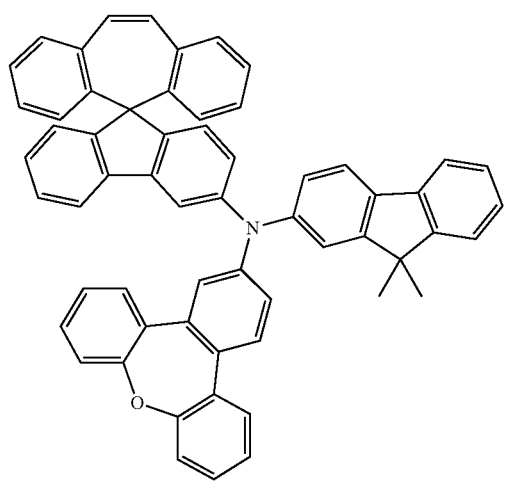

(120)
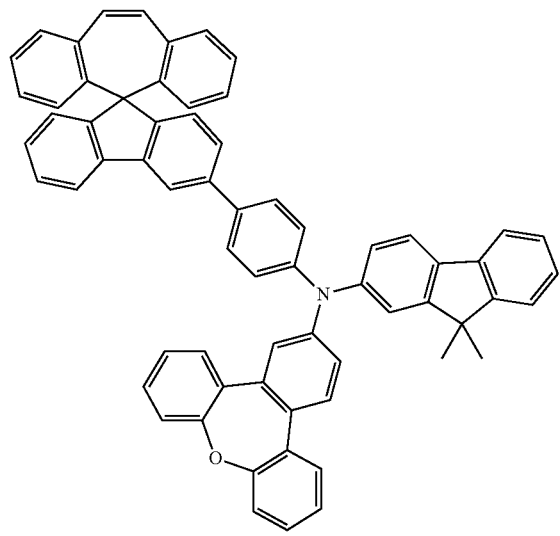
(121)
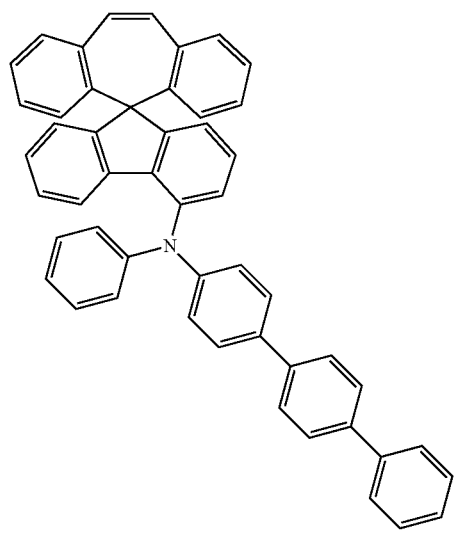
(122)
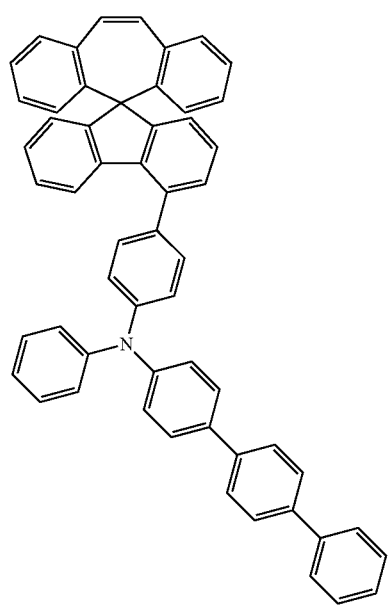
(123)
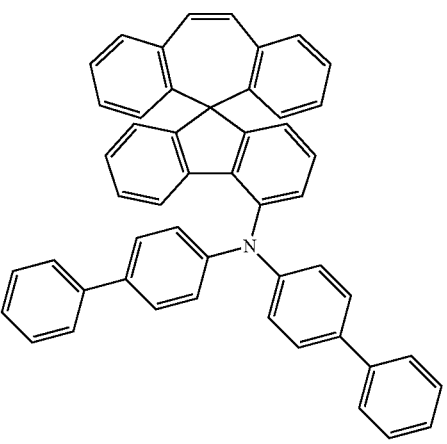
(124)
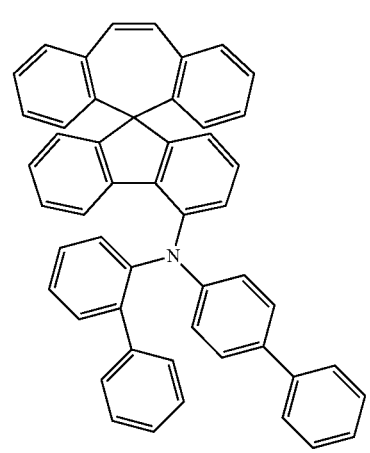
(125)
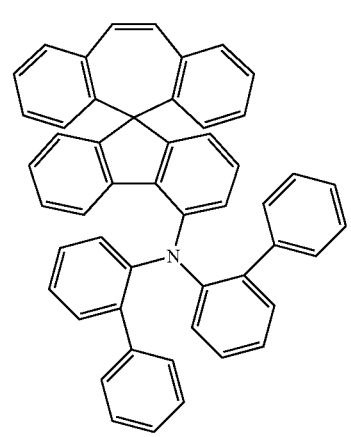

(126)
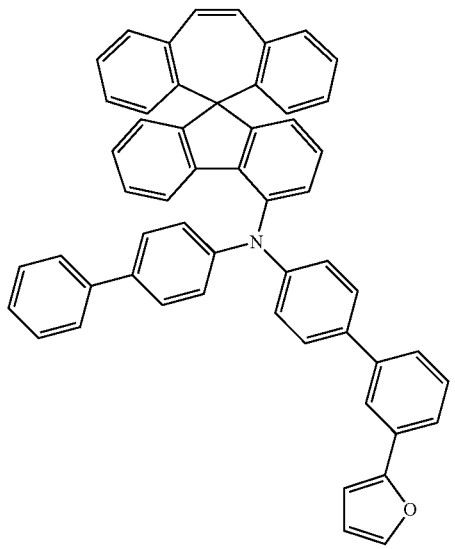
(127)
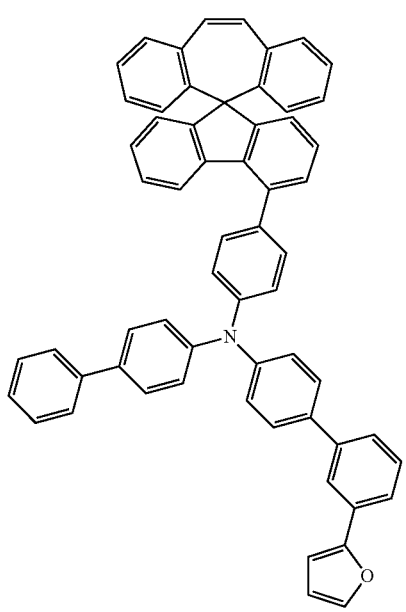
(128)
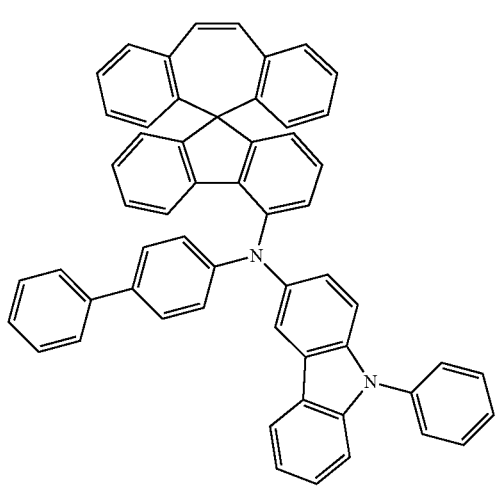
(129)
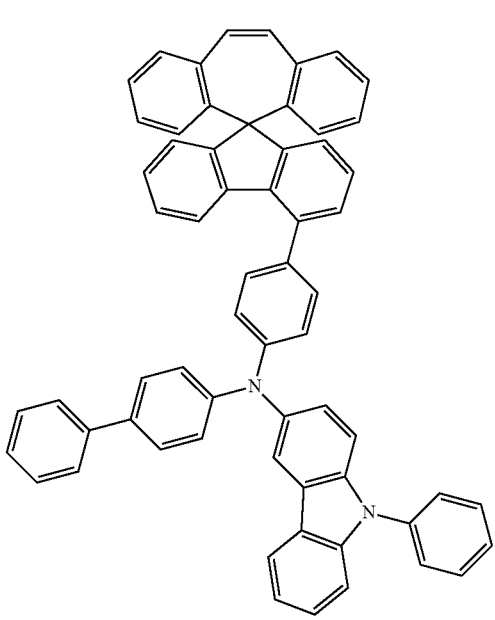
(130)
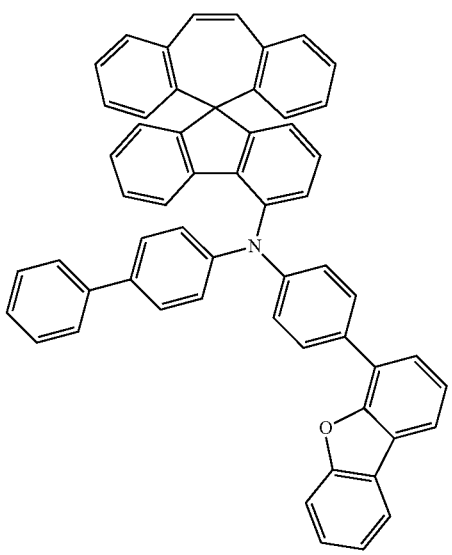

(131)
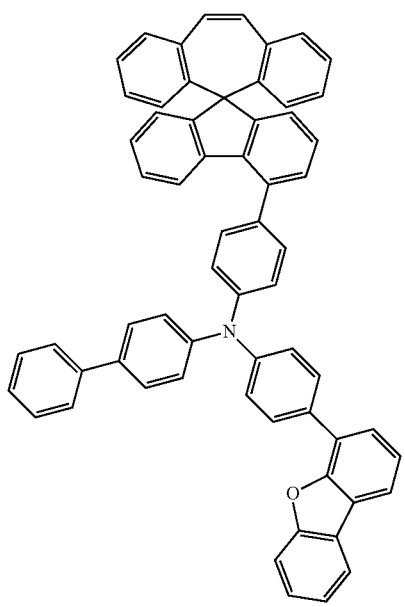
(132)
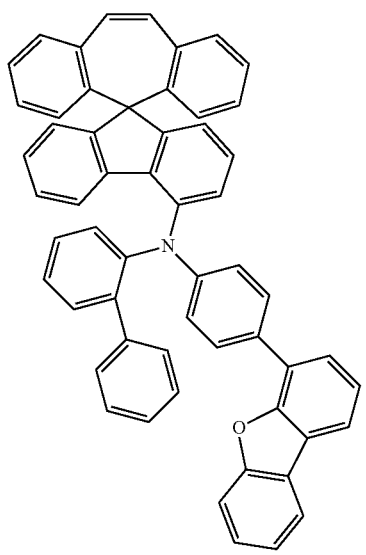
(133)
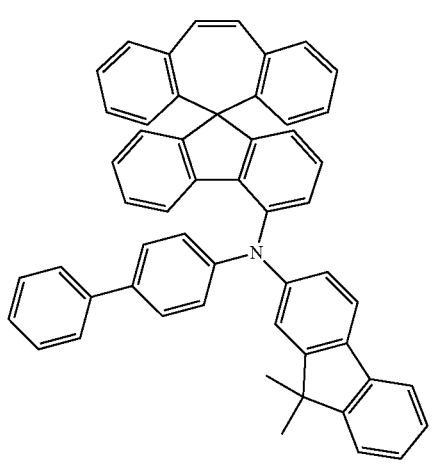
(134)
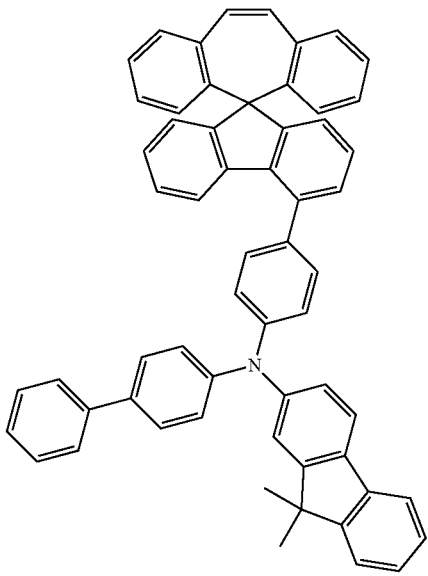
(135)
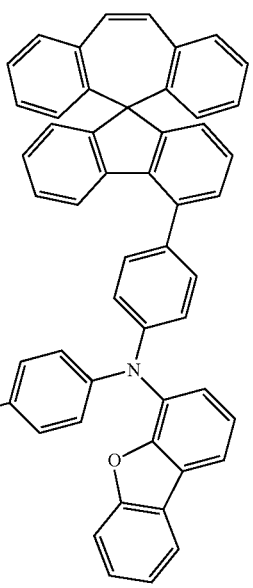
(136)
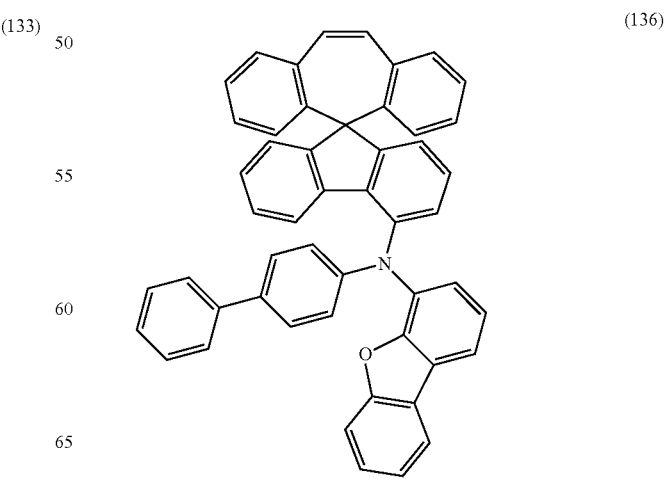

-continued
(137)
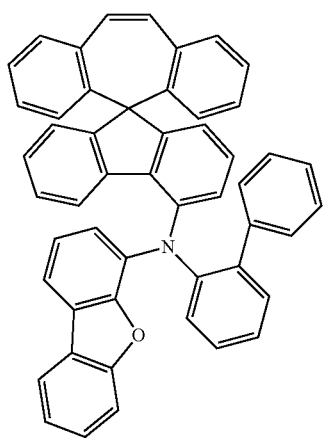
(138)
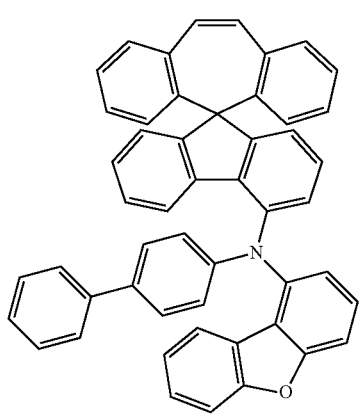
(139)
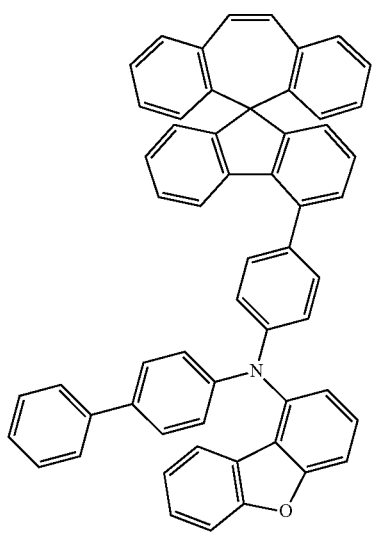
-continued
(140)
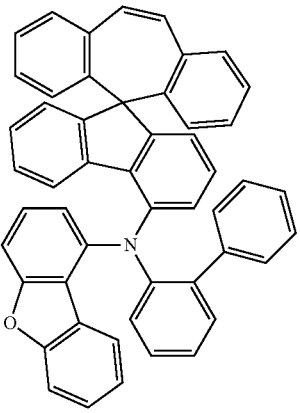
(141)
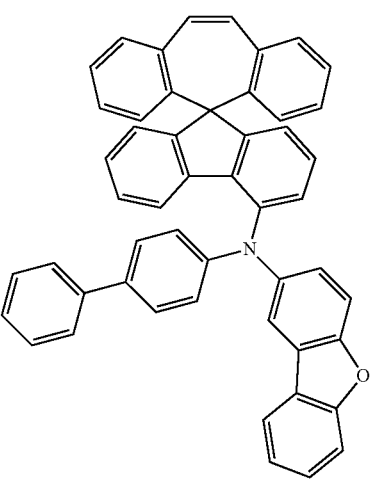
(142)
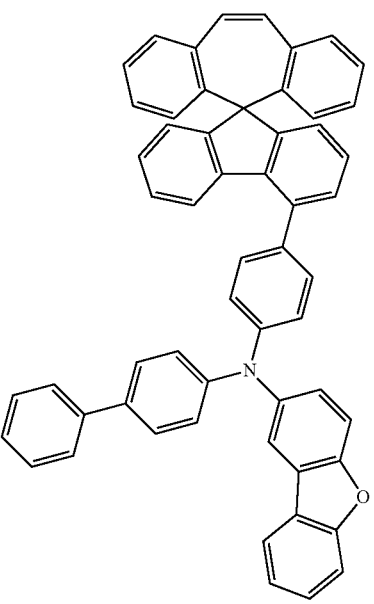

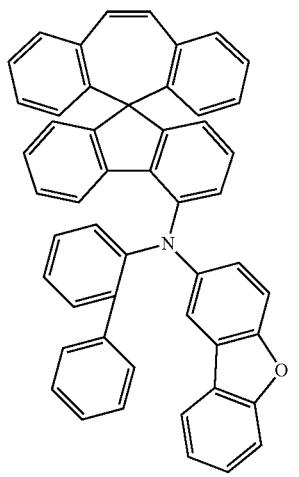
(143)
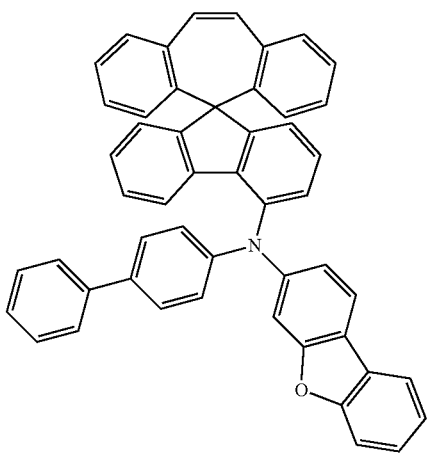
(146)
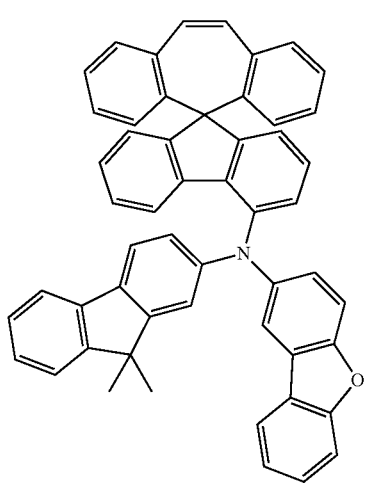
(144)
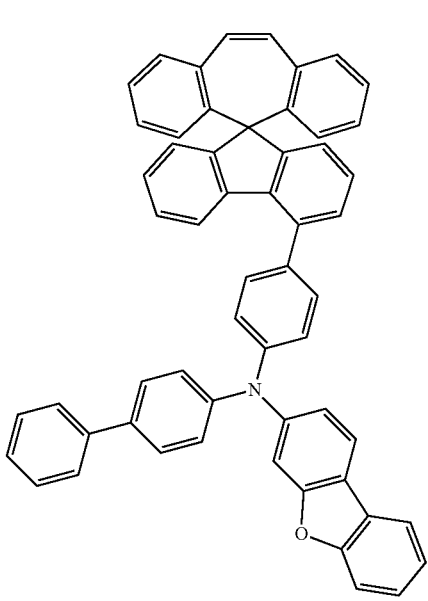
(147)
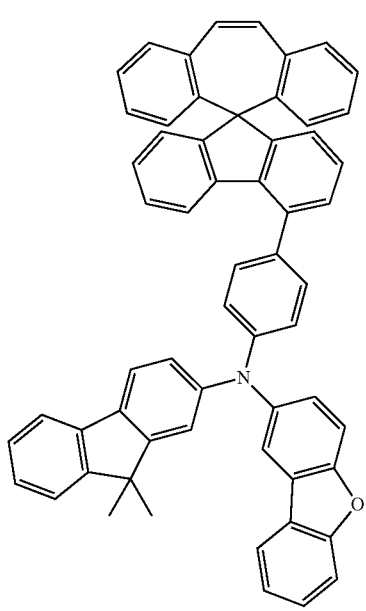
(145)
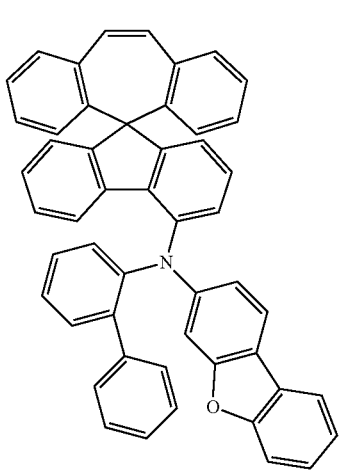
(148)

-continued
(149)
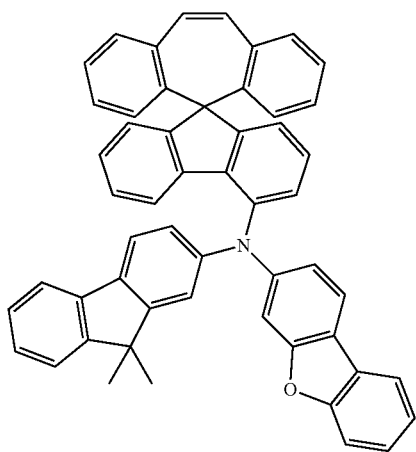
(152)
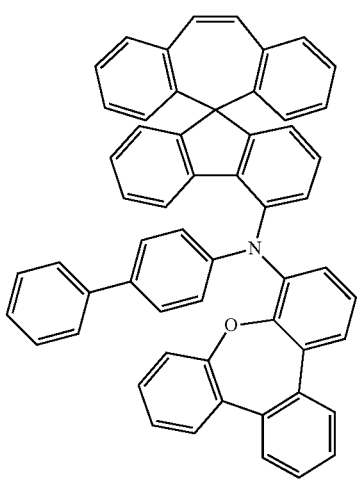
(150)
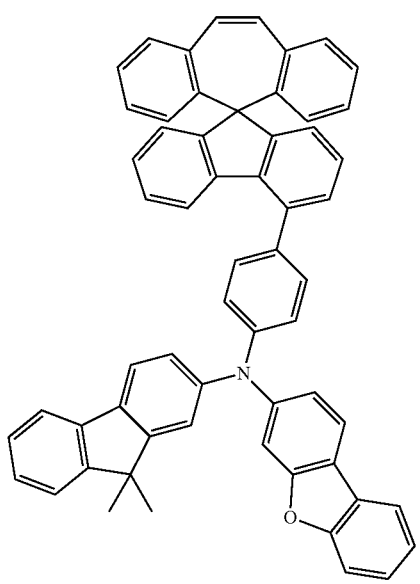
(153)
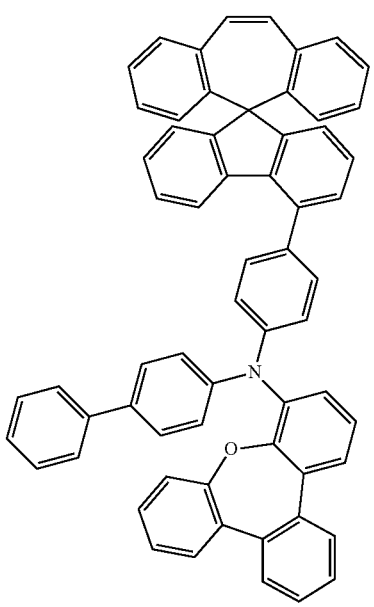
(151)
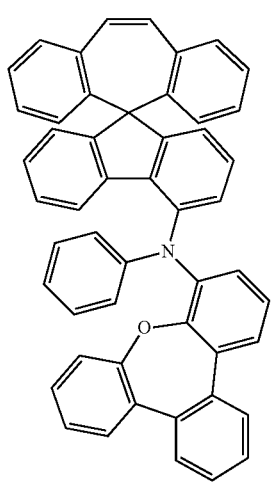
(154)
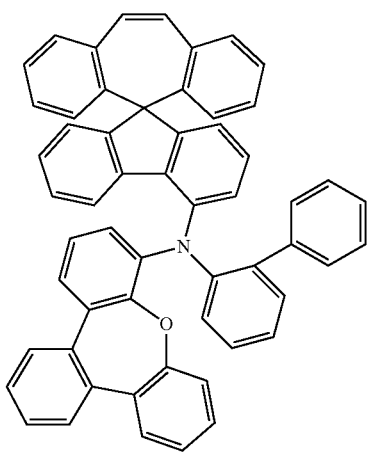

(155)
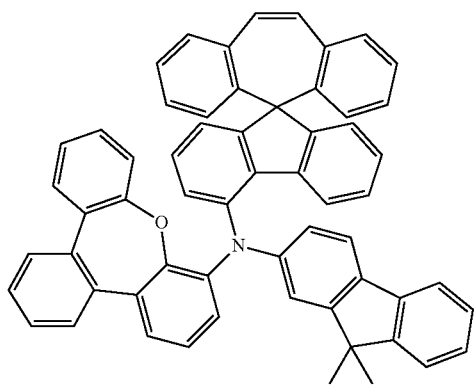
(156)
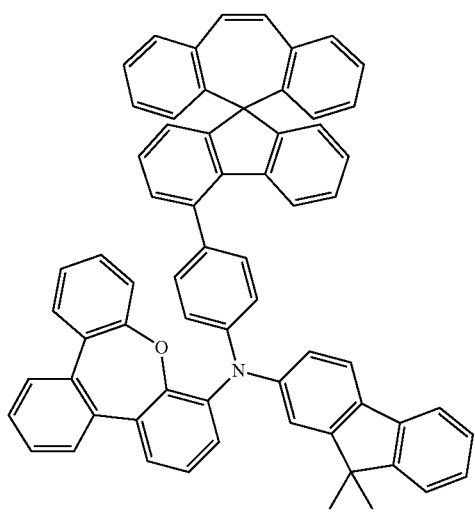
(157)
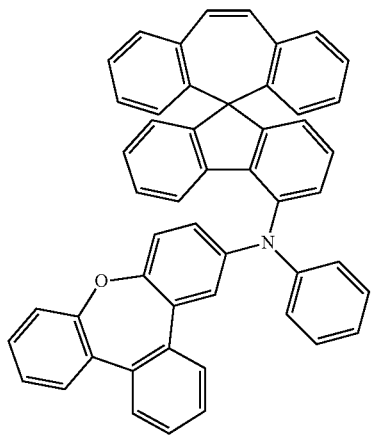
(158)
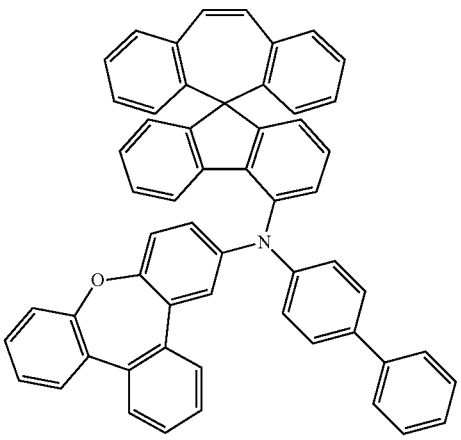
(159)
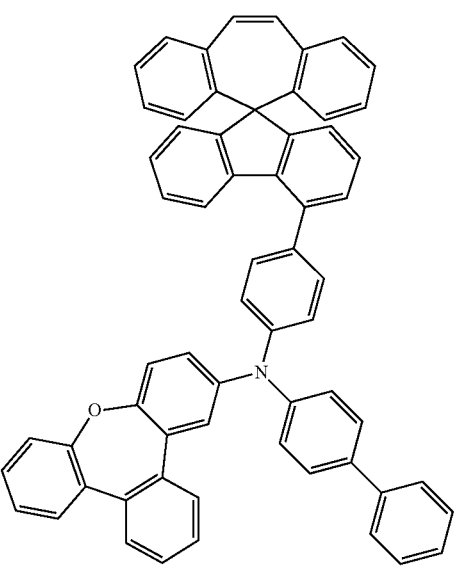
(160)
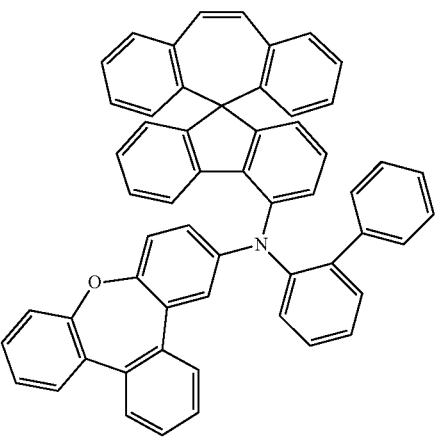

(161)
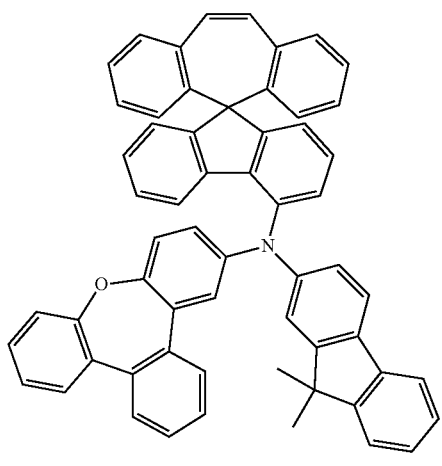
(162)
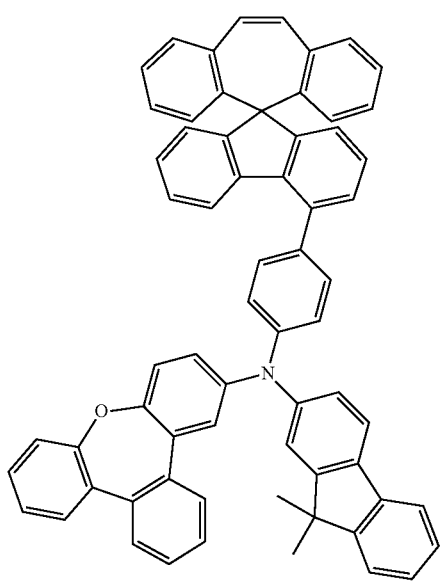
(163)
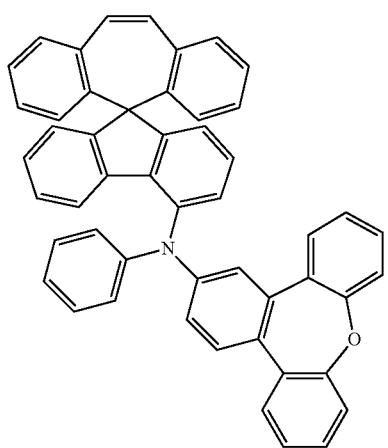
(164)
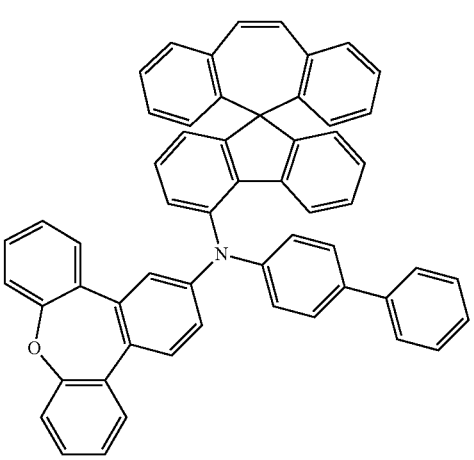
(165)
(166)
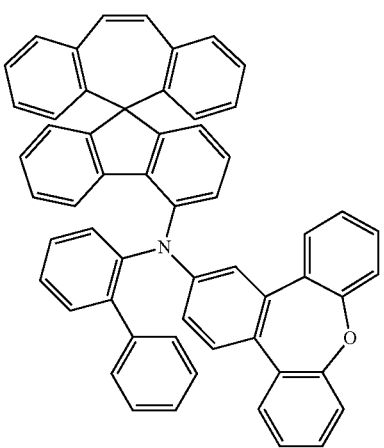

(167)
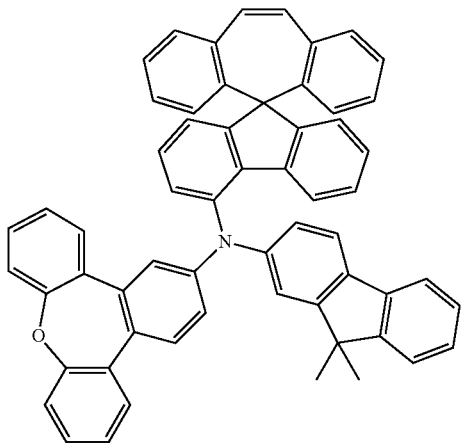
(168)
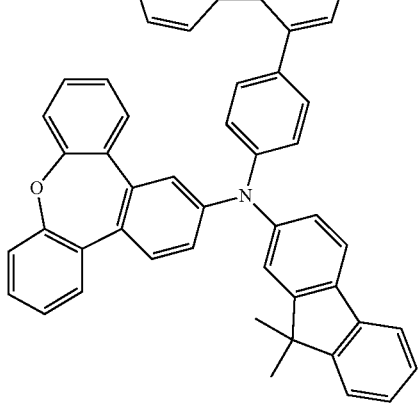
(169)
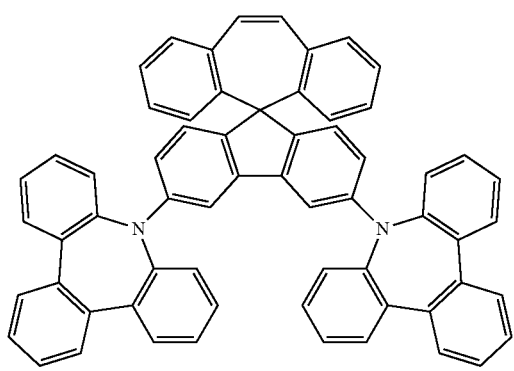
(170)
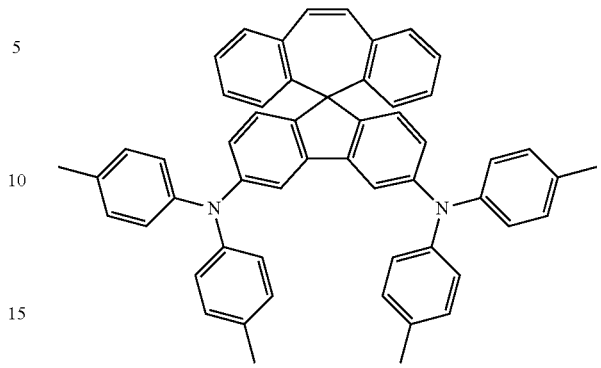
(171)
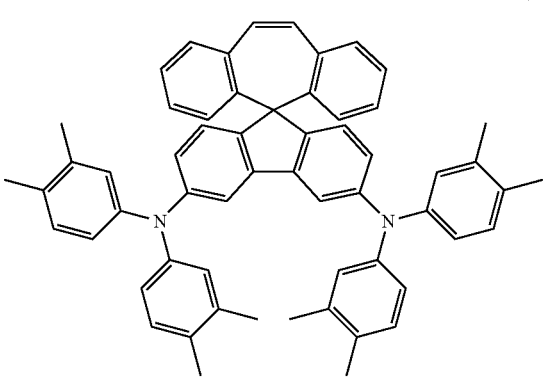
(172)
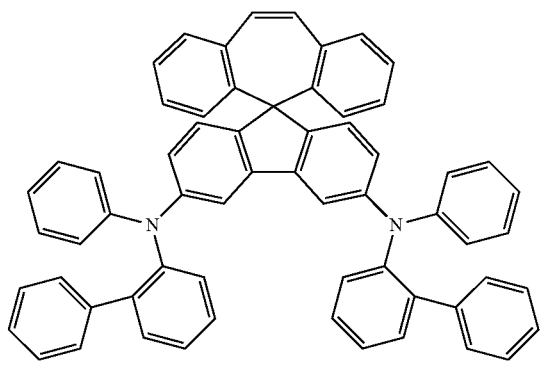
(173)
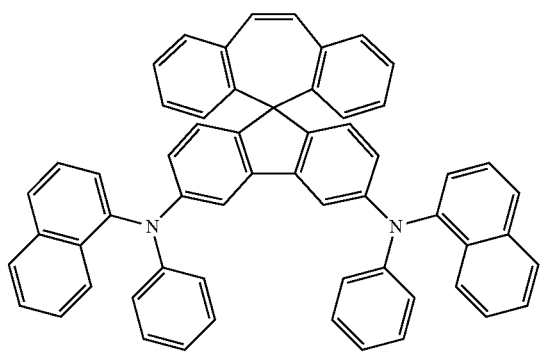

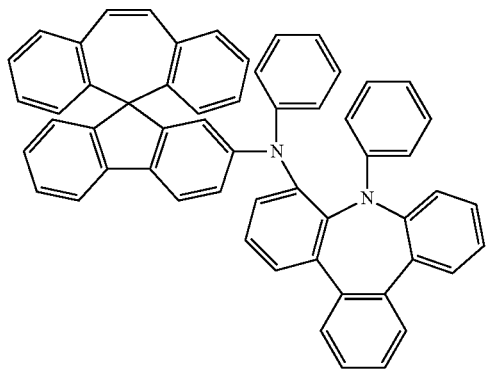
(174)
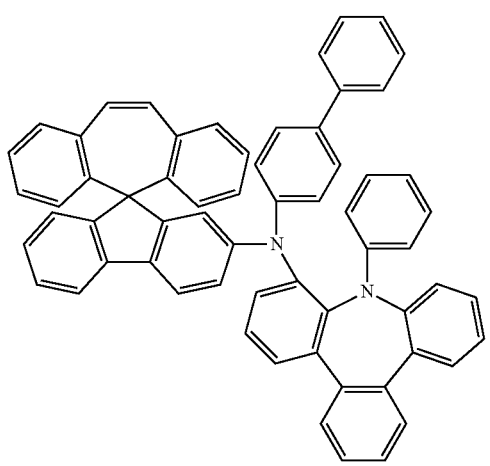
(175)
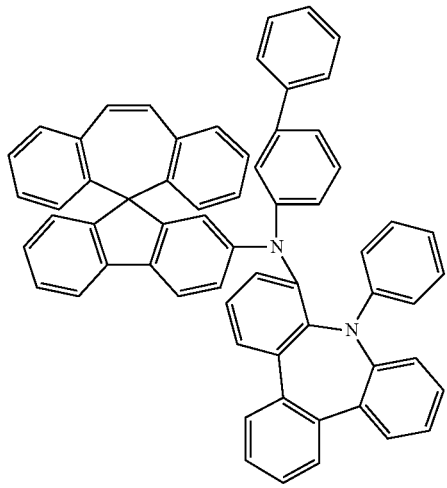
(176)
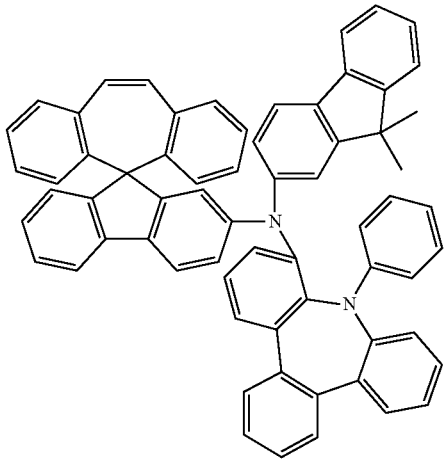
(177)
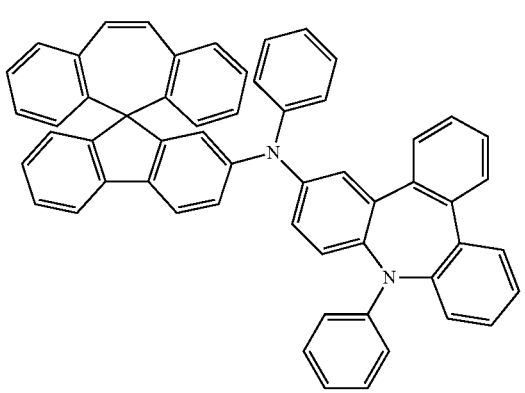
(178)
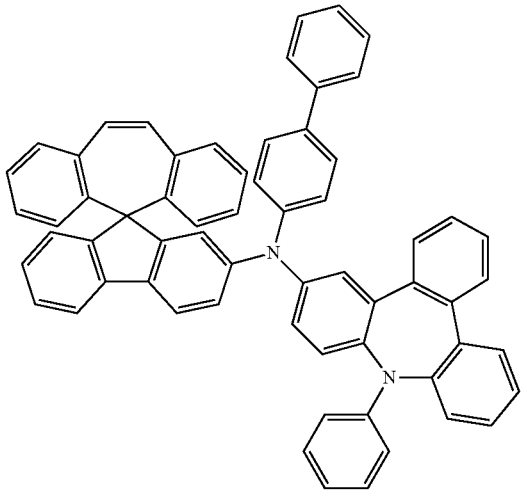
(179)

(180)
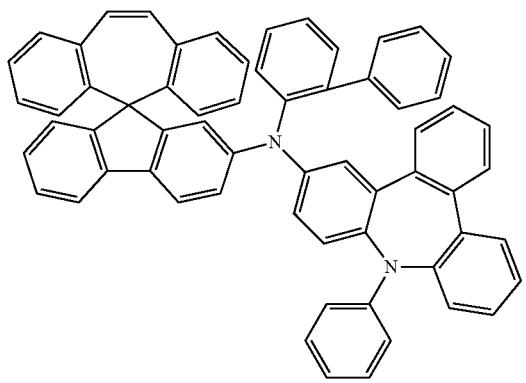
(181)
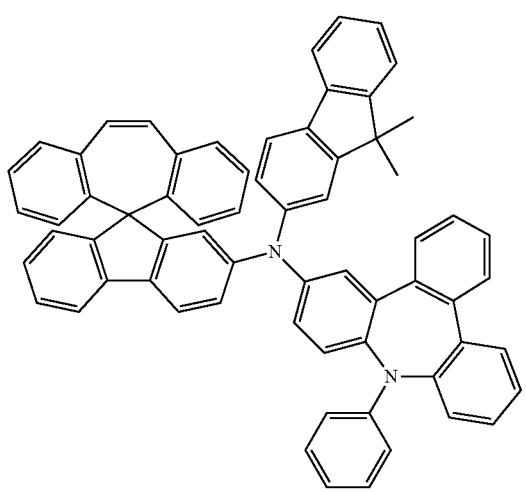
(182)
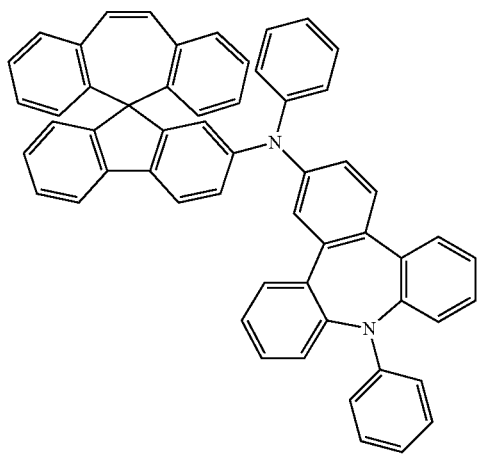
(183)
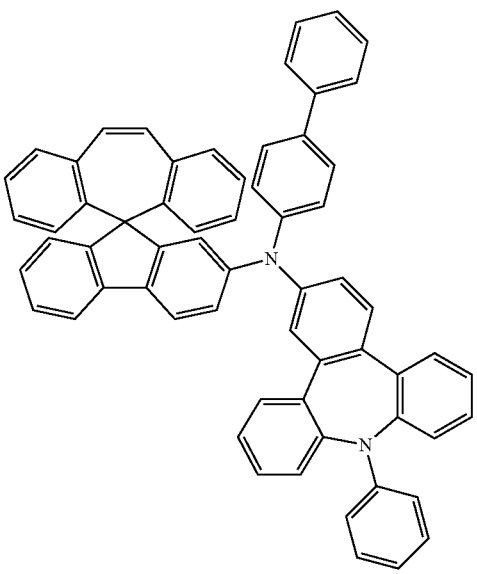
(184)
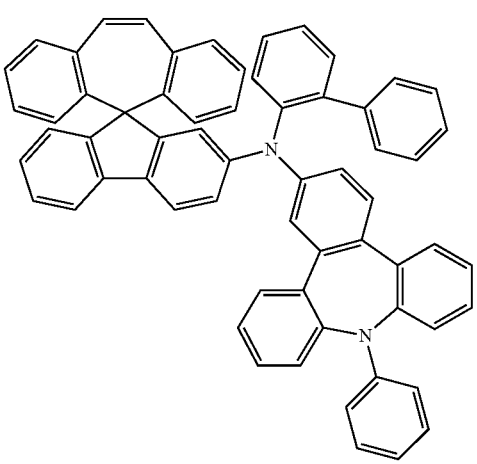
(185)
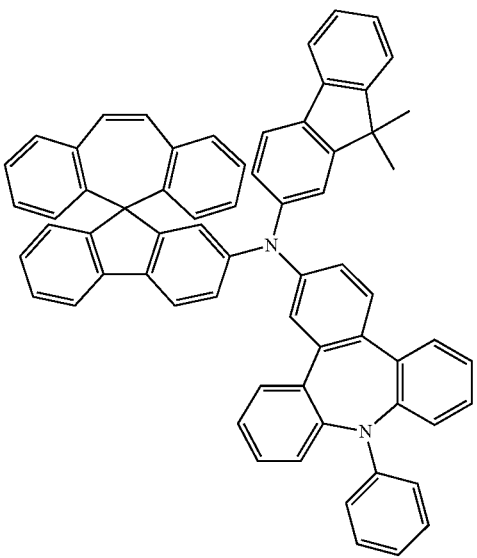

(186)
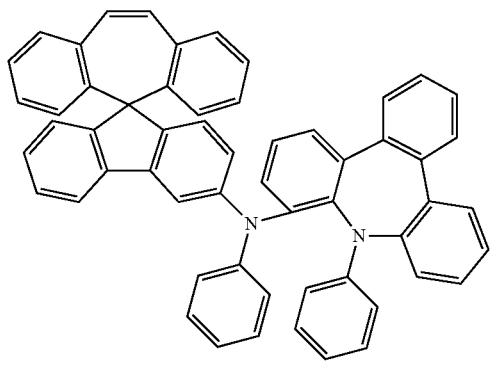
(187)
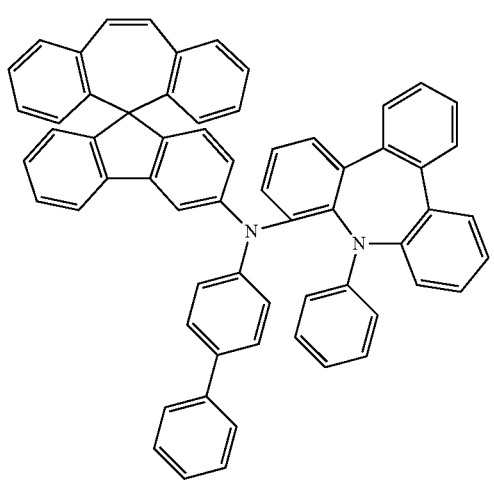
(188)
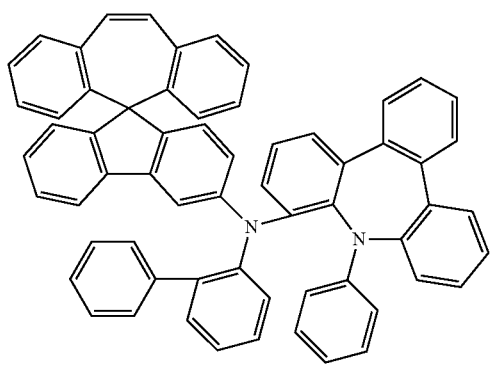
(189)
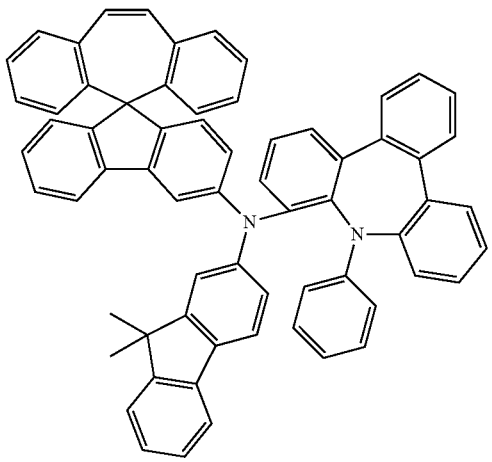
(190)
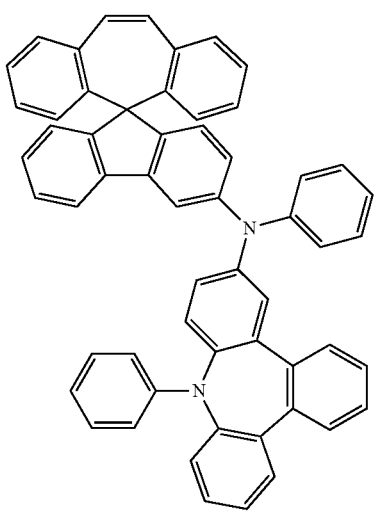
(191)
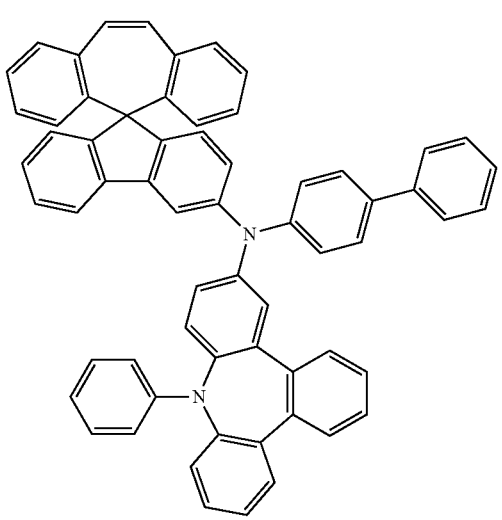

(192)
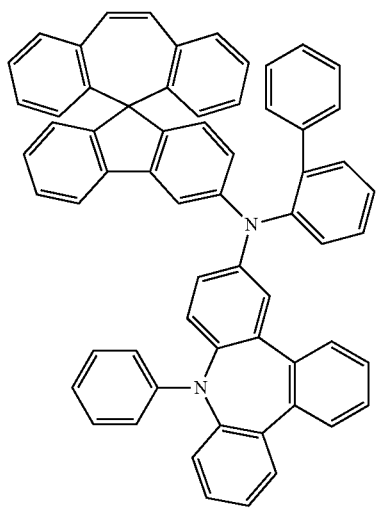
(193)
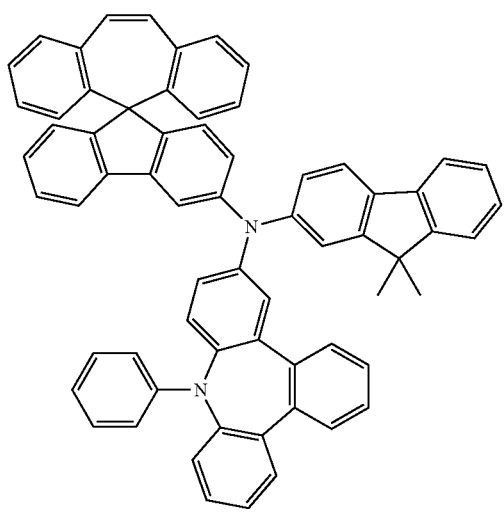
(194)
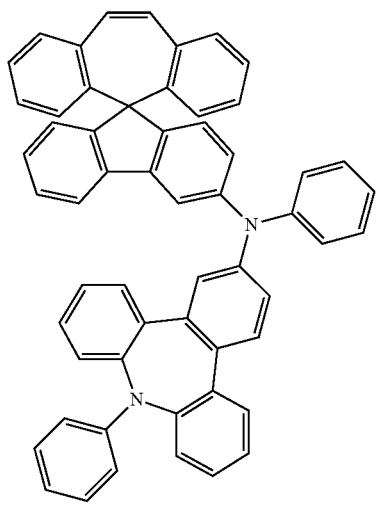
(195)
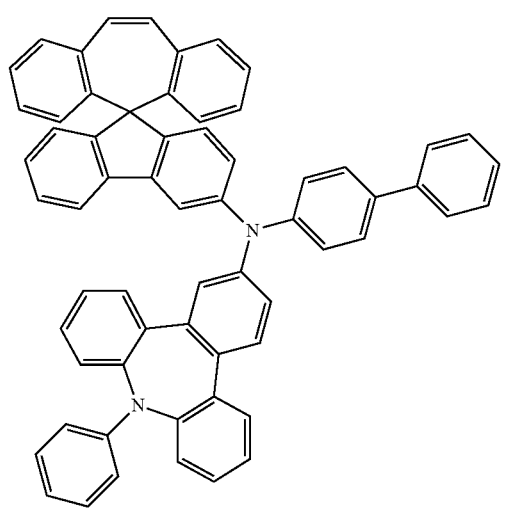
(196)
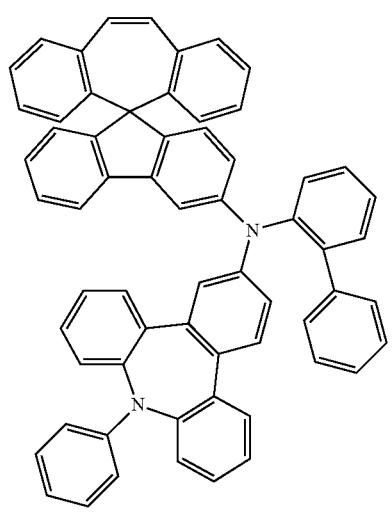
(197)
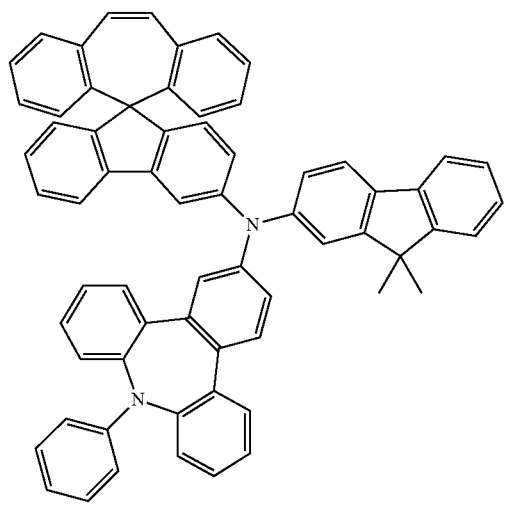

(198)
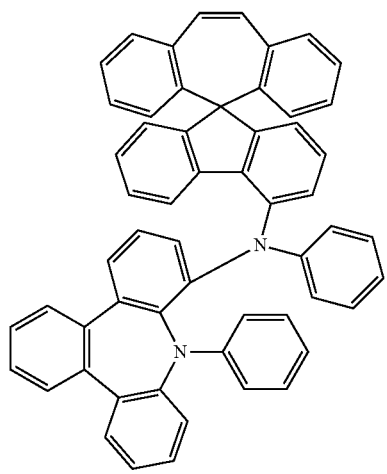
(199)
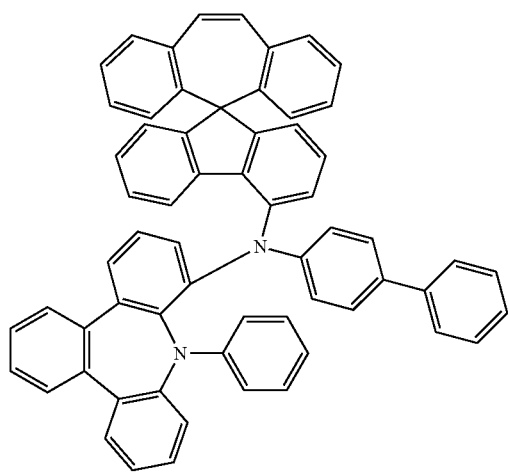
(200)
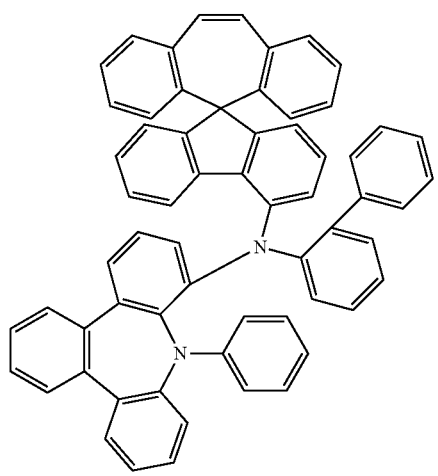
(201)
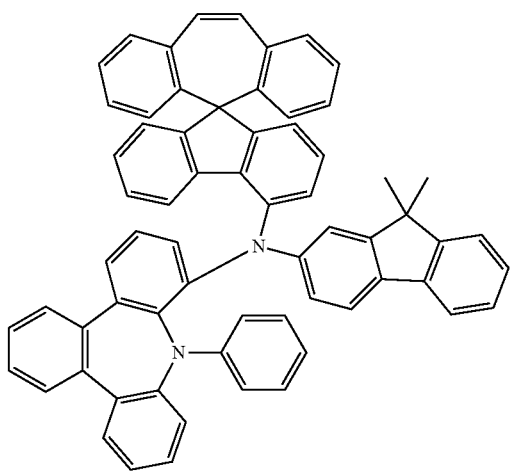
(202)
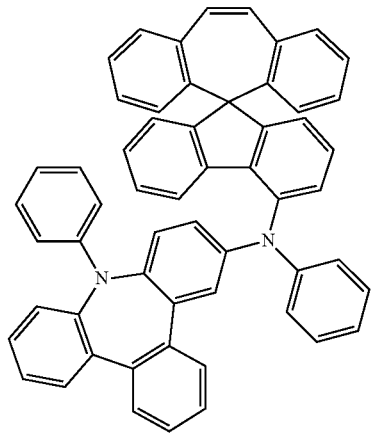
(203)
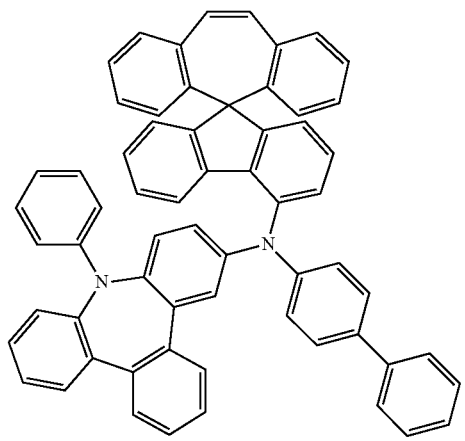

(204)
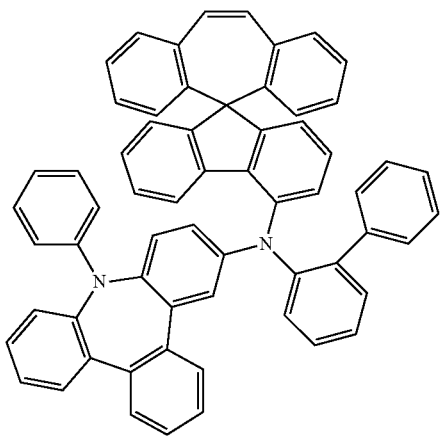
(205)
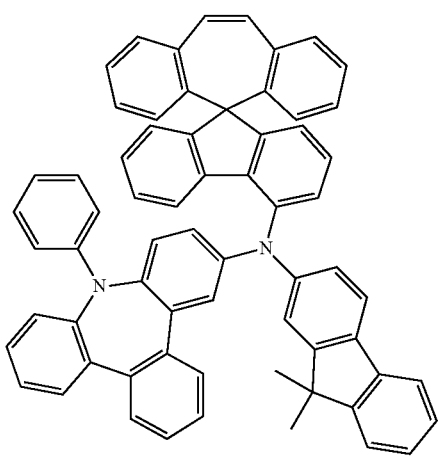
(206)
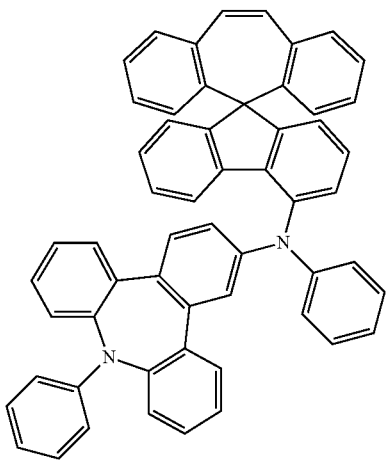
(207)
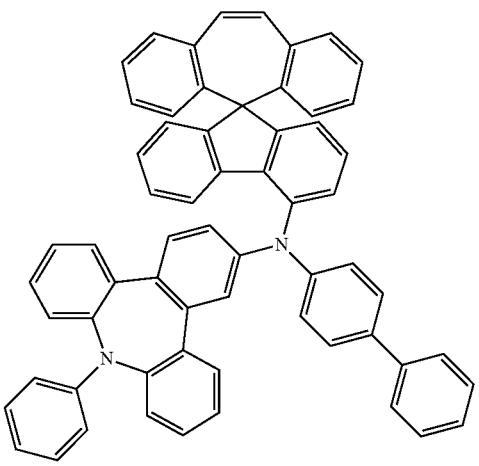
(208)
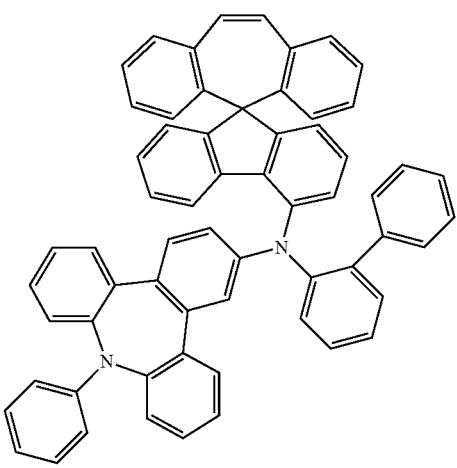
(209)
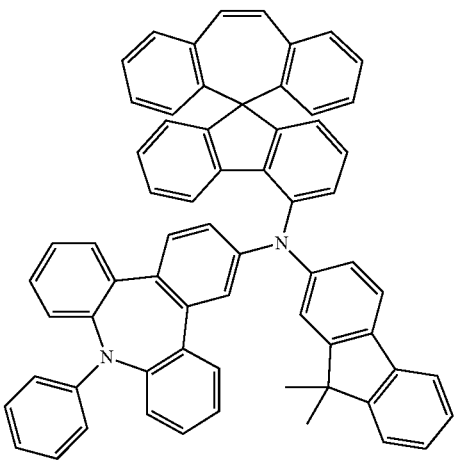

(210)
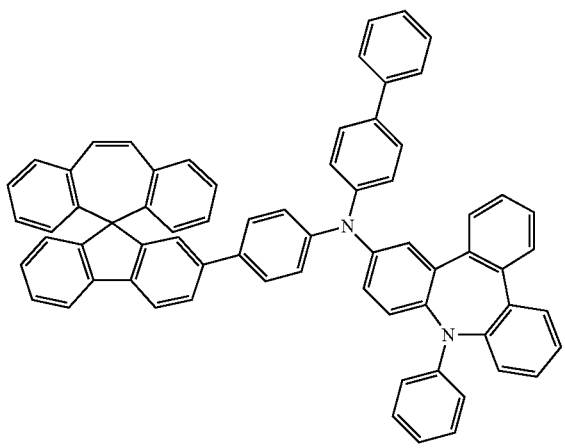

(211)
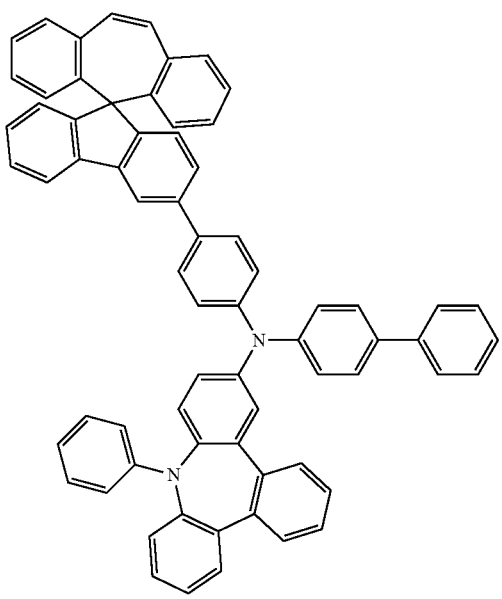

(212)
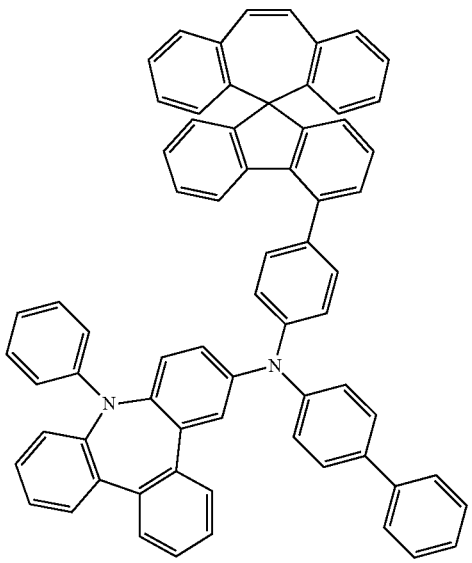

Herein, at least one hydrogen atom of the compounds (1) to (212) can further be optionally substituted with the aforementioned substituents.

Organic Electronic Device

An organic electronic device comprising the aforementioned compounds is also provided in the present disclosure.

In one embodiment, the organic electronic device comprises: a first electrode; a second electrode; and an organic layer disposed between the first electrode and the second electrode, wherein the organic layer comprises any one of the aforementioned compounds.

Herein, the term "organic layer" refers to single layer or multilayers disposed between the first electrode and the second electrode of the organic electronic device.

The application of the organic electronic device of the present disclosure comprises, but is not limited to, an organic light emitting device, an organic solar cell device, an organic thin film transistor, an organic photodetector, a flat panel display, a computer monitor, a television, a billboard, a light for interior or exterior illumination, a light for interior or exterior signaling, a heads up display, a fully transparent display, a flexible display, a laser printer, a telephone, a cell phone, a tablet computer, a laptop computer, a digital camera, a camcorder, a viewfinder, a micro-display, a vehicle, a large area wall, a theater or stadium screen, or a sign. Preferably, the organic electronic device of the present disclosure is applied to an organic light emitting device, or an organic solar cell device.

Figure 2:
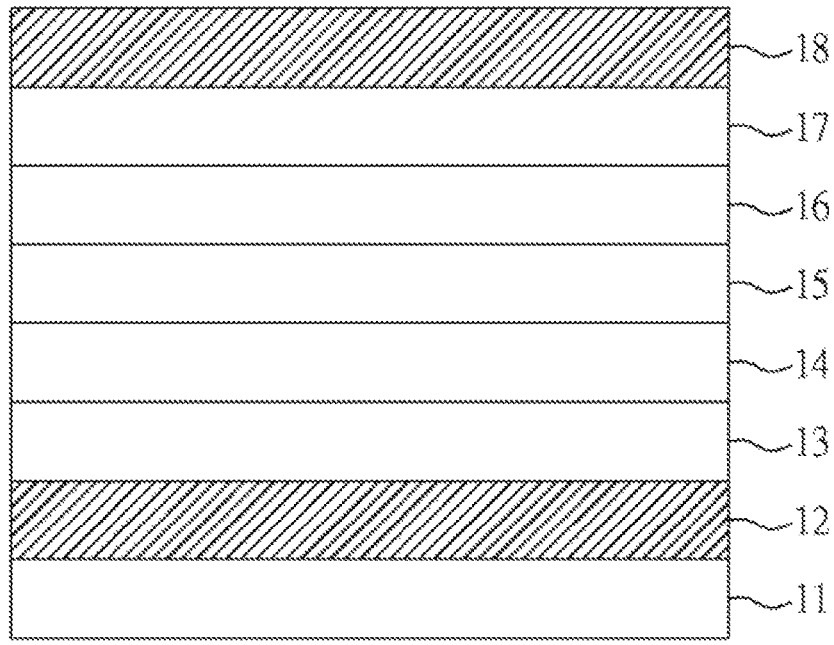
FIG. 2 is a perspective view showing an OLED device of the present invention.

In one embodiment, the organic electronic device can be an organic light emitting device. FIG. 2 is a perspective view showing an exemplary structure of an organic light emitting device capable of using in one embodiment of the present disclosure. As shown in FIG. 2, the organic light emitting device comprises: a substrate 11; an anode 12; a cathode 18; and an organic layer comprising a hole injection layer 13, a hole transporting layer 14, a light emitting layer 15, an electron transporting layer 16 and an electron injection layer 17. However, the present disclosure is not limited thereto. Other layers capable of improving the luminous efficiency of the organic light emitting device, for example an electron blocking layer or a hole blocking layer, can also be formed in the organic light emitting device of the present disclosure. When the organic light emitting device of the present disclosure further comprises the electron blocking layer, the electron blocking layer can be disposed between the hole transporting layer 14 and the light emitting layer 15. When the organic light emitting device of the present disclosure further comprises the hole blocking layer, the hole blocking layer can be disposed between the electron transporting layer 16 and the light emitting layer 15.

In one embodiment, the organic light emitting device of the present disclosure may include a hole transporting layer, which comprises the aforesaid compounds. In another embodiment, the organic light emitting device of the present disclosure may include a hole injection layer, which comprises the aforesaid compounds. In further another embodiment, the organic light emitting device of the present disclosure may include an electron blocking layer, which comprises the aforesaid compounds. However, the present disclosure is not limited thereto.

In one embodiment, the light emitting layer may contain a phosphorescent light emitting material which may comprise iridium or platinum. In another embodiment, the light emitting layer may contain a quantum dots or semiconductor nanocrystal materials. However, the present disclosure is not limited thereto.

Figure 3:
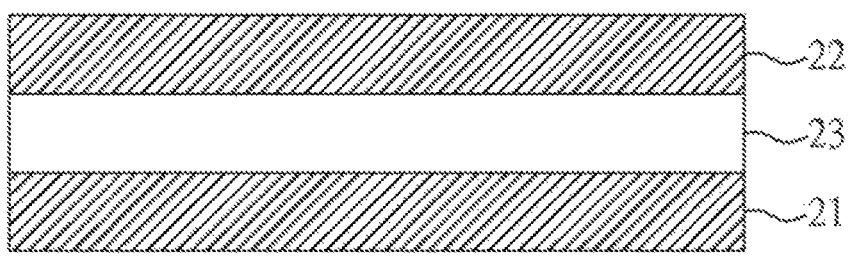
FIG. 3 is a perspective view showing an organic solar cell device of the present invention.
Figure 4:
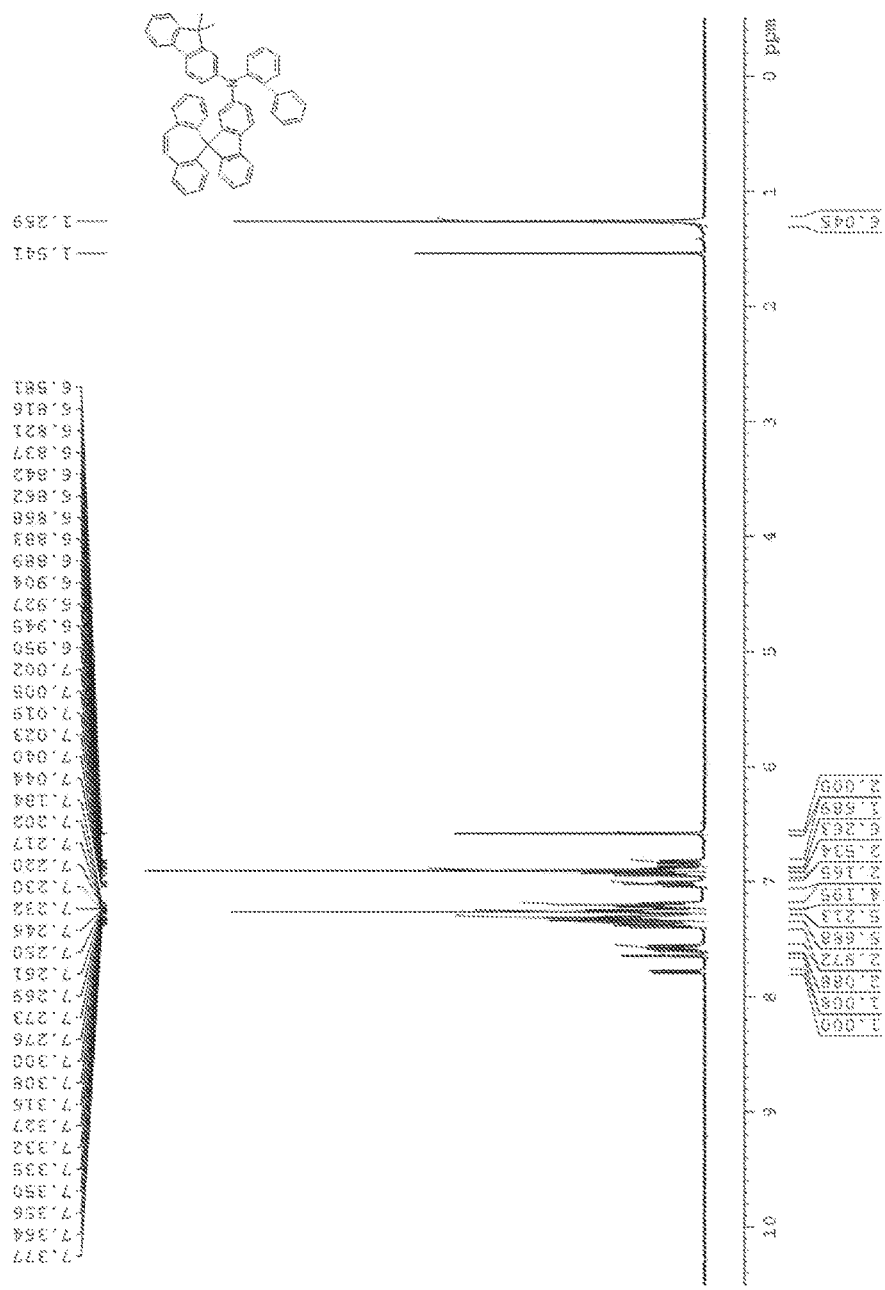
FIG. 4 is 1H NMR data of Compound (1) (SGM 058) of the present disclosure.
Figure 5:
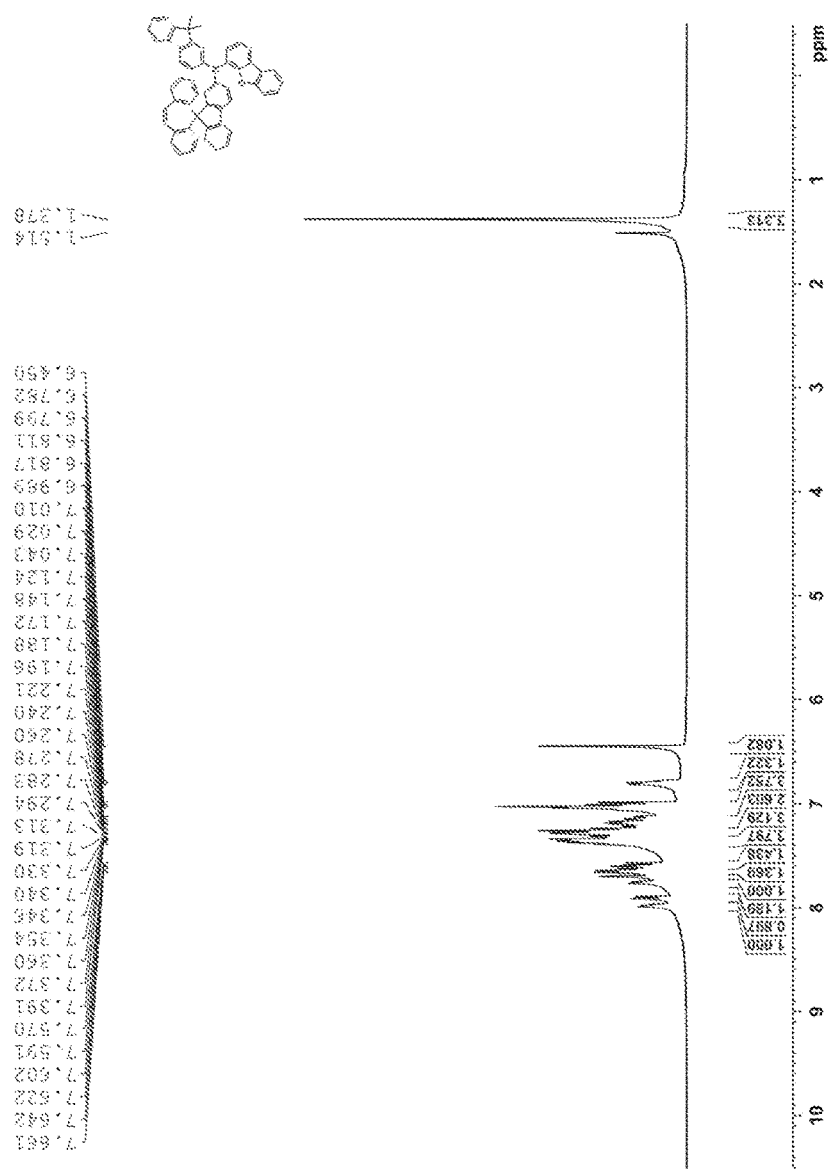
FIG. 5 is 1H NMR data of Compound (2) (SGM 430) of the present disclosure.
Figure 6:
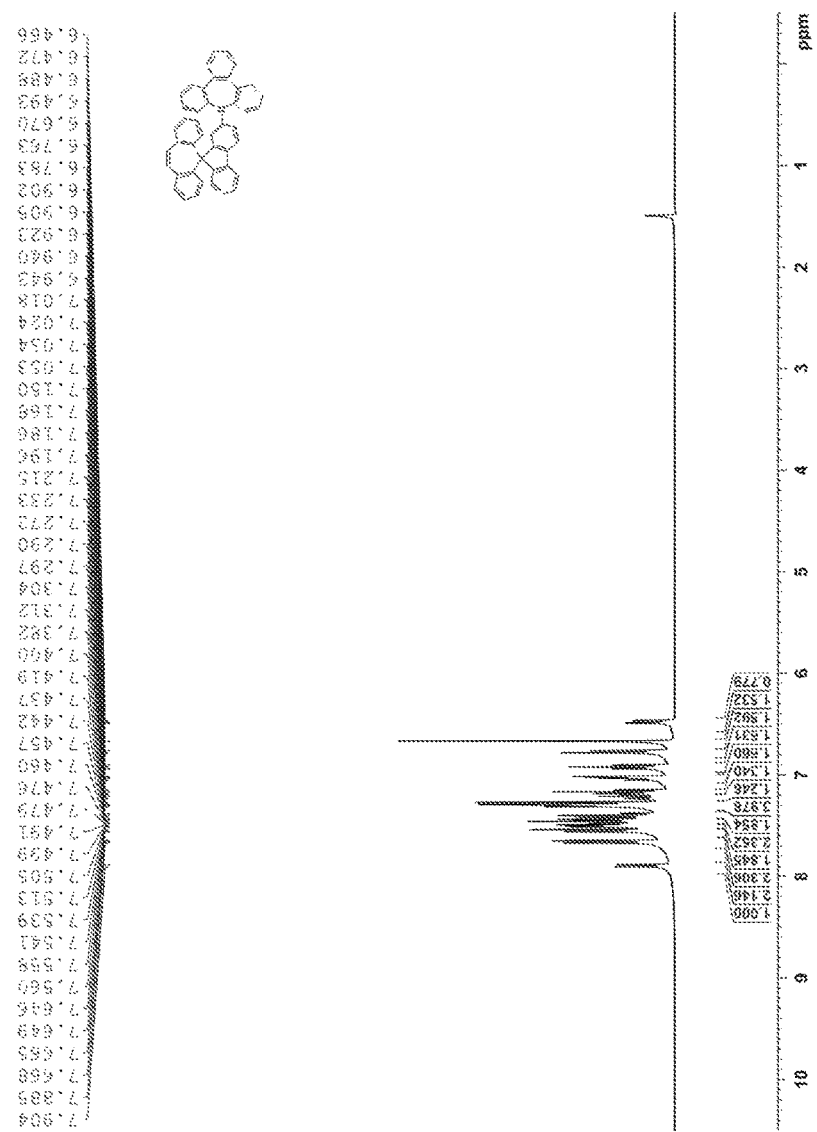
FIG. 6 is 1H NMR data of Compound (4) (SGM 435) of the present disclosure.
Figure 7:
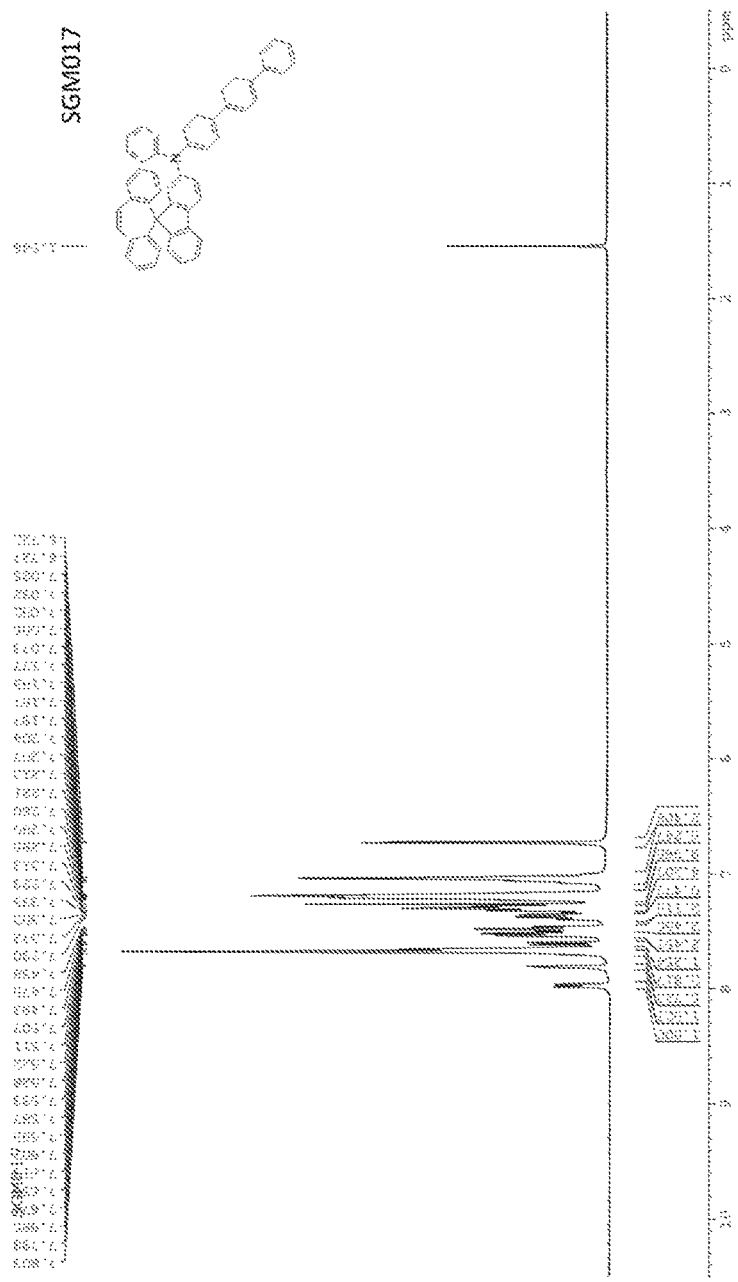
FIG. 7 is 1H NMR data of Compound (5) (SGM 017) of the present disclosure.
Figure 8:
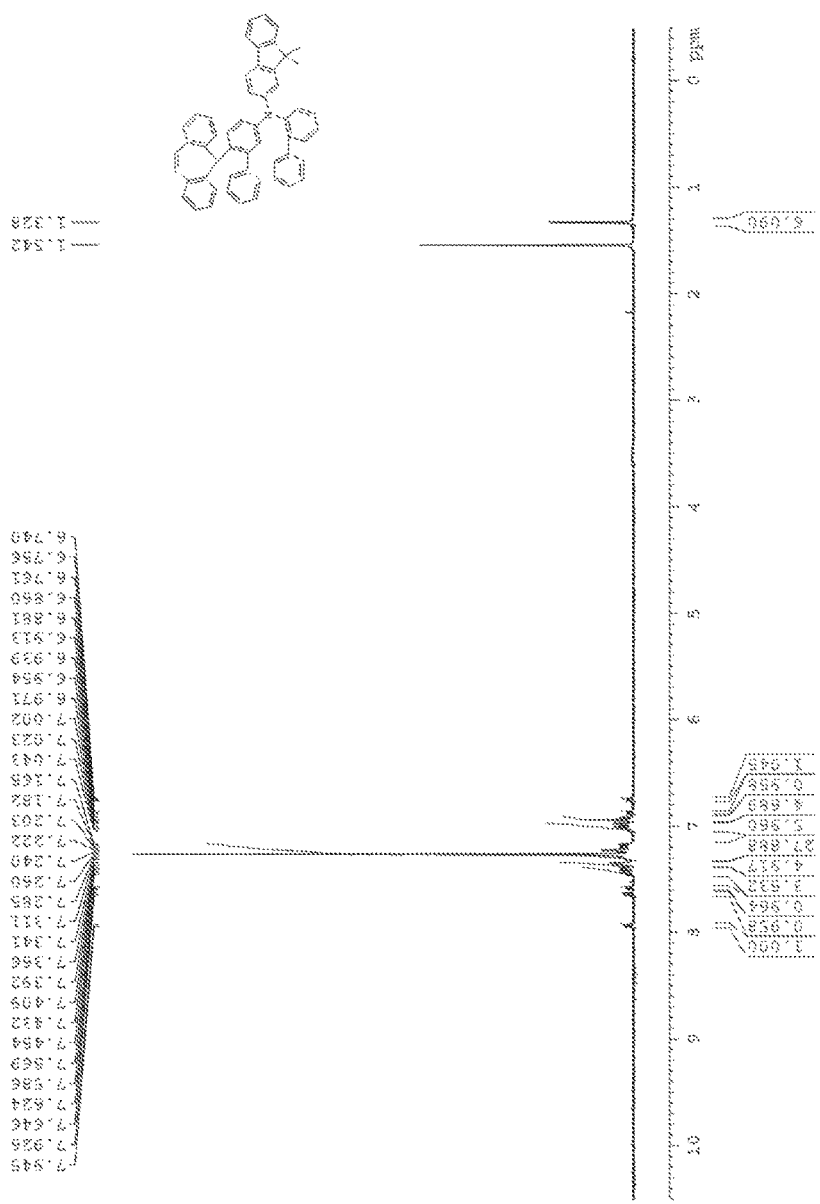
FIG. 8 is 1H NMR data of Compound (6) (SGM 053) of the present disclosure.
Figure 9:
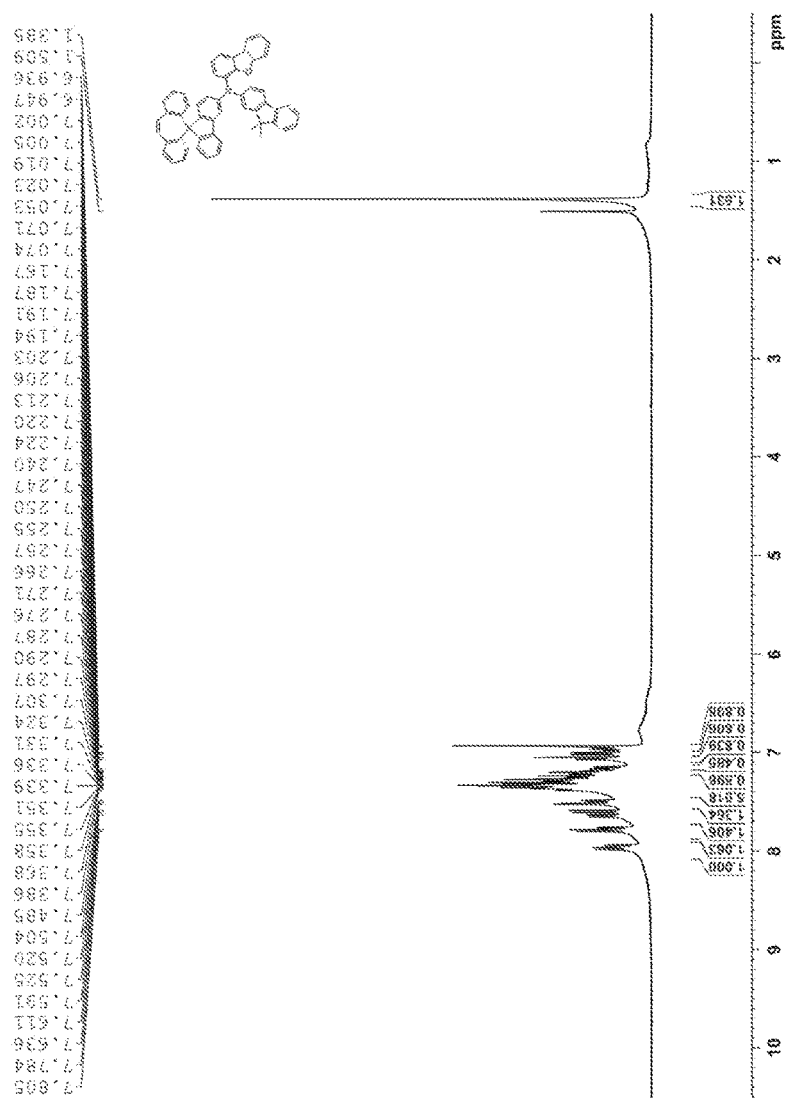
FIG. 9 is 1H NMR data of Compound (7) (SGM 428) of the present disclosure.
Figure 10:
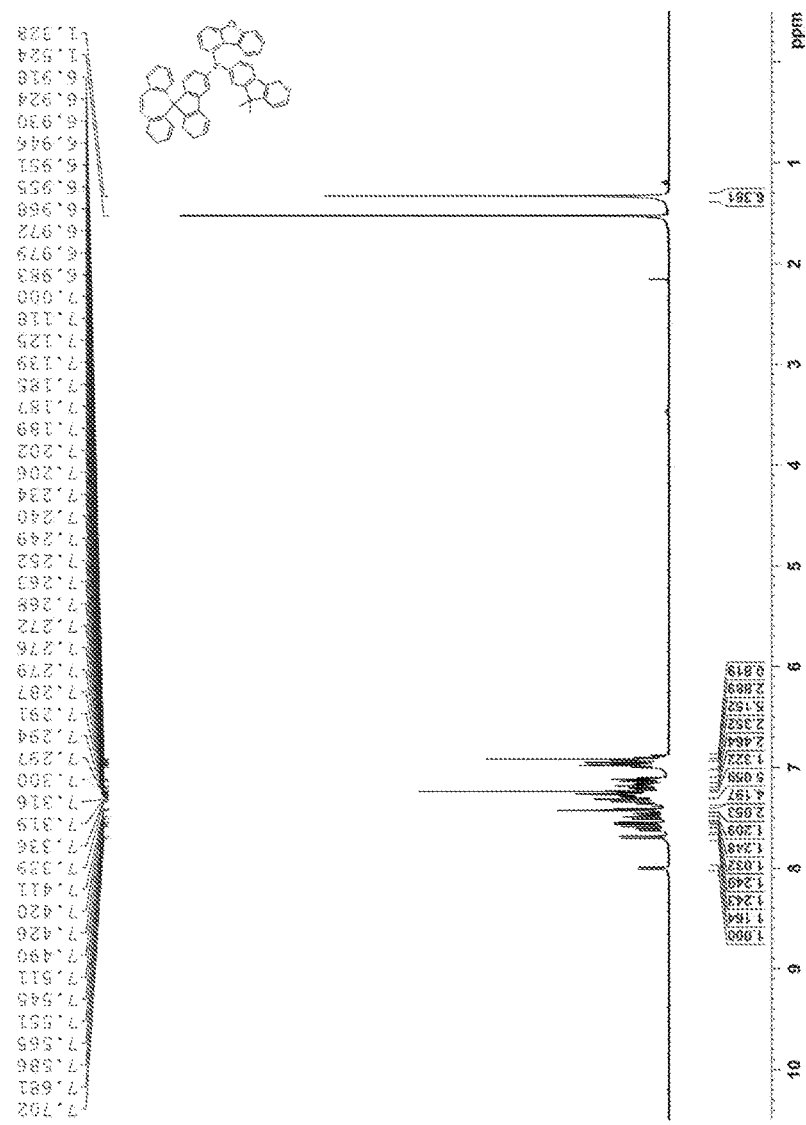
FIG. 10 is 1H NMR data of Compound (8) (SGM 429) of the present disclosure.
Figure 11:
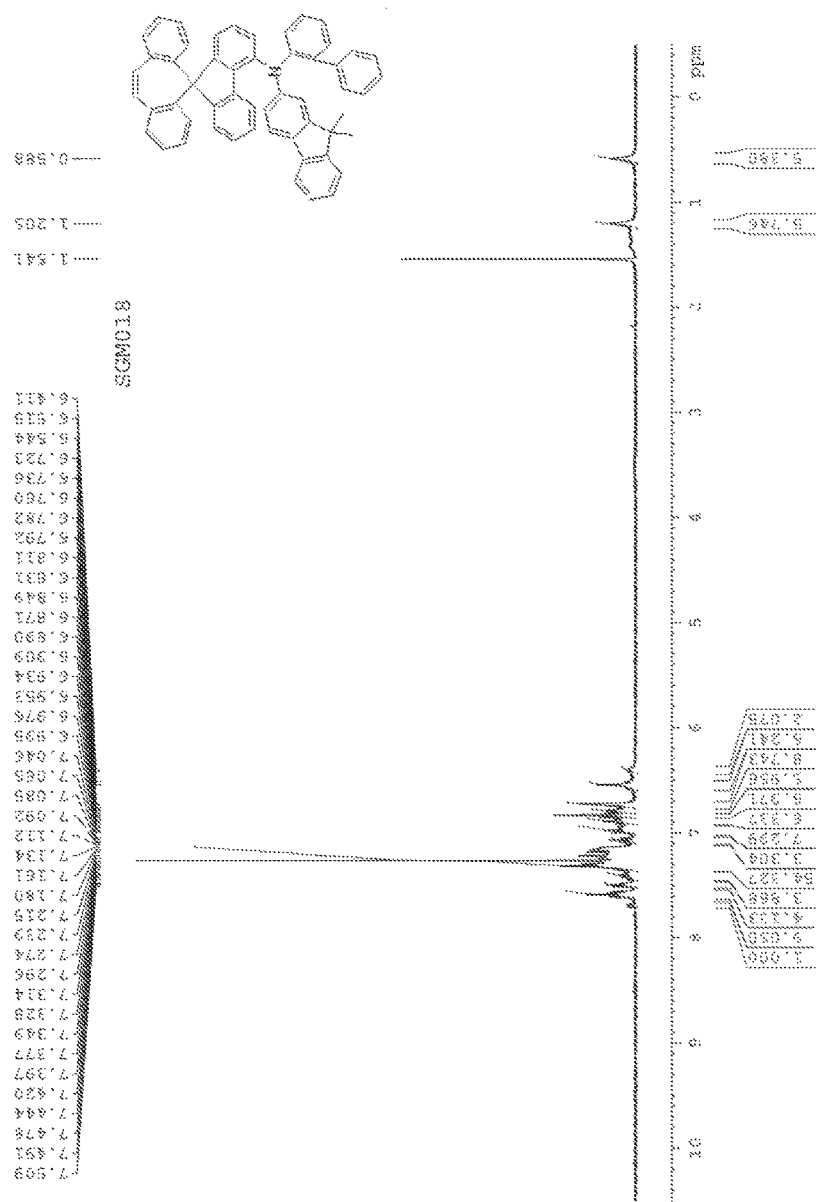
FIG. 11 is 1H NMR data of Compound (10) (SGM 018) of the present disclosure.
Figure 12:
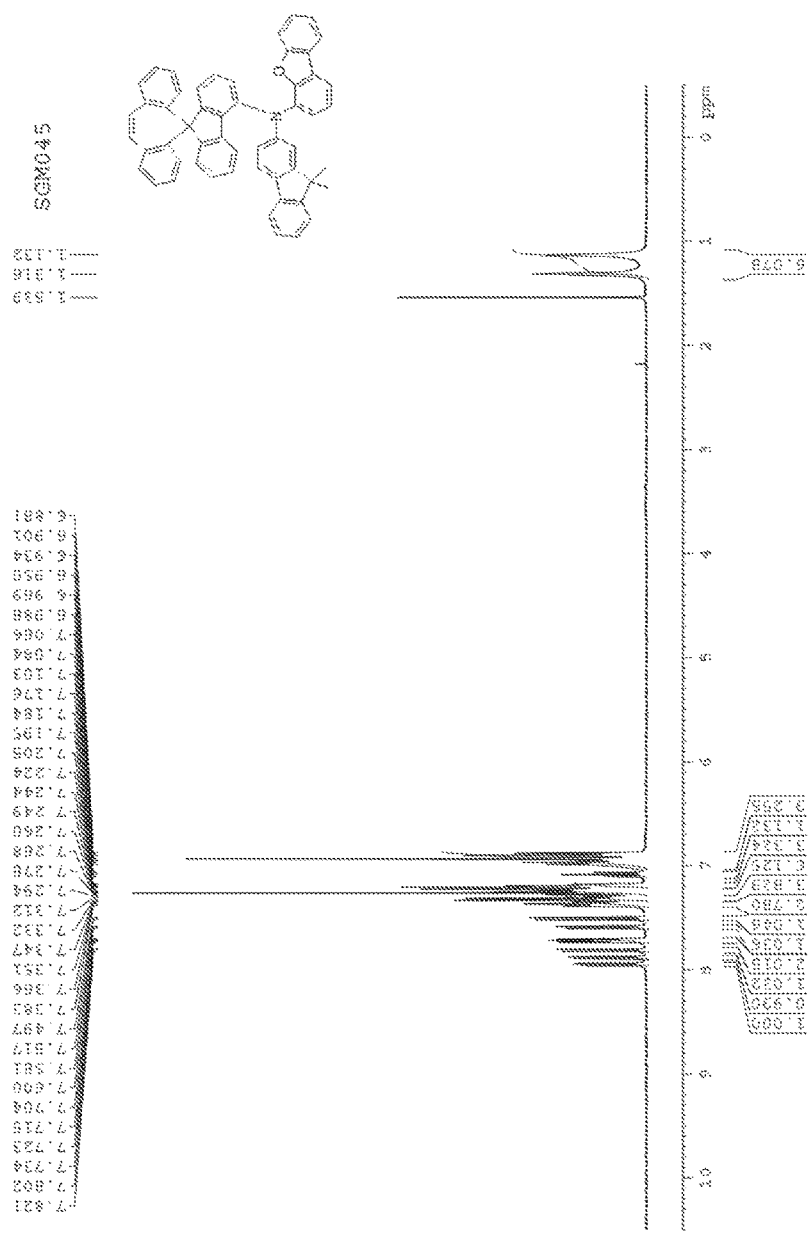
FIG. 12 is 1H NMR data of Compound (11) (SGM 045) of the present disclosure.
Figure 13:
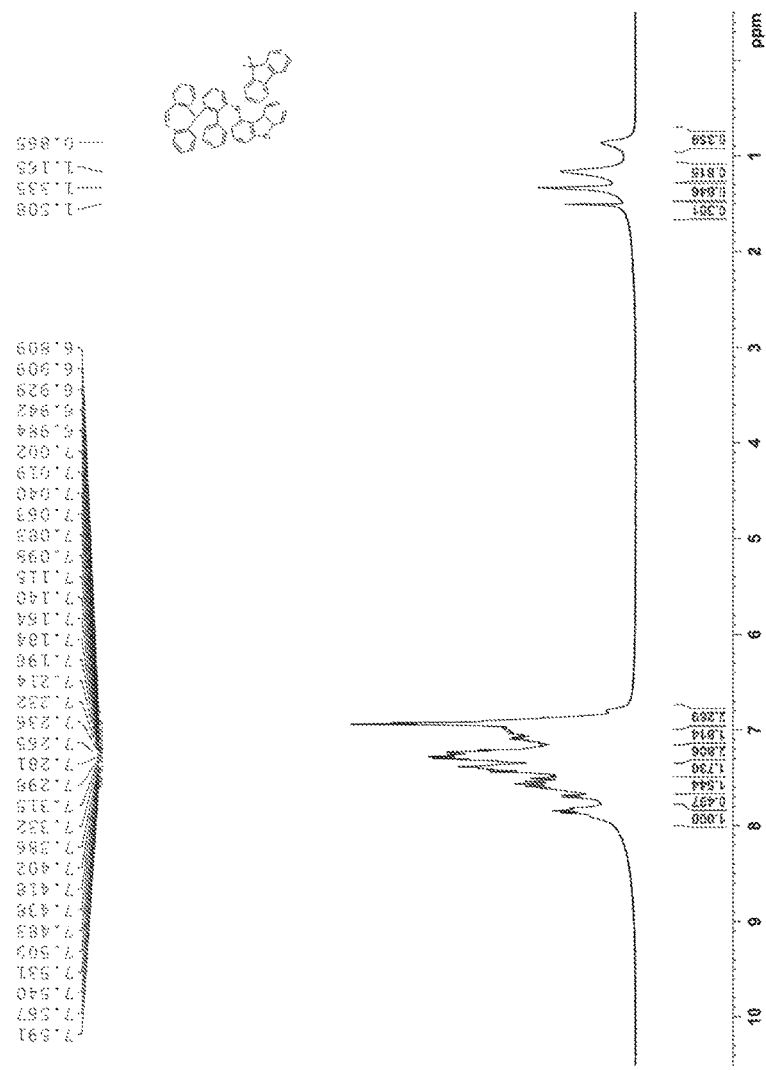
FIG. 13 is 1H NMR data of Compound (12) (SGM 432) of the present disclosure.
Figure 14:
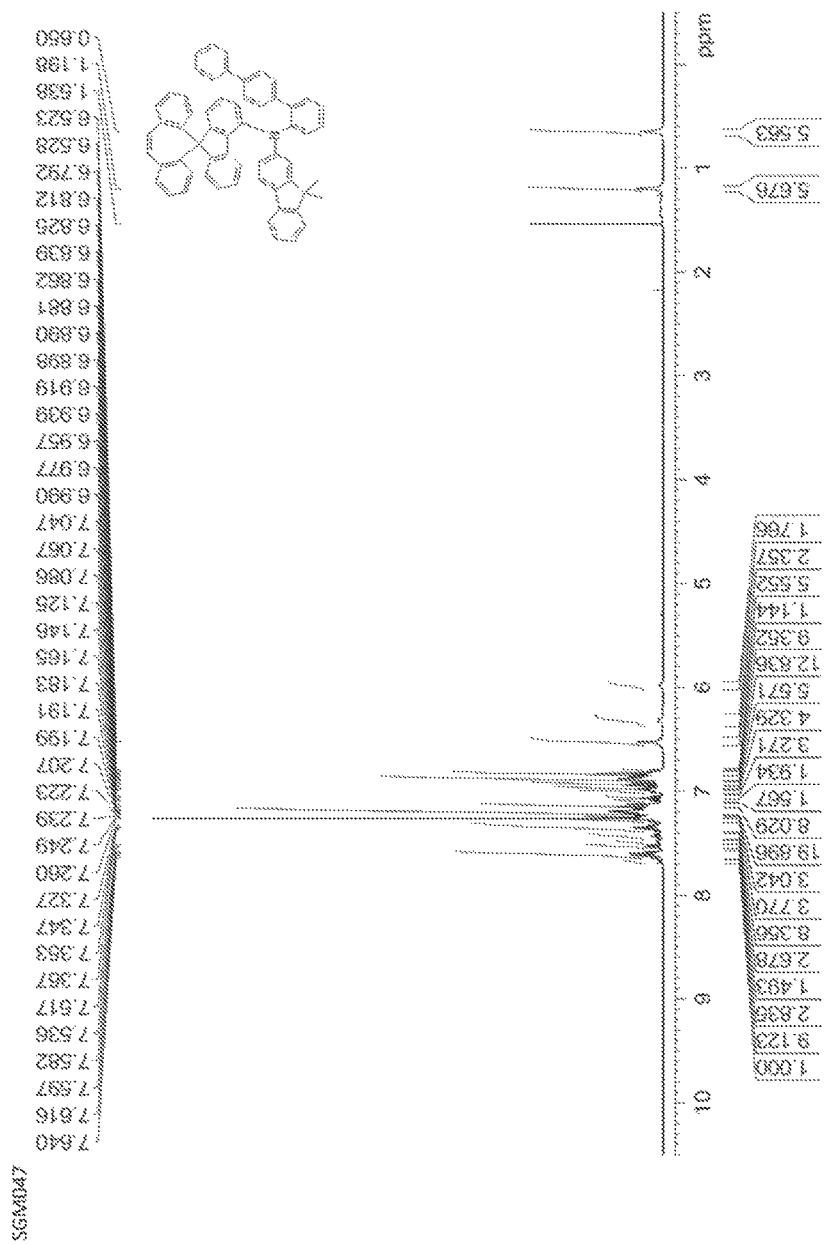
FIG. 14 is 1H NMR data of Compound (14) (SGM 047) of the present disclosure.
Figure 15:
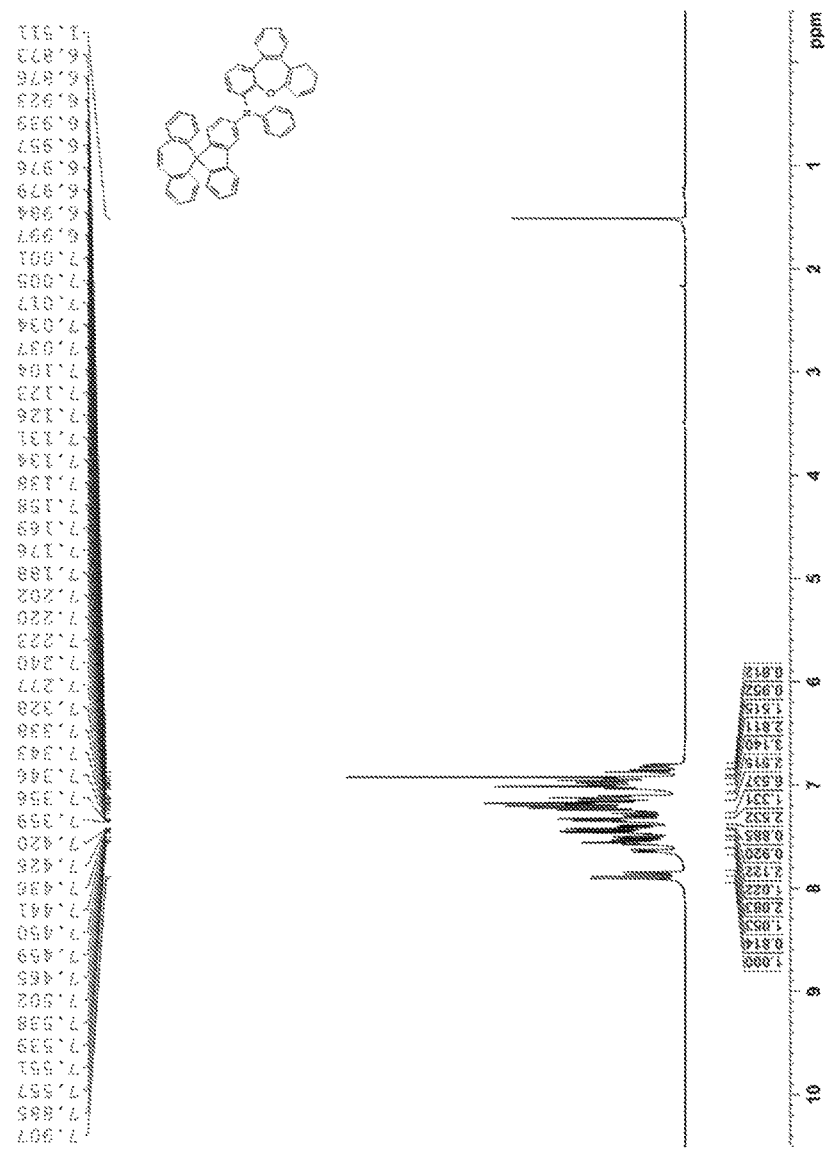
FIG. 15 is 1H NMR data of Compound (15) (SGM 566) of the present disclosure.
Figure 16:
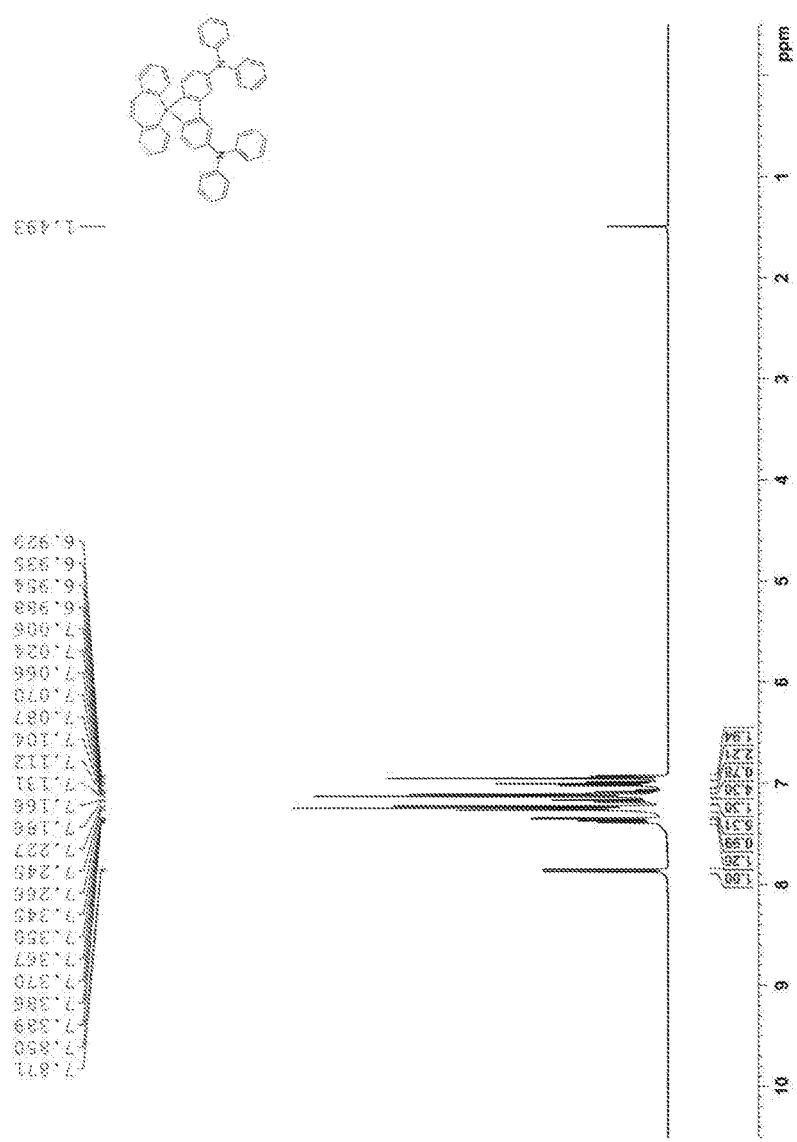
FIG. 16 is 1H NMR data of Compound (16) (SGM 586) of the present disclosure.
Figure 17:
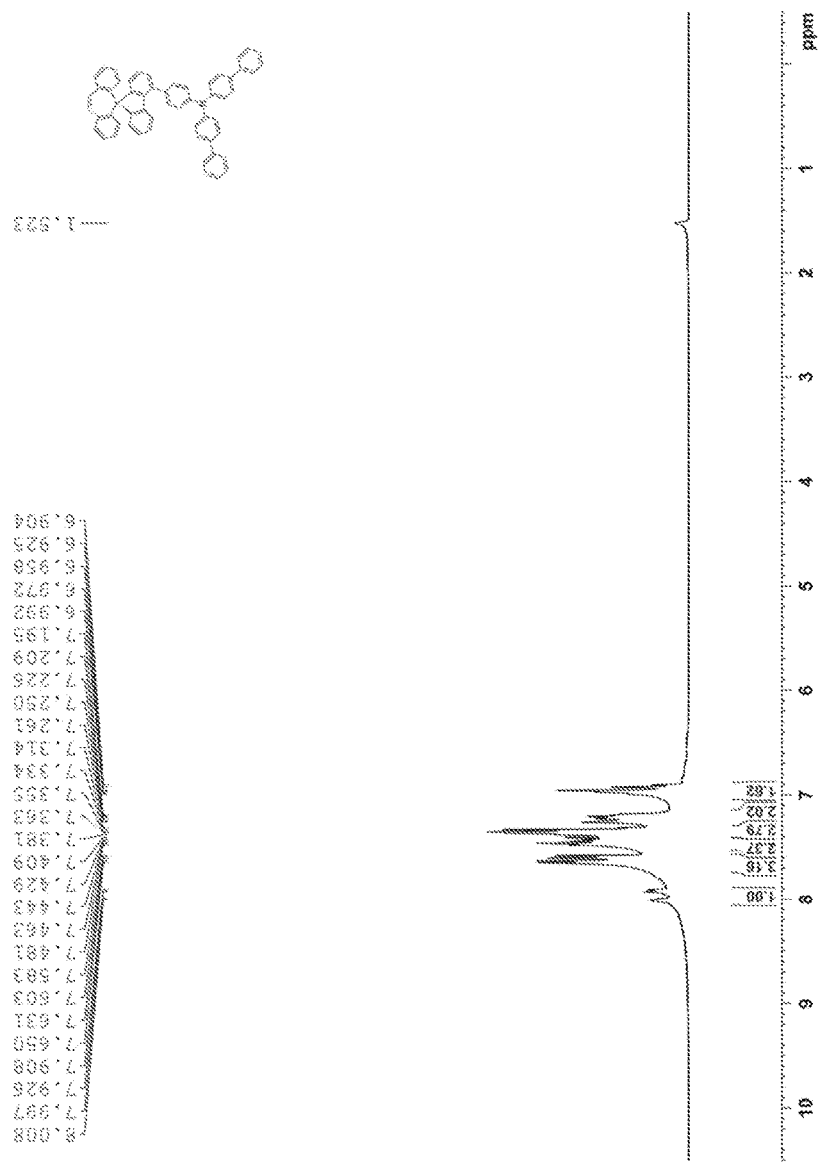
FIG. 17 is 1H NMR data of Compound (17) (SGM 587) of the present disclosure.

In another embodiment, the organic electronic device can be an organic solar cell. FIG. 3 is a perspective view showing an exemplary structure of an organic solar cell used herein. As shown in FIG. 3, the organic solar cell may comprise: a first electrode 21; a second electrode 22; and an organic layer 23 disposed between the first electrode 21 and the second electrode 22 and comprising any one of the aforesaid compounds. Herein, the organic layer 23 may be served as a carrier transport layer.

Other objects, advantages, and novel features of the invention will become more apparent from the following detailed description when taken in conjunction with the accompanying drawings.

EXAMPLES

The following examples are provided in order to explain the characteristics of the present disclosure. However, the present disclosure is not limited by the following descriptions of the examples.

The following syntheses are carried out, unless indicated otherwise, under a protected-gas atmosphere. The starting materials can be purchased from Aldrich or Alfa or obtained in accordance with literature procedures.

Synthesis Example 1—Intermediates A1 to A9 and Synthesis Thereof

Intermediates A1 to A7 used for preparing the compounds of Formula (I) are listed in the following Table 1, wherein the numbers below each intermediates refers to the CAS numbers thereof.

TABLE 1

| Intermediates A1 to A9 | |
|---|---|
| [structure] 897671-81-7 | Intermediate A1 |
| [structure] 1198395-24-2 | Intermediate A2 |
| [structure] 29875-73-8 | Intermediate A3 |

TABLE 1-continued

| Intermediates A1 to A9 | |
|---|---|
| [structure] 122-39-4 | Intermediate A4 |
| [structure] 102113-98-4 | Intermediate A5 |
| [structure] | Intermediate A6 |
| [structure] | Intermediate A7 |
| [structure] | Intermediate A8 |
| [structure] | Intermediate A9 |

Intermediates A1 to A5

The intermediates A1 to A5 were purchased from Aldrich or Alfa, and CAS No. were listed above.

Synthesis of Intermediates A6 to A9

[Scheme I]

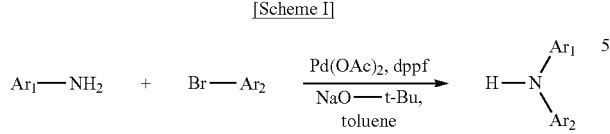

The intermediates A6 to A9 can be prepared according to the above Scheme I. The starting materials $Ar_1$—$NH_2$ (arylamine) and Br—$Ar_2$(arylbromide) are listed in the following Table 2.

Briefly, a mixture of arylbromide (1.0 eq), arylamine (1.05 eq), Pd(OAc)$_2$ (0.01 eq), 1,1'-Bis(diphenylphosphino)ferrocene (0.04 eq), sodium tert-butoxide (1.5 eq), and toluene was taken in a pressure tube and heated at 80° C. for 12 h under N$_2$ atmosphere. After completion of the reaction, the volatiles were removed under vacuum, and the resulting solution extracted with dichloromethane (3×60 mL). The combined organic extract was washed with brine solution, dried over Na$_2$SO$_4$, and concentrated to leave a yellow solid. Further, the crude product was purified by column chromatography on silica gel by using hexane/dichloromethane mixture (2:1 v/v) as an eluent. The analysis data of the obtained products, i.e. Intermediates A6 to A9, are listed in the following Table 2.

Synthesis Example 2—Intermediates B1 to B4 and Synthesis Thereof

Intermediates B1 to B4 used for preparing the compounds of Formula (I) are listed in the following Table 3, wherein the numbers below each intermediates refers to the CAS numbers thereof.

TABLE 3

Intermediates B1 to B4

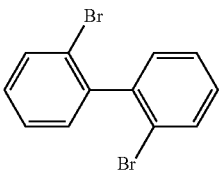 [SMILES: Brc1ccccc1-c1ccccc1Br]

Intermediate B1

13029-09-9

TABLE 2

| Arylbromide | Arylamine | Intermediate | Yield (%) | EA (FD-MS) |
|---|---|---|---|---|
| (dibenzofuran-Br) | (9,9-dimethylfluorene-NH$_2$) | (dibenzofuran-NH-fluorene) Intermediate A6 | 83.4 | C$_{27}$H$_{21}$NO (375.46) |
| (dibenzofuran-Br) | (9,9-dimethylfluorene-NH$_2$) | (dibenzofuran-NH-fluorene) Intermediate A7 | 80.2 | C$_{27}$H$_{21}$NO (375.46) |
| (dibenzoxepine-Br) | (phenyl-NH$_2$) | (dibenzoxepine-NH-phenyl) Intermediate A8 | 81.7 | C$_{24}$H$_{17}$NO (335.4) |
| (bromoterphenyl) | (9,9-dimethylfluorene-NH$_2$) | (fluorene-NH-terphenyl) Intermediate A9 | 89.9 | C$_{33}$H$_{27}$N (375.46) |

TABLE 3-continued

Intermediates B1 to B4

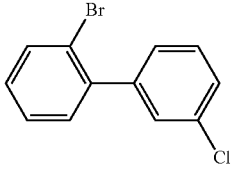 [SMILES: Clc1cccc(-c2ccccc2Br)c1]

Intermediate B2
154407-17-7

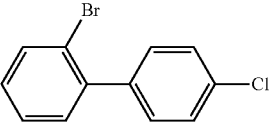 [SMILES: Clc1ccc(-c2ccccc2Br)cc1]

Intermediate B3
179526-95-5

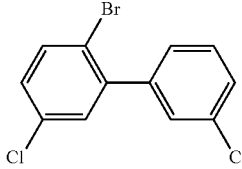

Intermediate B4

Synthesis of Intermediate B4

A solution of 1-bromo-2-chloro-4-iodobenzene (1.0 eq), 4-Chlorophenylboronic acid (1.1 eq), Pd(OAc)$_2$ (0.01 eq), PPh$_3$ (0.04 eq), and 3.0 M K$_2$CO$_3$ aqueous solution (2.0 eq) in toluene (0.4M) was heated under nitrogen at 65° C. for 12 hour. After cooling to room temperature, the solvent was then removed using a rotary evaporator, and the remaining substance was purified with column chromatography to obtain intermediate B4 (65%) MS: [M]$^-$=301.99.

Synthesis Example 3—Intermediates C1 to C5 and Synthesis Thereof

Intermediates C1 to C5 used for preparing the compounds of Formula (I) are listed in the following Table 4.

TABLE 4

Intermediates C1 to C5

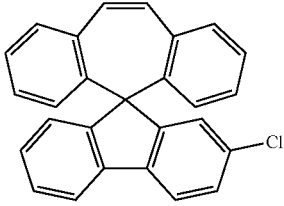 [SMILES: Clc1ccc2c(c1)C1(c3ccccc3C=Cc3ccccc31)c1ccccc1-2]

Intermediate C1

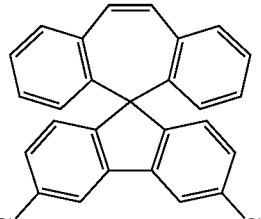

Intermediate C2

TABLE 4-continued

Intermediates C1 to C5

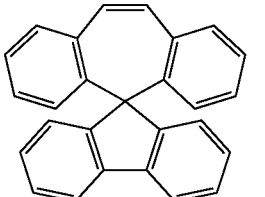

Intermediate C3

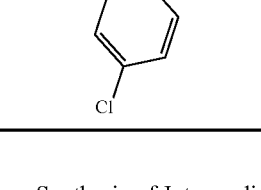

Intermediate C4

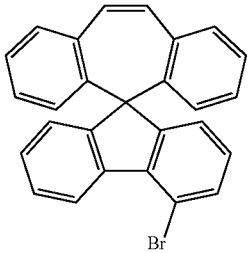 [SMILES: Brc1cccc2c1-c1ccccc1C21c2ccccc2C=Cc2ccccc21]

Intermediate C5

Synthesis of Intermediates C1 to C4

[Scheme II]

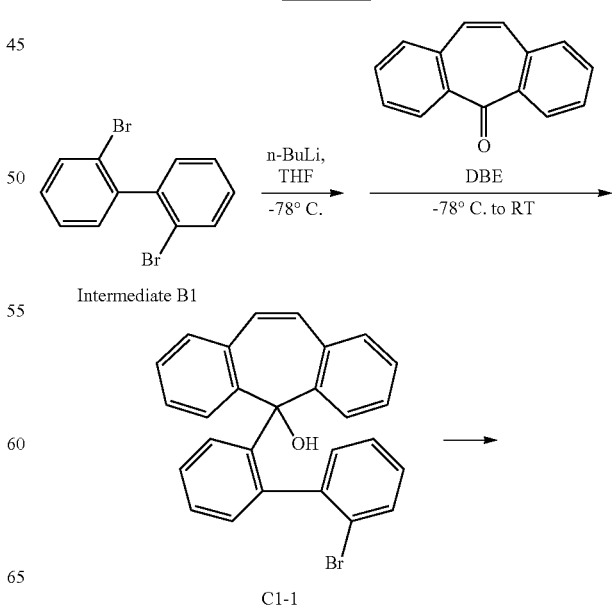

Intermediate B1

C1-1

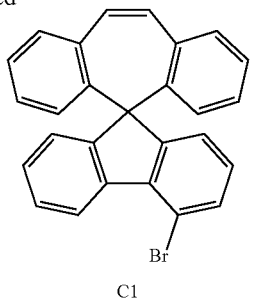

C1

The intermediates C1 to C3 can be prepared according to the above Scheme II.

Step 1: Synthesis of Spiro Alcohol

Intermediate B1 (1.0 eq) was dissolved in THF (0.4M) in a three-neck flask and added n-BuLi (1.0 eq) dropwise under −78° C. After stirring for 0.5 h, 5-Dibenzosuberenone (DBE, 0.7 eq) was added. After completion of a reaction, the reaction solution was quenched with water, and a water layer was extracted with ethyl acetate. The extracted solution and an organic layer were combined and washed with saturated saline, and then dried with magnesium sulfate. After drying, this mixture was subjected to suction filtration, and when a filtrate was concentrated, 19 g of a light yellow, powdery solid of 9-(biphenyl-2-yl)-dibenzosuberen-5-ol (C1-1, C2-1 or C3-1) that was a target matter was obtained.

Step 2: Synthesis of Intermediates C1 to C4

To the 9-(biphenyl-2-yl)-dibenzosuberen-5-ol (Spiro-alcohol B1-2, B2-2 or B3-2) (1.0 eq), acetic acid (w/v=1/3 to the reactant) and $H_2SO_4$(5 drops) were added, and the mixture was stirred at 110° C. 6 h. The reaction was monitored by HPLC. After completion of a reaction, the precipitate was separated by filtration. The remaining substance was purified with column chromatography to obtain compound of spiro-fluorene-dibenzosuberene (intermediates C1 to C4).

The yields and MS analysis data of the intermediates C1 to C4 are also listed in the following Table 5.

TABLE 5

| Intermediate B | Spiro-alcohol | Intermediate C | Yield (%) | Formula (FD-MS) |
|---|---|---|---|---|
| Intermediate B1 | Intermediate C1-1 | Intermediate C1 | 82.1 | $C_{27}H_{17}Br$ (421.33) |
| Intermediate B2 | Intermediate C2-1 | Intermediate C2 | 83.6 | $C_{27}H_{17}Cl$ (376.88) |
| Intermediate B3 | Intermediate C3-1 | Intermediate C3 | 85.9 | $C_{27}H_{17}Cl$ (376.88) |
| Intermediate B4 | Intermediate C4-1 | Intermediate C4 | 84.2 | $C_{27}H_{16}Cl_2$ (411.32) |

Synthesis of Intermediate C5

[Scheme III]

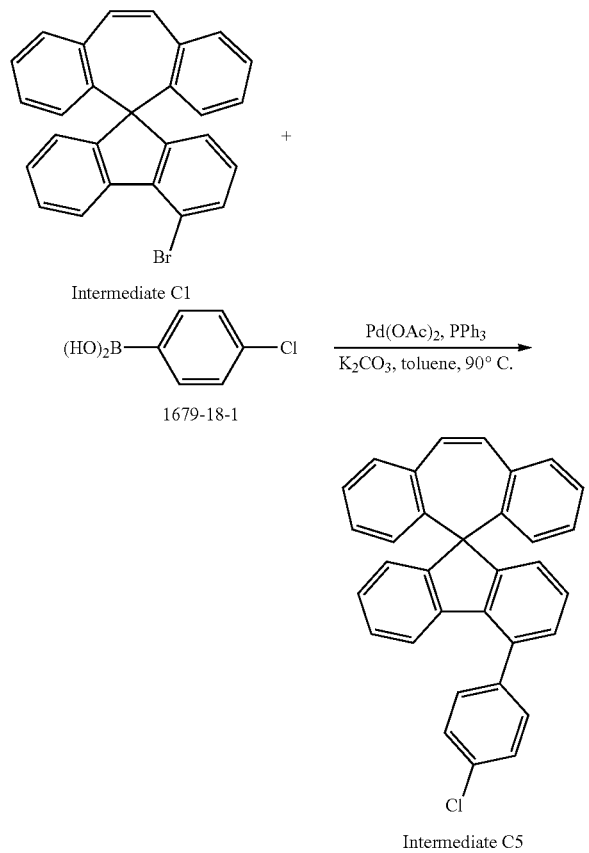

Intermediate C1

(HO)₂B—⟨phenyl⟩—Cl   $\xrightarrow{\text{Pd(OAc)}_2,\ \text{PPh}_3}{\text{K}_2\text{CO}_3,\ \text{toluene},\ 90°\text{C.}}$ 1679-18-1

Intermediate C5

Intermediate C1 (1.0 eq), 4-chlorophenylboronic acid (1.1 eq), Pd(OAc)₂ (0.01 eq), PPh₃ (0.04 eq), 3.0 M K₂CO₃ aqueous solution (1.5 eq) in toluene was heated at 100° C. for 12 h. After completion of the reaction, the volatiles were removed under vacuum, and the resulting solution extracted with dichloromethane (3×60 mL). The combined organic extract was washed with brine solution, dried over Na₂SO₄, and concentrated to leave a yellow solid. Further, the crude product was purified by column chromatography on silica gel to get intermediate C5 (94%).

Synthesis Example 4—Compounds (1), (2), (4) to (8), (10) to (12), (14) to (17)

Synthesis of Compounds (1), (2), (4) to (8), (10) to (12), (14) to (17)

The compounds of the present disclosure can be synthesized according to the following Scheme IV.

Intermediate C1-C4+Intermediate A1-A7→Embodiment    [Scheme IV]

Briefly, a mixture of palladium diacetate (Pd(OAc)₂, 0.5% eq), tris-tert-butylphosphoniumtetrafluoroborate (0.02 eq), intermediates A1 to A9 (1.0 eq/2.1 eq for SGM586 synthesis), intermediates C1 to C5 (1.0 eq), and sodium tert-butoxide (t-BuONa, 1.5 eq) was stirred in toluene for 8~24 h at 110° C. under an argon atmosphere. After cooling to room temperature, the reaction quenched with DI water, and then the mixture was extracted with ethyl acetate. The organic extracts were combined and washed with brine and dried with anhydrous MgSO₄. The precipitate was separated by filtration. The solvent was removed under reduced pressure, and the residue went through a silica-gel column to give the compounds of (1), (2), (4) to (8), (10) to (12), (14) to (17).

The products (1), (2), (4) to (8), (10) to (12), (14) to (17), the used intermediates, the yields, and the MS analysis data are listed in the following Table 6. In addition, the 1H NMR of the products (1), (2), (4) to (8), (10) to (12), (14) to (17) are shown in FIGS. 4 to 17.

TABLE 6

| SGM | Intermediate A | Intermediate B | Embodiment | Yield (%) | EA/ (FD-MS) |
|---|---|---|---|---|---|
| SGM 058 (1) | Intermediate A2 | Intermediate C3 | 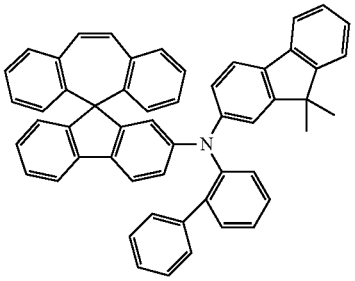 [SMILES: CC1(C)c2ccccc2-c2ccc(N(c3ccc4c(c3)C3(c5ccccc5C=Cc5ccccc53)c3ccccc3-4)c3ccccc3-c3ccccc3)cc21] | 80.5 | C₅₄H₃₉N (701.89) |
| SGM 430 (2) | Intermediate A6 | Intermediate C3 | 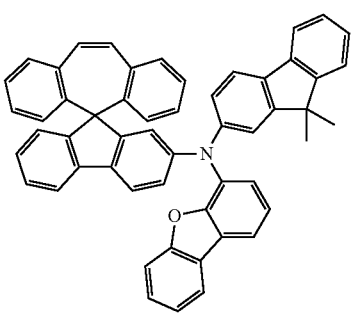 [SMILES: CC1(C)c2ccccc2-c2ccc(N(c3ccc4c(c3)C3(c5ccccc5C=Cc5ccccc53)c3ccccc3-4)c3cccc4c3oc3ccccc34)cc21] | 77.6 | C₅₄H₃₇NO (715.88) |

TABLE 6-continued
| SGM | Intermediate A | Intermediate B | Embodiment | Yield (%) | EA/ (FD-MS) |
|---|---|---|---|---|---|
| SGM 435 (4) | Intermediate A3 | Intermediate C3 | 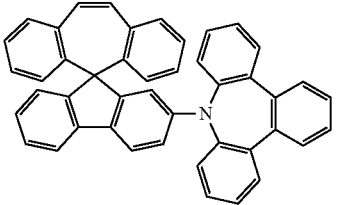 [SMILES: C1=Cc2ccccc2C2(c3ccccc31)c1ccccc1-c1ccc(N3c4ccccc4-c4ccccc4-c4ccccc43)cc12] | 73.1 | C$_{45}$H$_{29}$N (583.72) |
| SGM 017 (5) | Intermediate A1 | Intermediate C3 | 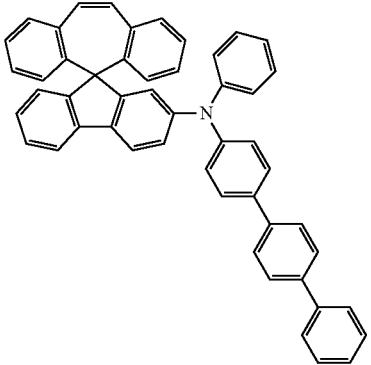 [SMILES: C1=Cc2ccccc2C2(c3ccccc31)c1ccccc1-c1ccc(N(c3ccccc3)c3ccc(-c4ccc(-c5ccccc5)cc4)cc3)cc12] | 81.5 | C$_{51}$H$_{35}$N (661.83) |
| SGM 053 (6) | Intermediate A2 | Intermediate C2 | 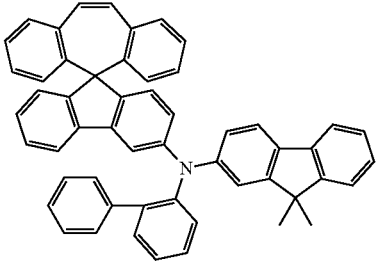 [SMILES: CC1(C)c2ccccc2-c2ccc(N(c3ccc4c(c3)-c3ccccc3C43c4ccccc4C=Cc4ccccc43)c3ccccc3-c3ccccc3)cc21] | 70.5 | C$_{54}$H$_{39}$N (701.89) |
| SGM 428 (7) | Intermediate A6 | Intermediate C2 | 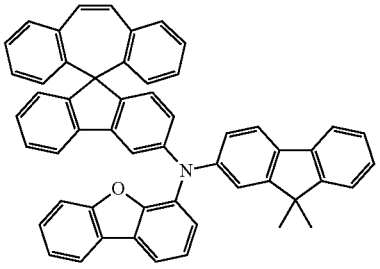 [SMILES: CC1(C)c2ccccc2-c2ccc(N(c3ccc4c(c3)-c3ccccc3C43c4ccccc4C=Cc4ccccc43)c3cccc4c3oc3ccccc34)cc21] | 79.9 | C$_{54}$H$_{37}$NO (715.88) |
| SGM 429 (8) | Intermediate A7 | Intermediate C2 | 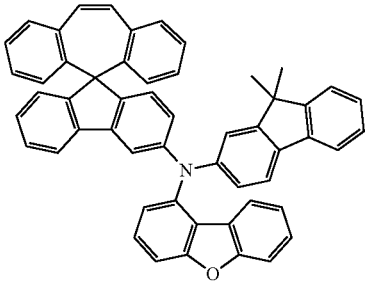 [SMILES: CC1(C)c2ccccc2-c2ccc(N(c3ccc4c(c3)-c3ccccc3C43c4ccccc4C=Cc4ccccc43)c3cccc4oc5ccccc5c34)cc21] | 73.2 | C$_{54}$H$_{37}$NO (715.88) |

TABLE 6-continued

| SGM | Intermediate A | Intermediate B | Embodiment | Yield (%) | EA/ (FD-MS) |
|---|---|---|---|---|---|
| SGM 018 (10) | Intermediate A2 | Intermediate C1 | | 82.5 | C$_{54}$H$_{39}$N (701.89) |
| SGM 045 (11) | Intermediate A6 | Intermediate C1 | | 80.9 | C$_{54}$H$_{37}$NO (715.88) |
| SGM 432 (12) | Intermediate A7 | Intermediate C1 | | 83.1 | C$_{54}$H$_{37}$NO (715.88) |
| SGM 047 (14) | Intermediate A9 | Intermediate C1 | | 76.7 | C$_{60}$H$_{43}$N (777.9) |

TABLE 6-continued

| SGM | Intermediate A | Intermediate B | Embodiment | Yield (%) | EA/ (FD-MS) |
|---|---|---|---|---|---|
| SGM 566 (15) | Intermediate A8 | Intermediate C2 | 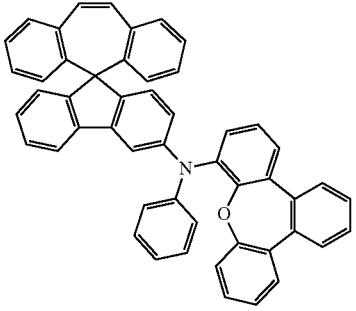 [SMILES: C1=Cc2ccccc2C2(c3ccccc31)c1ccccc1-c1cc(N(c3ccccc3)c3cccc4c3Oc3ccccc3-c3ccccc3-4)ccc12] | 71.2 | $C_{51}H_{33}NO$ (675.81) |
| SGM 586 (16) | Intermediate A4 | Intermediate C4 | 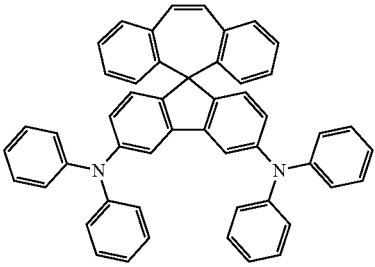 [SMILES: C1=Cc2ccccc2C2(c3ccccc31)c1ccc(N(c3ccccc3)c3ccccc3)cc1-c1cc(N(c3ccccc3)c3ccccc3)ccc12] | 85.6 | $C_{51}H_{36}N_2$ (676.84) |
| SGM 587 (17) | Intermediate A5 | Intermediate | 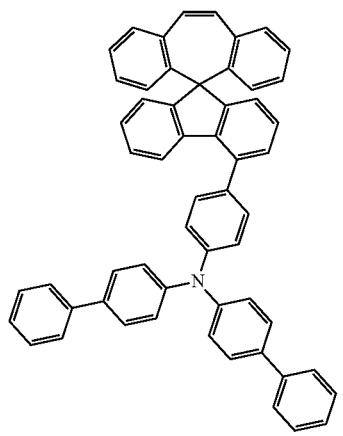 [SMILES: C1=Cc2ccccc2C2(c3ccccc31)c1ccccc1-c1c(-c3ccc(N(c4ccc(-c5ccccc5)cc4)c4ccc(-c5ccccc5)cc4)cc3)cccc12] | 90.5 | $C_{57}H_{39}N$ (737.93) |

Example—OLED Device Fabrication

A glass substrate having ITO (indium tin oxide) coated thereon to a thickness 1500 Å was placed in distilled water containing a detergent dissolved therein, and was ultrasonically washed. Herein, the detergent was a product manufactured by Fischer Co., and the distilled water was filtered twice through a filter (Millipore Co.). After the ITO had been washed with detergent for 30 minutes, it was ultrasonically washed twice with distilled water for 10 minutes followed by isopropyl alcohol, acetone, and methanol, which was then dried, after which it was transported to a plasma cleaner. Then, the substrate was clean with oxygen plasma for 5 minutes, and then transferred to a vacuum evaporator. Various organic materials and metal materials were sequentially deposited on the ITO substrate to obtain the OLED device of the present examples. The vacuum degree during the deposition was maintained at $1 \times 10^{-6}$ to $3 \times 10^{-7}$ torr. In addition, the formulas and the code names of the materials used in the following OLED devices were listed in the following Table 7.

Preparation of Blue OLED Device

To fabricate the blue OLED device of the present examples, HAT was firstly deposited on the ITO substrate to form a first hole injection layer with a thickness of 100 Å. HI-2 was deposited on the first hole injection layer with a dopant HAT (5.0 wt %) to form a second hole injection layer having a thickness of 750 Å.

Next, HT-1 or compounds of the present disclosure was deposited to form a first hole transporting layer (HT1) with a thickness of 100 Å; and/or HT-2 or compounds of the present disclosure was deposited to form a second hole transporting layer (HT2) with a thickness of 100 Å.

Then, BH with a dopant BD-1 or BD-2 (3.5 wt %) was deposited on the first or second hole transporting layer to form a light emitting layer having a thickness of 250 Å. ET with a dopant Liq (35.0 wt %) was deposited on the light emitting layer to form an electron transporting layer with a thickness of 250 Å. Liq was deposited on the electron transporting layer to form an electron injection layer with a thickness of 15 Å. Al was deposited on the electron injection layer to form a cathode with a thickness of 1500 Å.

After the aforementioned process, the blue OLED device used in the following test was obtained.

Preparation of Red OLED Device

The preparation of the red OLED device was similar to that of the blue OLED device, except that the second hole injection layer, the light emitting layer and the electron transporting layer.

Herein, the thickness of the second hole injection layer was 2100 Å. RH with a dopant RD (3.5 wt %) was deposited on the first or second hole transporting layer to form a light emitting layer having a thickness of 300 Å. The thickness of the electron transporting layer was 350 Å.

TABLE 7

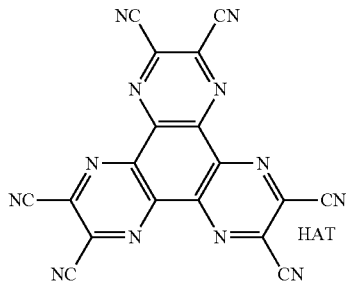
HI-1

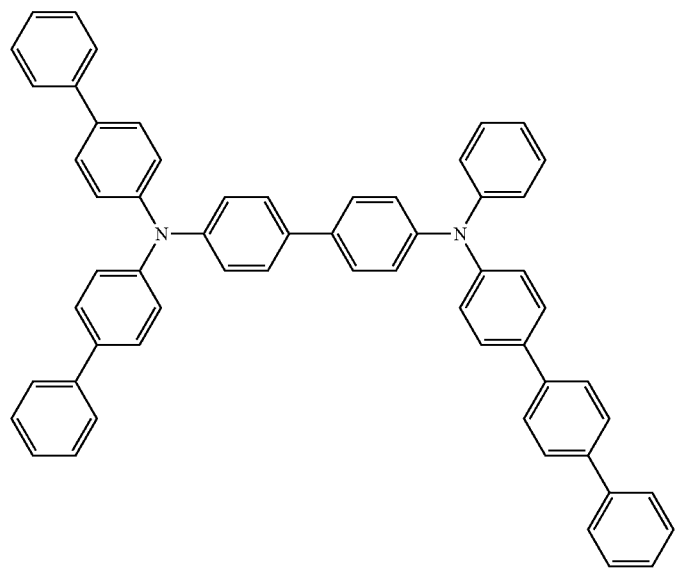 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HI-2

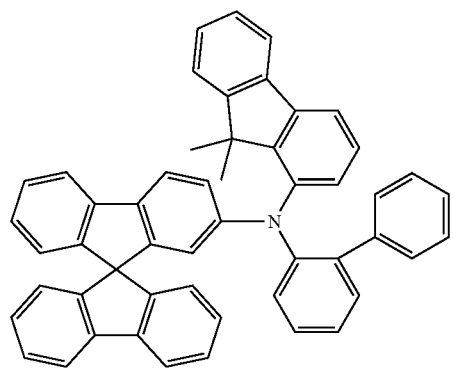 [SMILES: CC1(C)c2ccccc2-c2cccc(N(c3ccc4c(c3)C3(c5ccccc5-c5ccccc53)c3ccccc3-4)c3ccccc3-c3ccccc3)c21]
HT-1

TABLE 7-continued
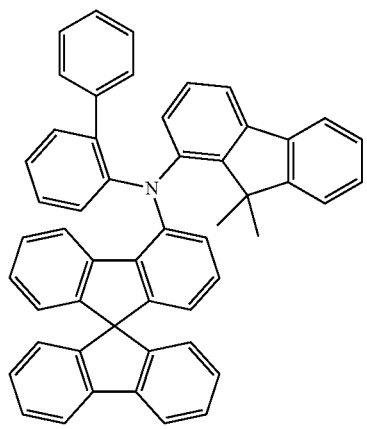 [SMILES: CC1(C)c2ccccc2-c2cccc(N(c3ccccc3-c3ccccc3)c3cccc4c3-c3ccccc3C43c4ccccc4-c4ccccc43)c21]
HT-2
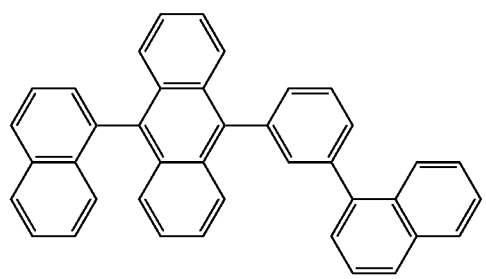 [SMILES: c1cc(-c2cccc3ccccc23)cc(-c2c3ccccc3c(-c3cccc4ccccc34)c3ccccc23)c1]
BH
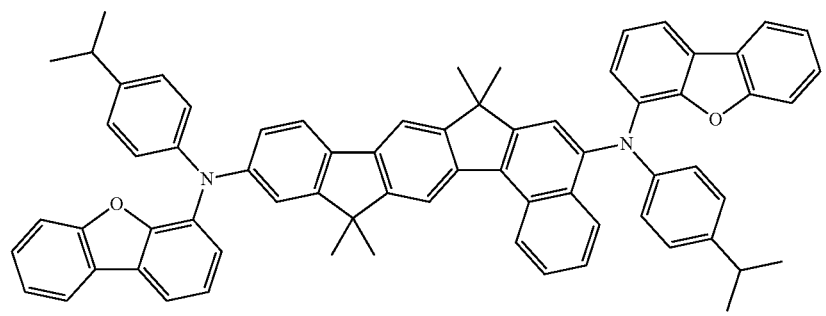 [SMILES: CC(C)c1ccc(N(c2ccc3c(c2)C(C)(C)c2cc4c(cc2-3)C(C)(C)c2cc(N(c3ccc(C(C)C)cc3)c3cccc5c3oc3ccccc35)c3ccccc3c2-4)c2cccc3c2oc2ccccc23)cc1]
BD-1
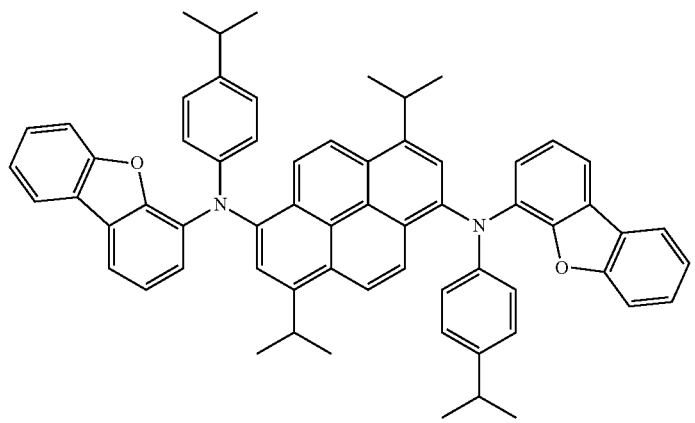 [SMILES: CC(C)c1ccc(N(c2cc(C(C)C)c3ccc4c(N(c5ccc(C(C)C)cc5)c5cccc6c5oc5ccccc56)cc(C(C)C)c5ccc2c3c54)c2cccc3c2oc2ccccc23)cc1]
BD-2

TABLE 7-continued
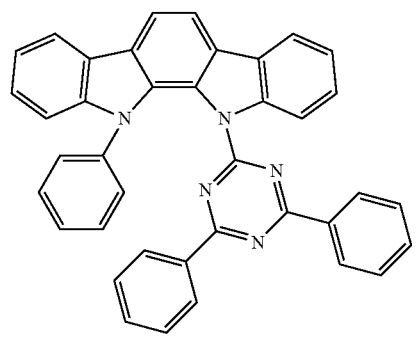 [SMILES: c1ccc(-c2nc(-c3ccccc3)nc(-n3c4ccccc4c4ccc5c6ccccc6n(-c6ccccc6)c5c43)n2)cc1]
RH
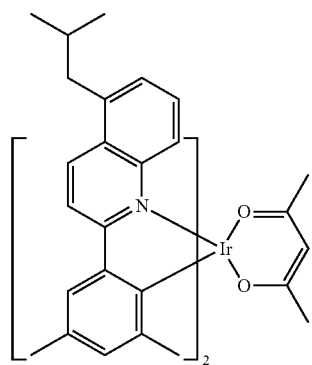
RD
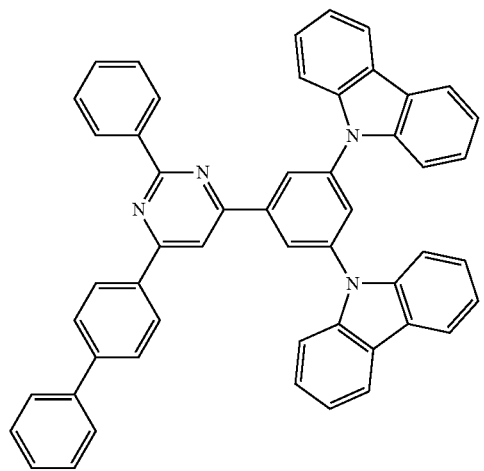 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1]
ET
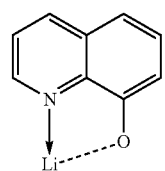
ETD (Liq)

OLED Device Measurement

Device performances of the obtained blue, green and red OLED devices were measured by PR-650. For the blue and red OLED devices, the data were collected at 1000 nits. For the green OLED devices, the data were collected at 3000 nits. Data such as CIE, luminous efficiency (Eff.) and driving voltage (Voltage) are listed in the following Tables 8 to 10.

TABLE 8

Blue device data (in which the blue dopant was BD-1)

| Example | HT1 | HT2 | Color, CIE (x, y) | Voltage (V) | Efficiency (cd/A) |
|---|---|---|---|---|---|
| Example 1 | SGM017 | — | B, (0.136, 0.171) | 4.25 | 13.1 |
| Example 2 | — | SGM018 | B, (0.136, 0.170) | 4.29 | 14.1 |
| Example 3 | — | SGM047 | B, (0.135, 0.194) | 4.40 | 13.3 |
| Example 4 | — | SGM053 | B, (0.136, 0.170) | 4.36 | 12.0 |
| Example 5 | — | SGM058 | B, (0.135, 0.180) | 4.35 | 13.4 |
| Comp Exp (1) | HT-1 | HT-2 | B, (0.135, 0.185) | 4.39 | 12.1 |

TABLE 9

Blue device data

| Example | HT1 | HT2 | Color, CIE (x, y) | Voltage (V) | Efficiency (cd/A) |
|---|---|---|---|---|---|
| Example 6 | — | SGM435 | B, (0.130, 0.147) | 4.25 | 11.0 |
| Example 7 | — | SGM586 | B, (0.129, 0.153) | 4.26 | 11.5 |
| Comp Exp (2) | HT-1 | HT-2 | B, (0.135, 0.154) | 4.31 | 11.1 |

TABLE 10

Red device data

| Example | HT1 | HT2 | Color, CIE (x, y) | Voltage (V) | Efficiency (cd/A) |
|---|---|---|---|---|---|
| Example 8 | — | SGM045 | R, (0.665, 0.333) | 3.54 | 24.6 |
| Example 9 | — | SGM047 | R, (0.665, 0.333) | 3.60 | 25.3 |
| Example 10 | SGM428 | — | R, (0.659, 0.339) | 3.48 | 24.6 |
| Example 11 | SGM430 | — | R, (0.659, 0.340) | 3.32 | 25.0 |
| Example 12 | SGM429 | — | R, (0.660, 0.339) | 3.84 | 27.7 |
| Example 13 | SGM430 | — | R, (0.659, 0.340) | 3.32 | 25.0 |
| Example 14 | — | SGM432 | R, (0.662, 0.336) | 3.57 | 23.9 |
| Example 15 | — | SGM566 | R, (0.660, 0.339) | 3.63 | 25.5 |
| Example 16 | — | SGM587 | R, (0.660, 0.339) | 3.58 | 24.5 |
| Comp Exp (3) | HT-1 | HT-2 | R, (0.661, 0.338) | 3.65 | 23.9 |

According to the results shown in Tables 8 to 10, the OLED device applied with the compound of Formula (I) shows improved luminous efficiency and low driving voltage. Therefore, the compound of Formula (I) of the present disclosure can effectively be used as a hole transporting material of an OLED device.

Although the present disclosure has been explained in relation to its preferred embodiment, it is to be understood that many other possible modifications and variations can be made without departing from the spirit and scope of the invention as hereinafter claimed.

What is claimed is:

1. A compound of Formula (I) below:

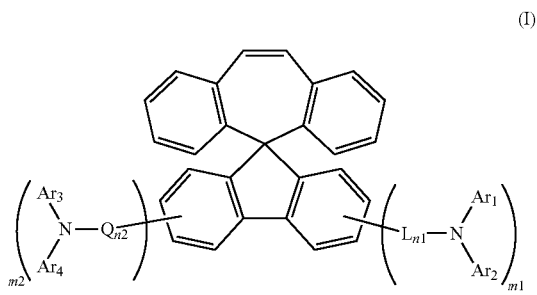

(I)

wherein, m1 and m2 are each independently 0, 1 or 2, and with the proviso that m1 and m2 are not 0 at the same time; and $-L_{n1}-NAr_1Ar_2$ and $-Q_{n2}-NAr_3Ar_4$ are each independently selected from the group consisting of:

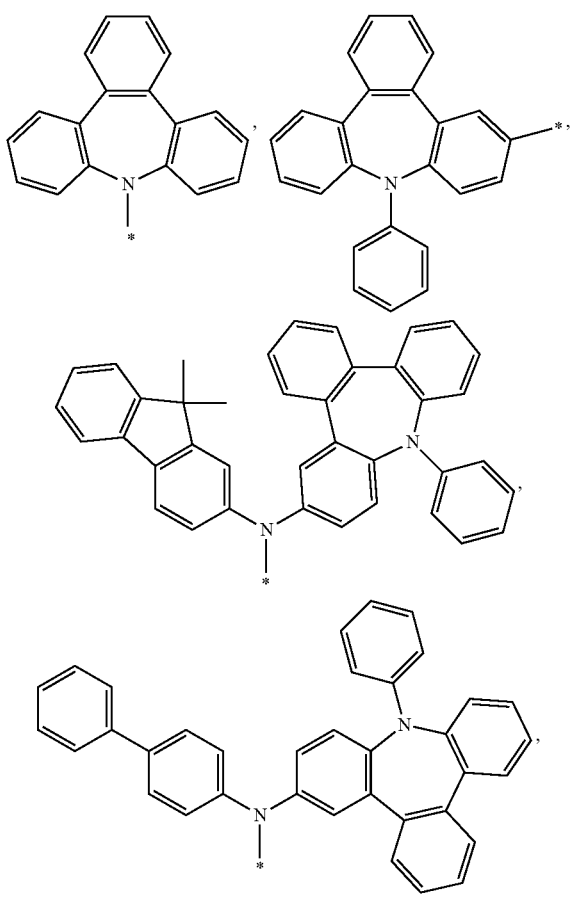

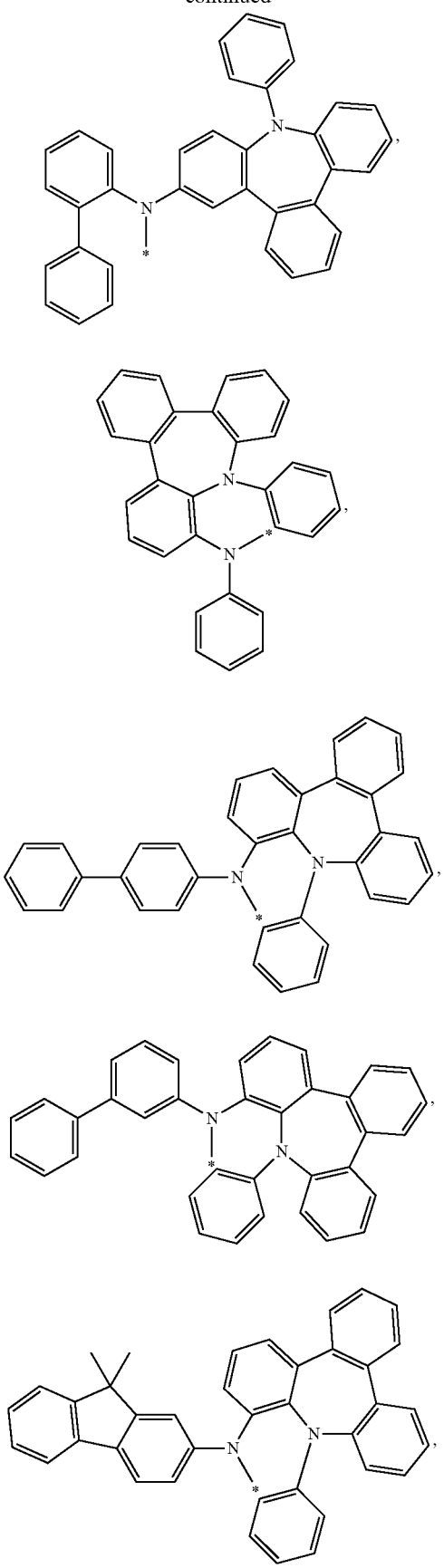
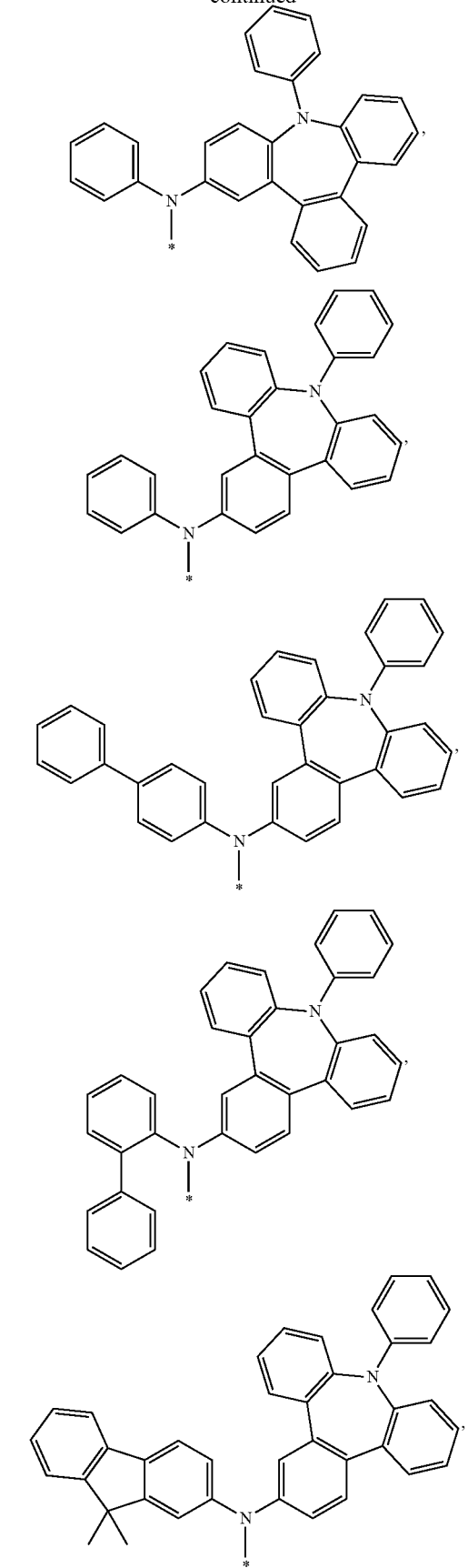

113
-continued
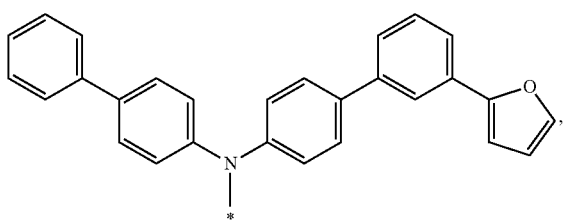
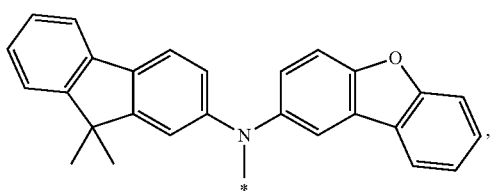
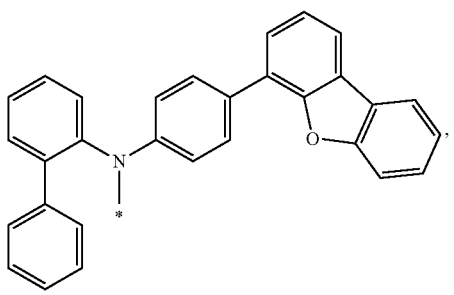
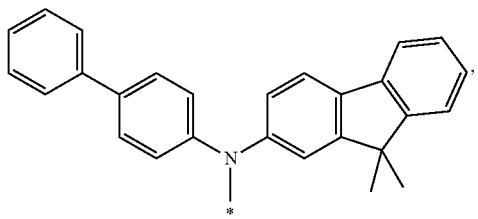
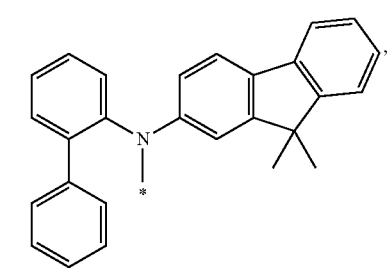
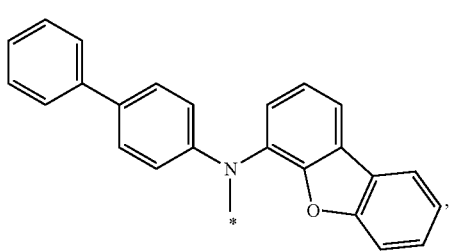
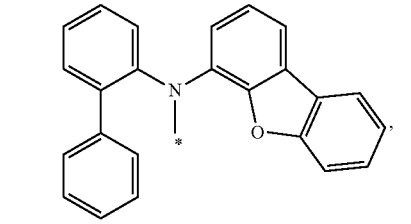
114
-continued
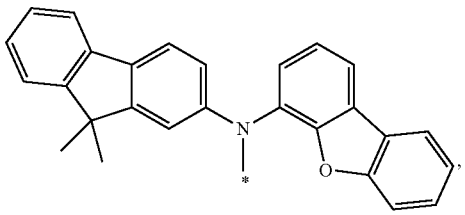
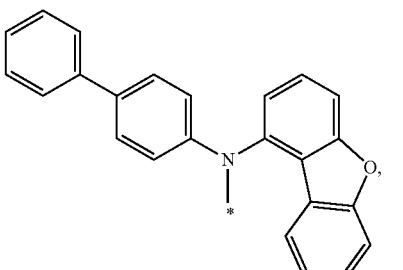
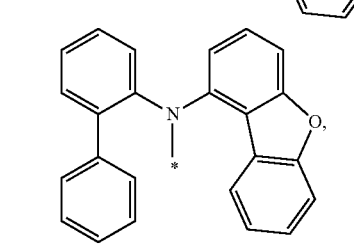
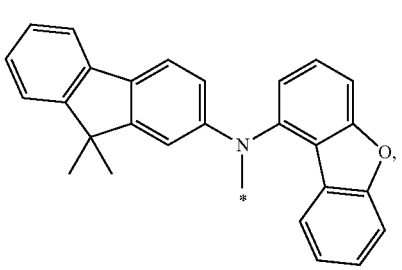
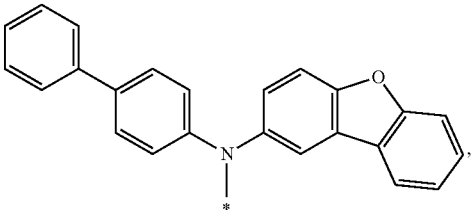
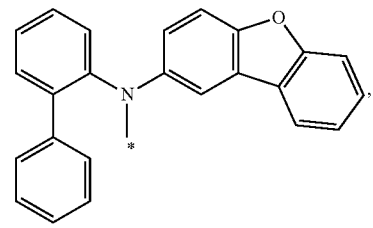
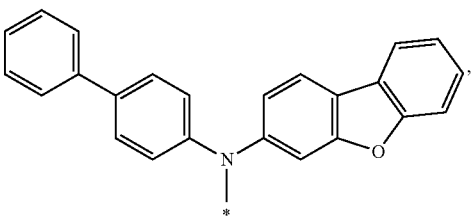

115
-continued
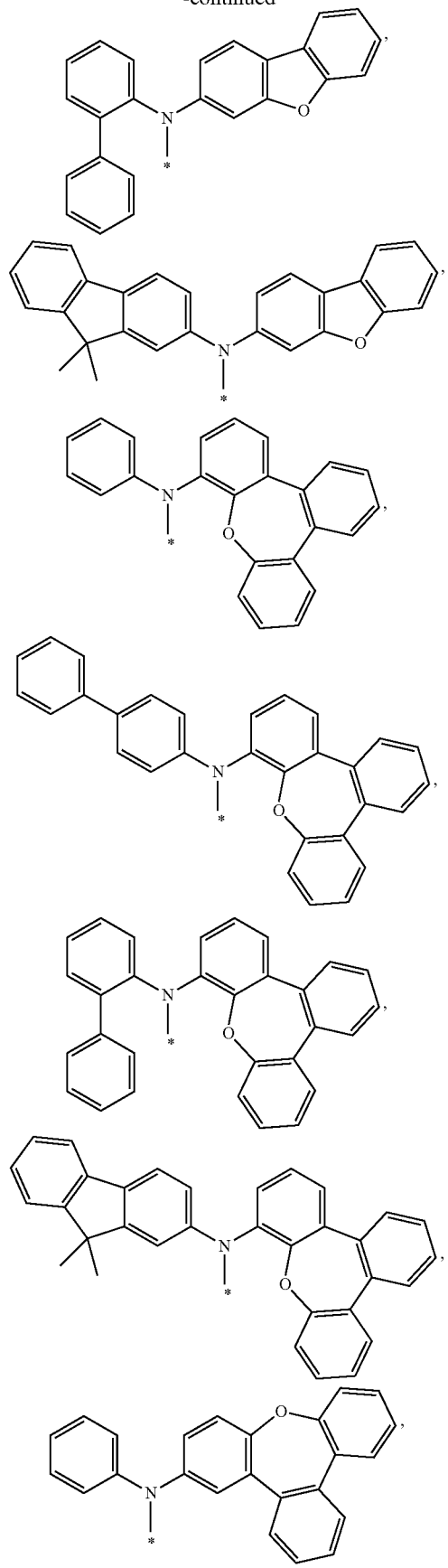
116
-continued
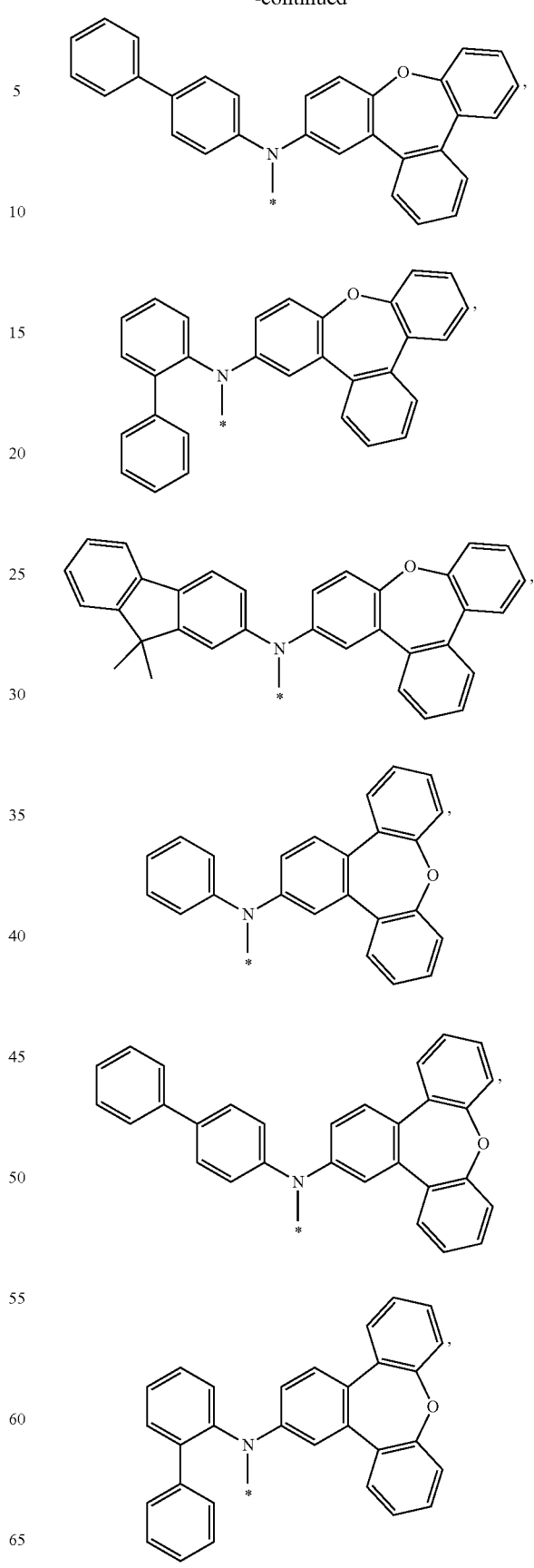

-continued
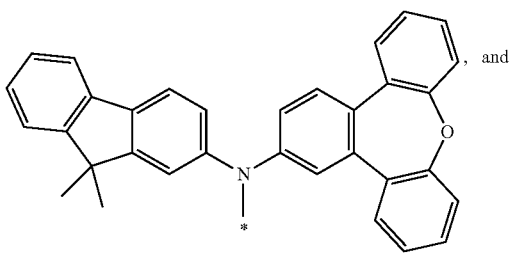, and
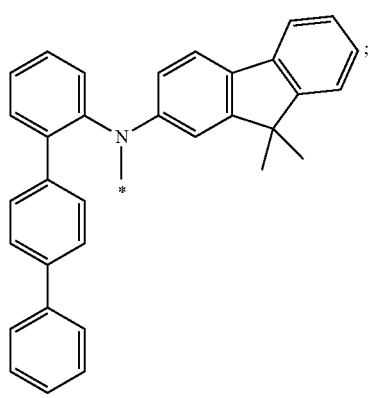;
wherein * represents a bonding position.
2. The compound of claim 1, wherein m1 is 1 and m2 is 0.
3. The compound of claim 1, wherein m1 is 1 and m2 is 1.
4. The compound of claim 3, wherein -$L_{n1}$-$NAr_1Ar_2$ and -$Q_{n2}$-$NAr_3Ar_4$ are the same.
5. The compound of claim 1, wherein the compound is represented by any one of Formulas (I-1) to (I-9) below:
(I-1)
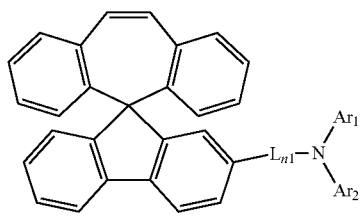
(I-2)
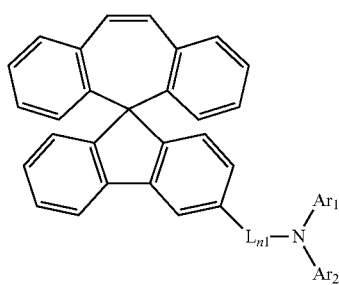
-continued
(I-3)
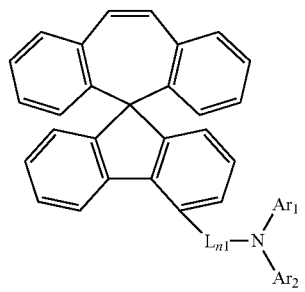
(I-4)
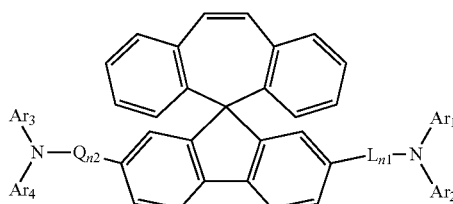
(I-5)
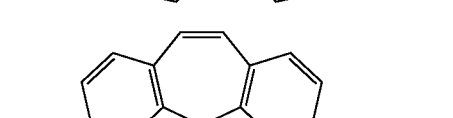
(I-6)
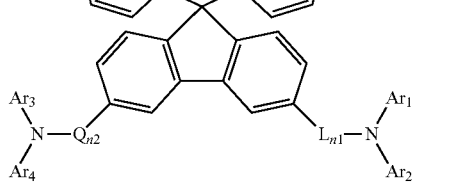
(I-7)
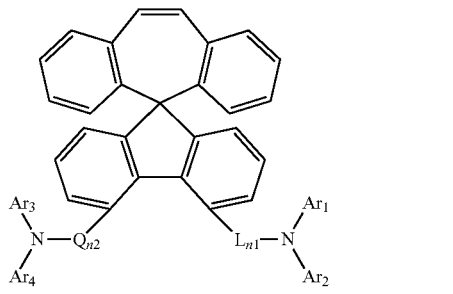
(I-8)
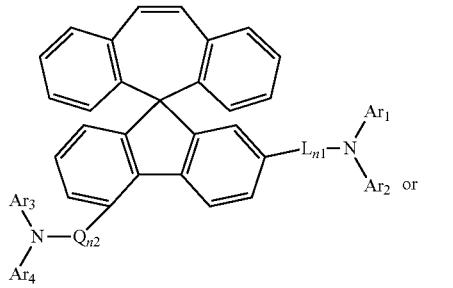 or -continued
(I-9)
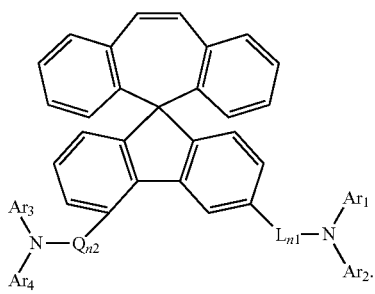
6. The compound of claim 1, wherein the compound is selected from the group consisting of:
(1)
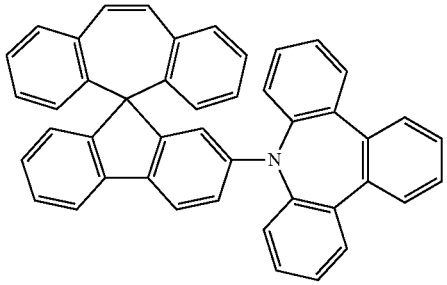
(2)
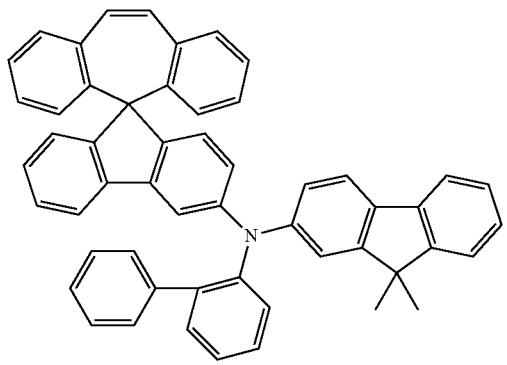
(3)
-continued
(4)
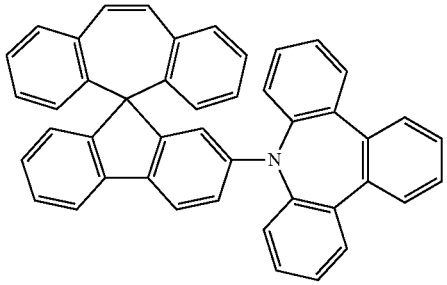
(6)
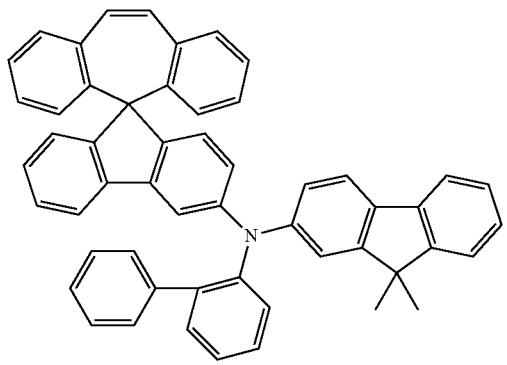
(7)
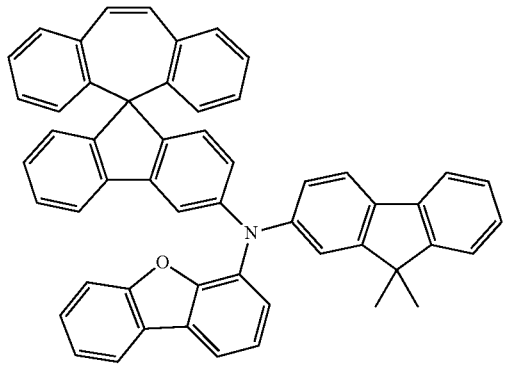
(8)
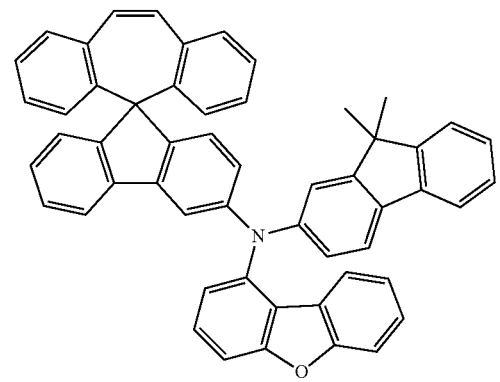

(9)
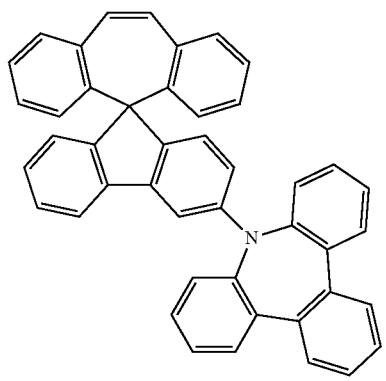
(10)
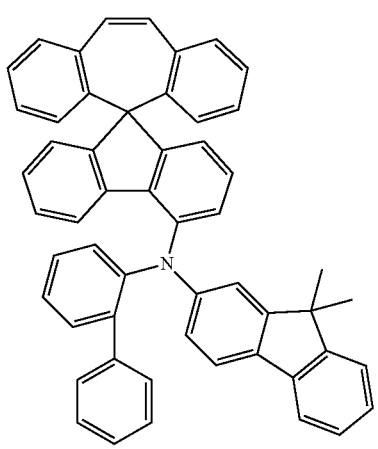
(11)
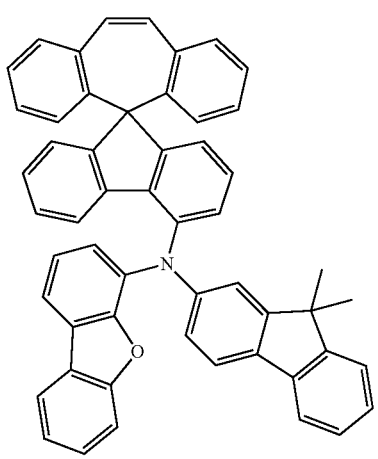
(12)
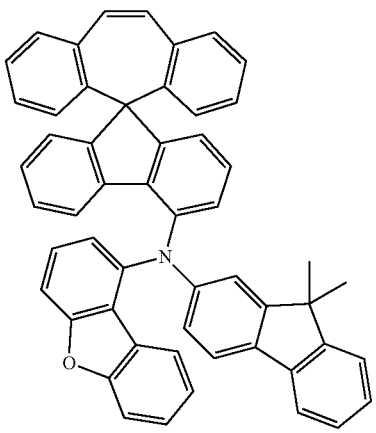
(13)
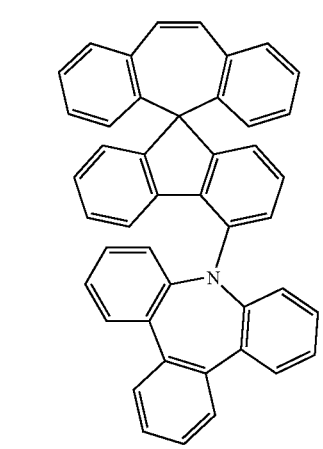
(14)
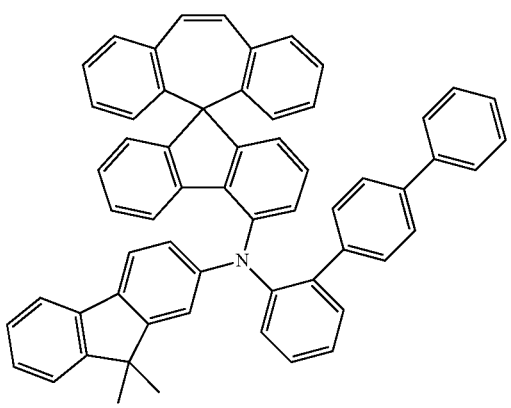

(15)
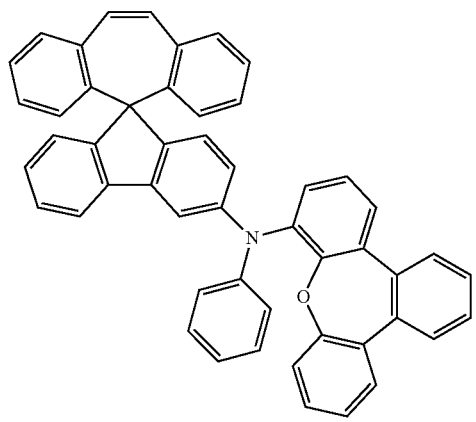
(21)
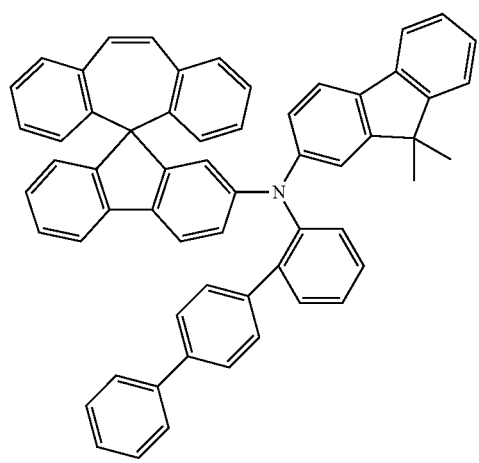
(22)
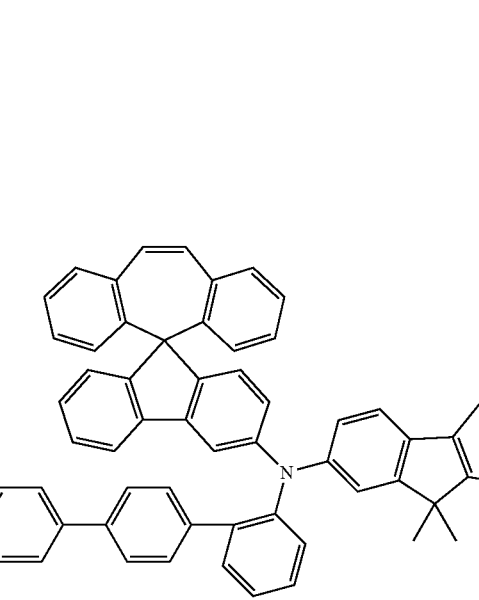
(30)
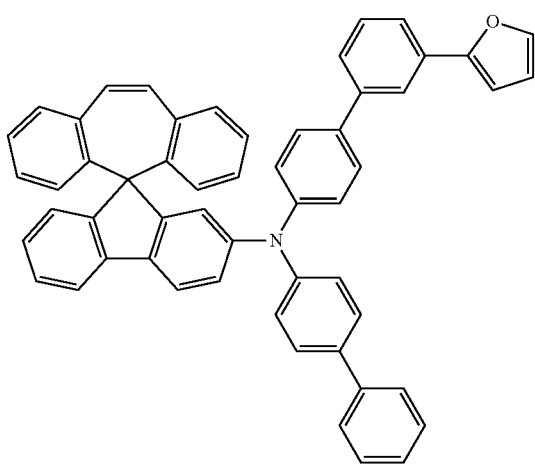
(36)
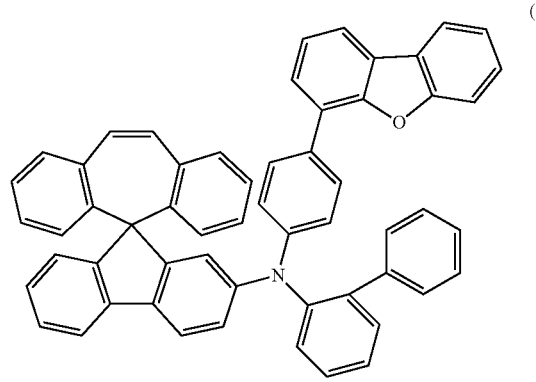
(37)
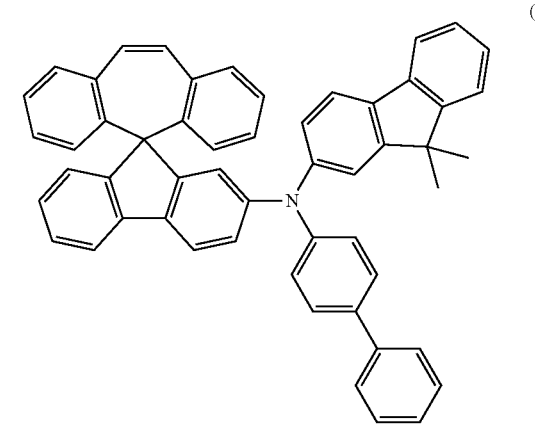
(39)
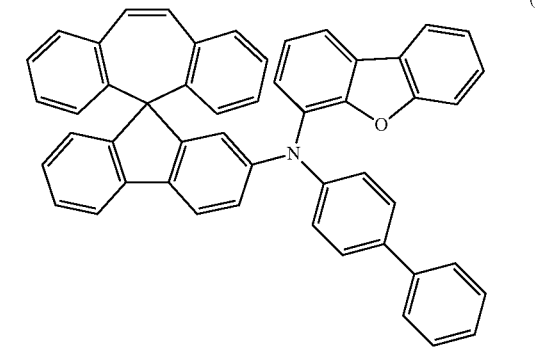

(41)
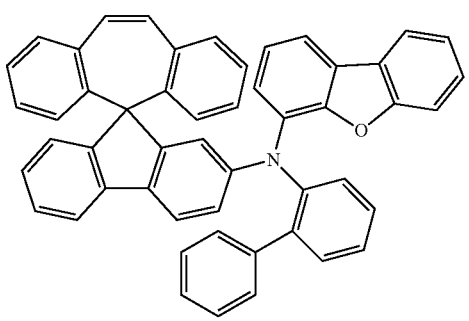
(42)
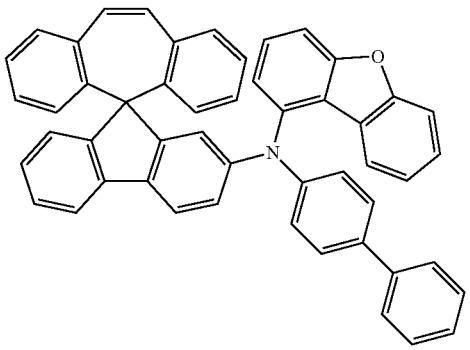
(44)
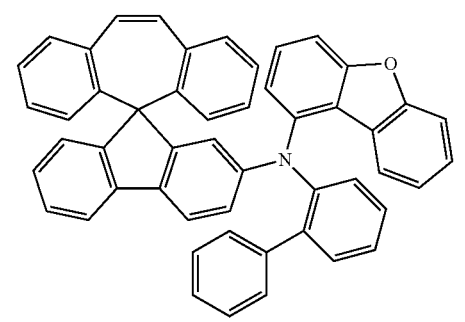
(45)
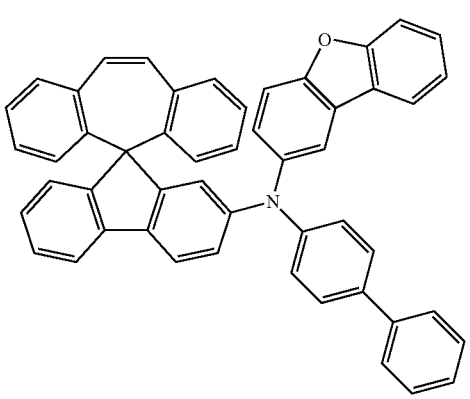
(47)
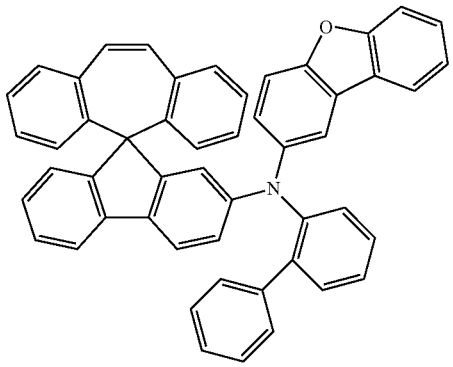
(48)
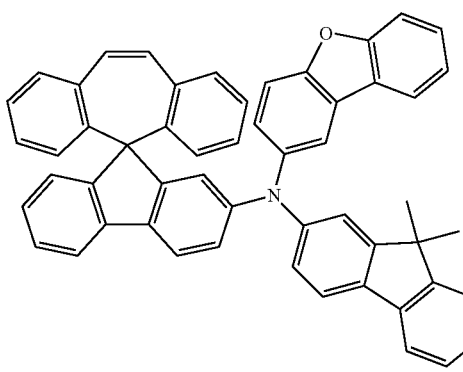
(50)
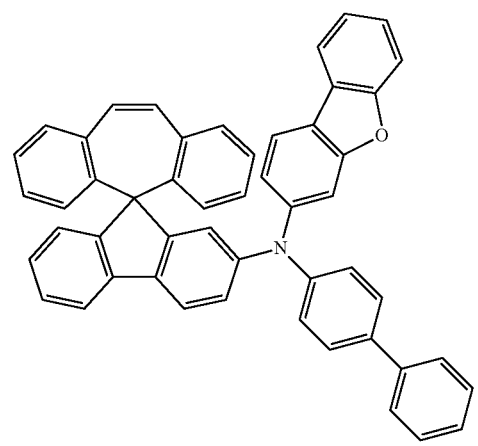
(52)
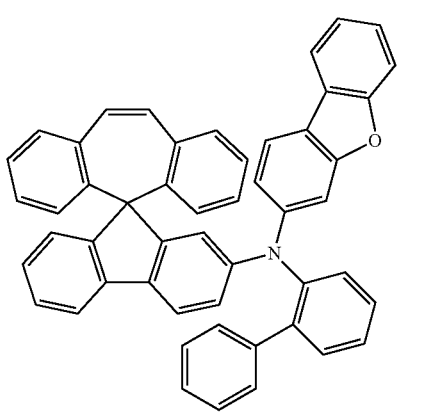

(53)
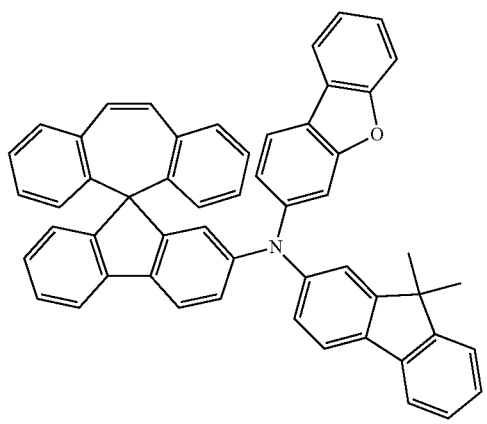
(55)
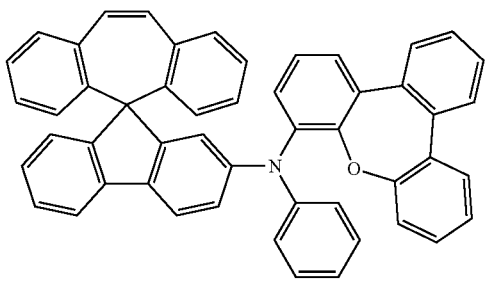
(56)
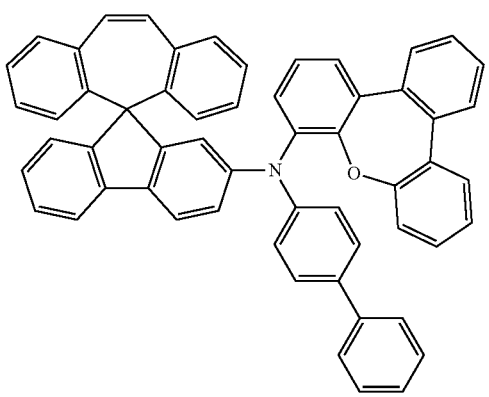
(58)
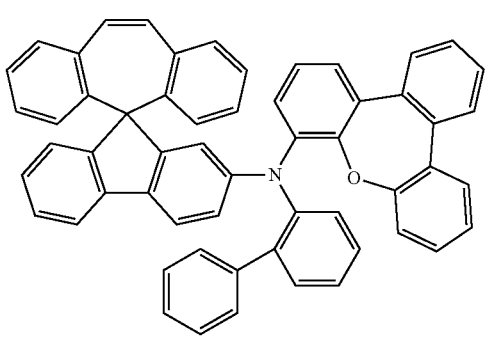
(59)
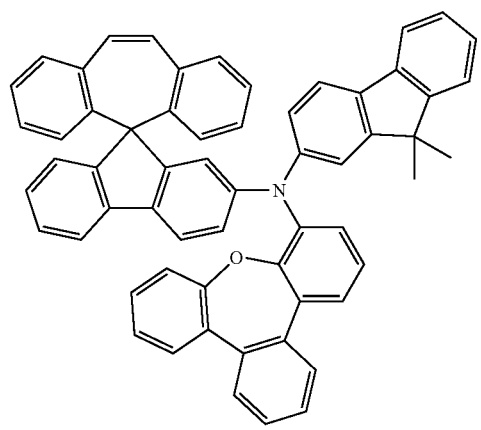
(61)
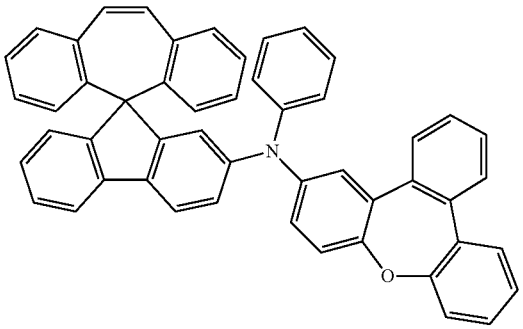
(62)
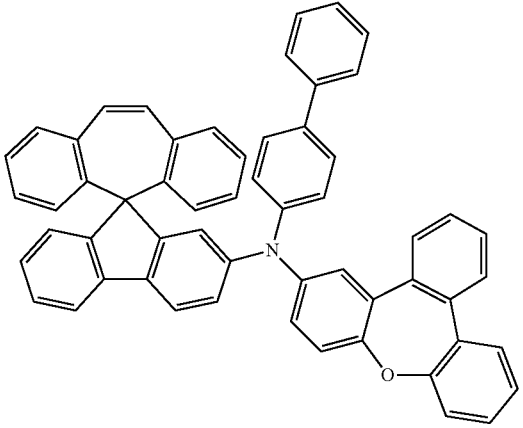
(64)
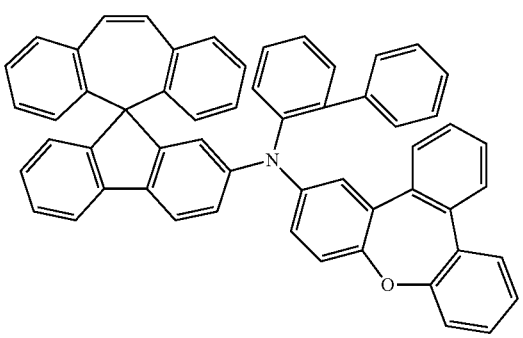

(65)
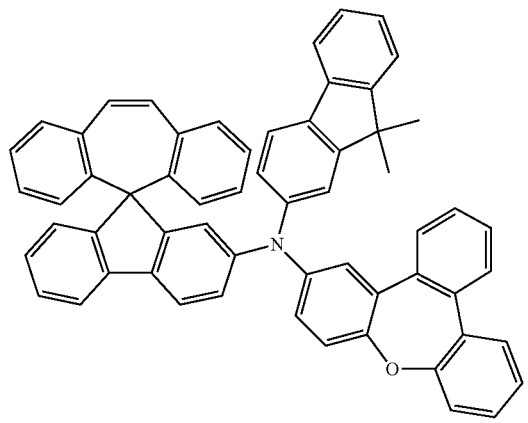
(67)
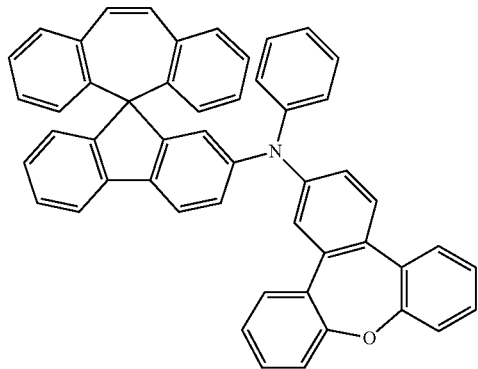
(68)
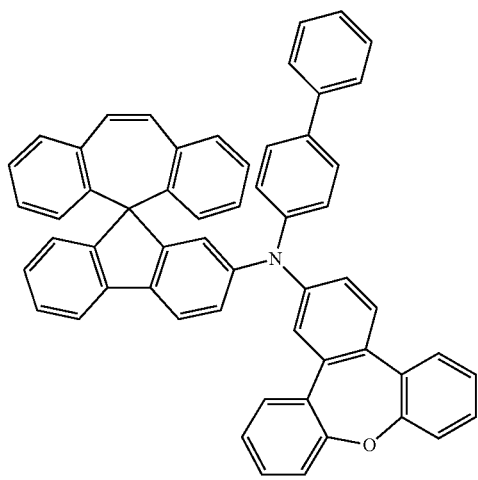
(70)
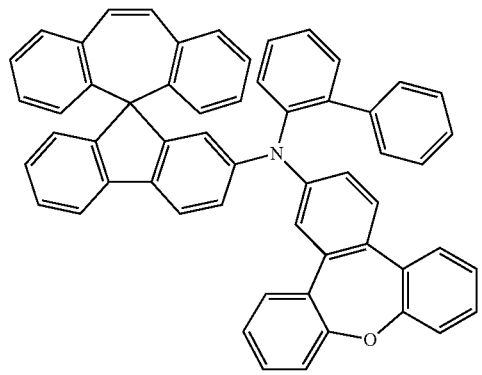
(71)
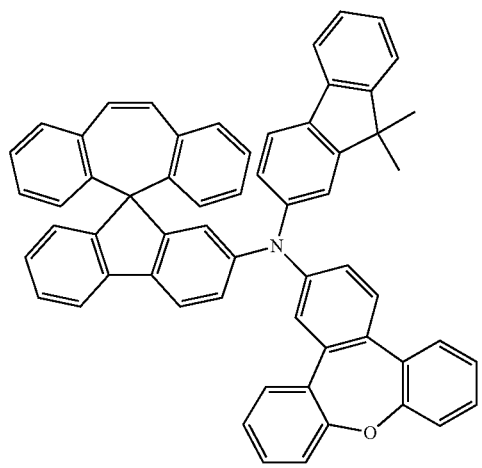
(79)
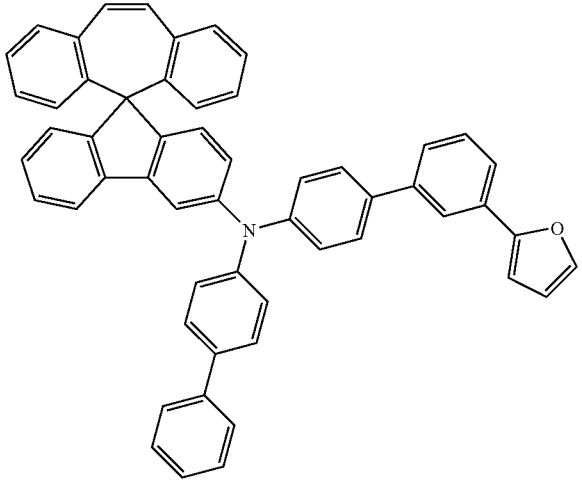

-continued
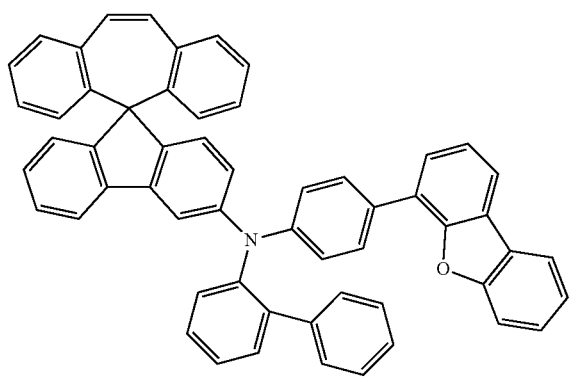
(85)
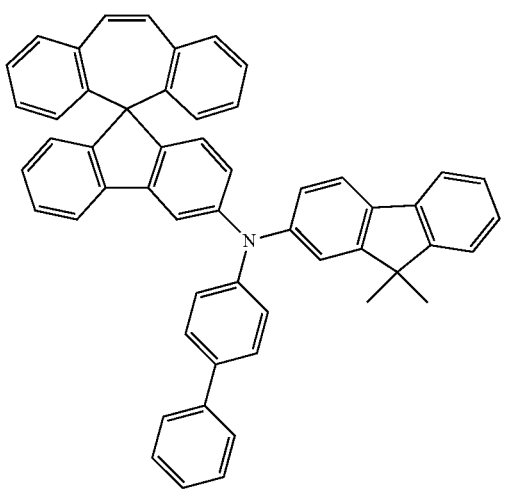
(86)
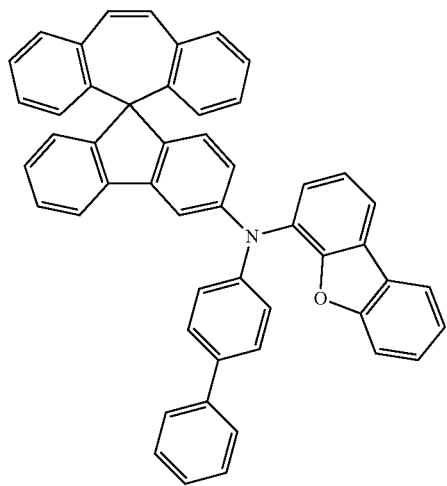
(88)
-continued
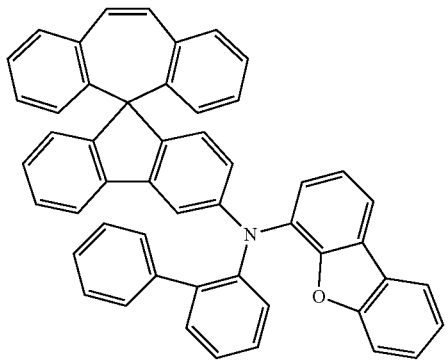
(90)
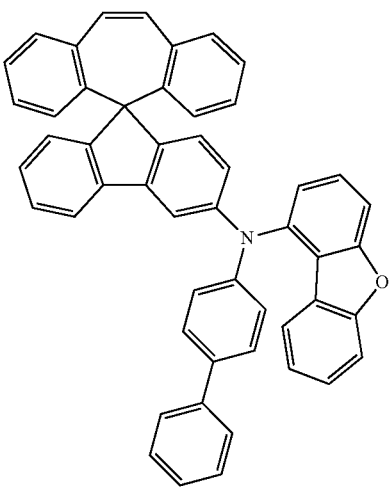
(91)
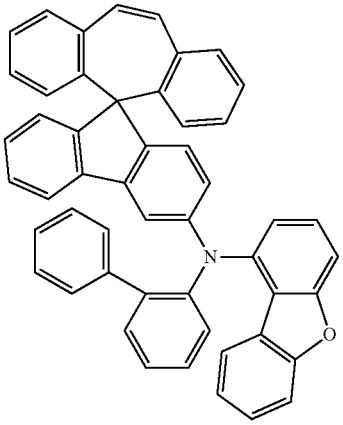
(93)

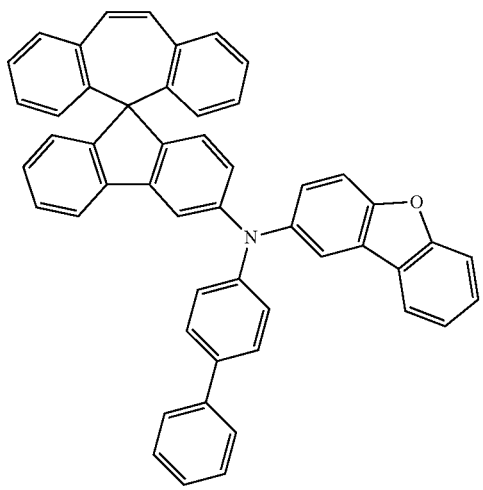
(94)
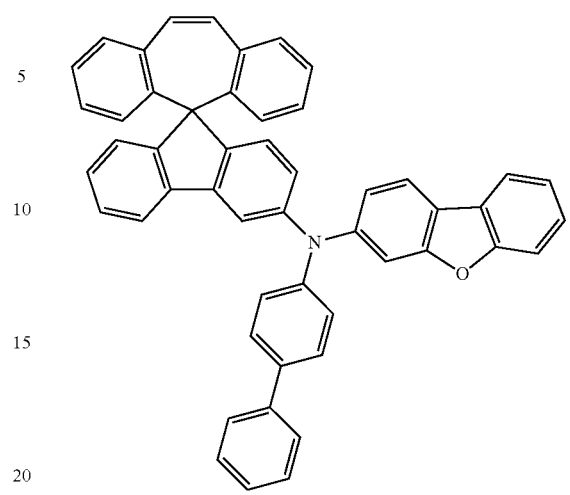
(99)
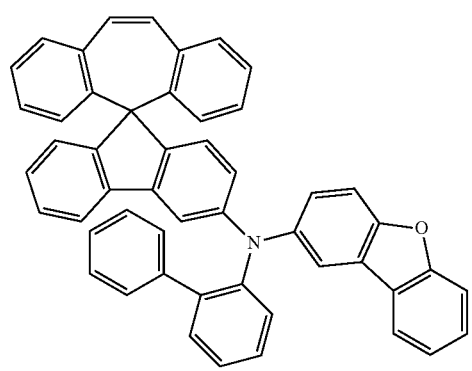
(96)
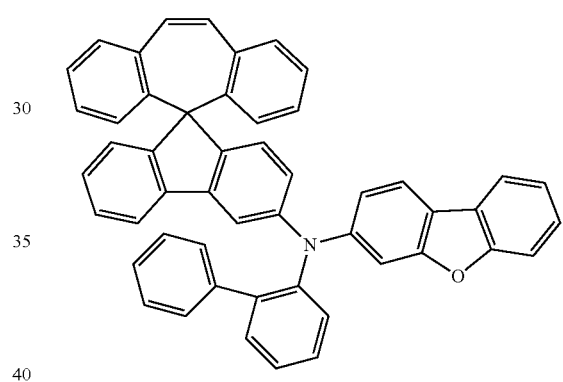
(101)
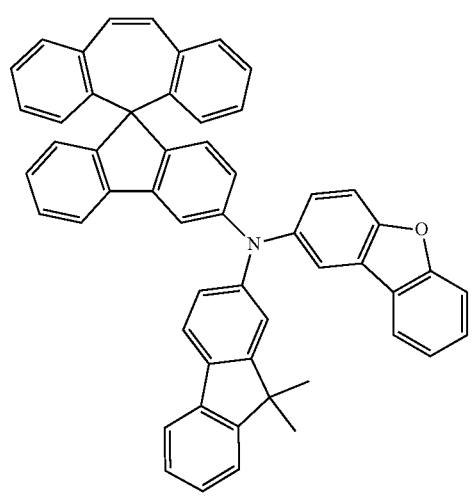
(97)
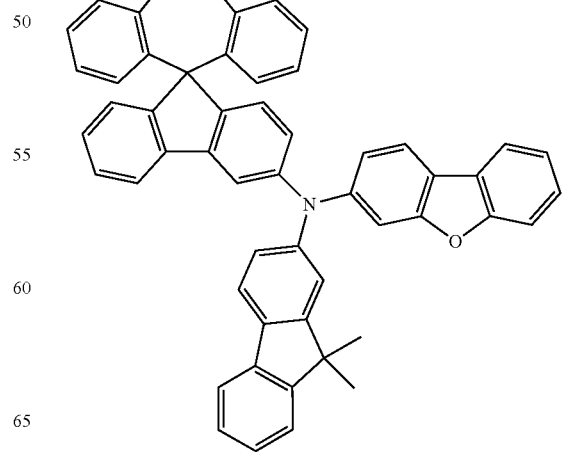
(102)

(104)
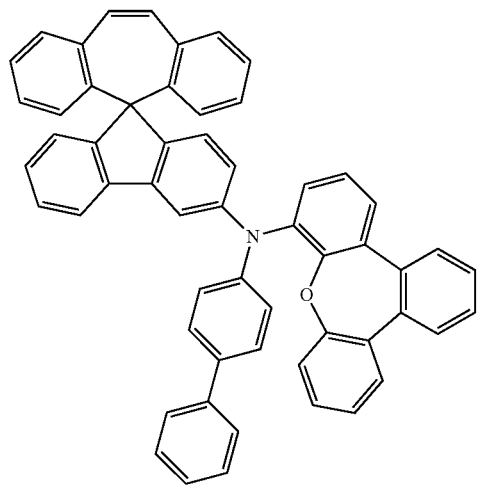
(110)
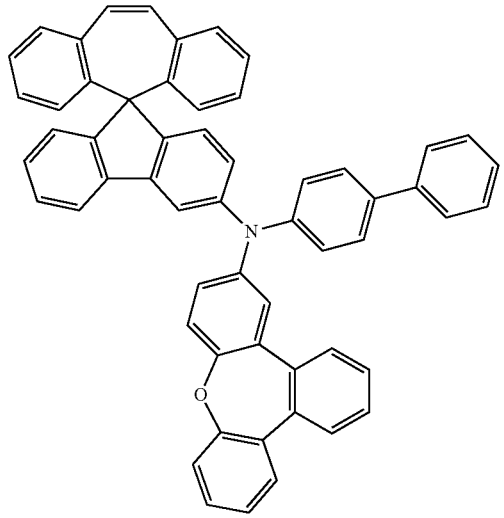
(106)
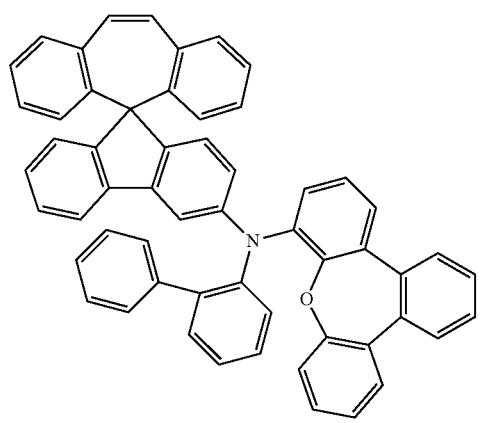
(112)
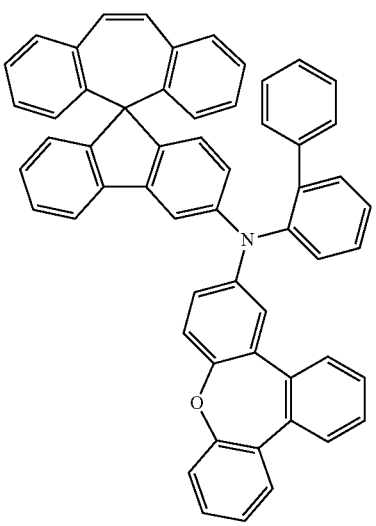
(109)
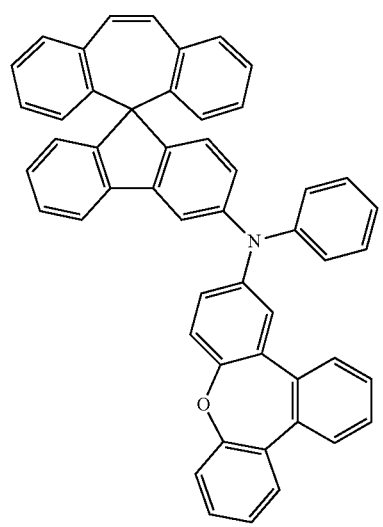
(113)
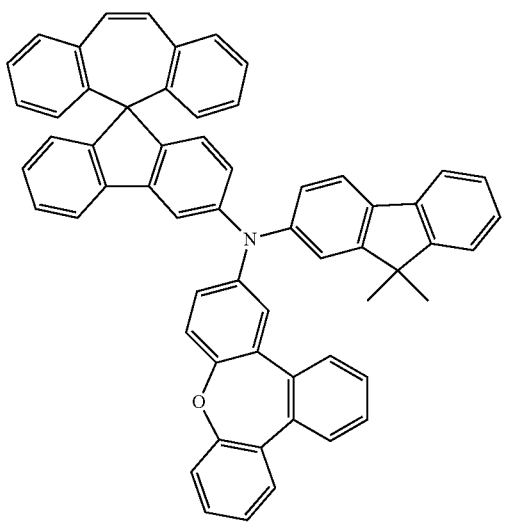

-continued
(115)
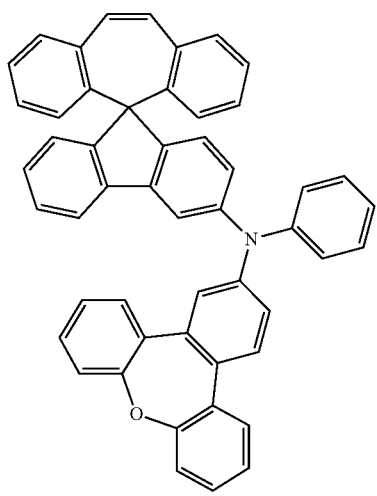
(116)
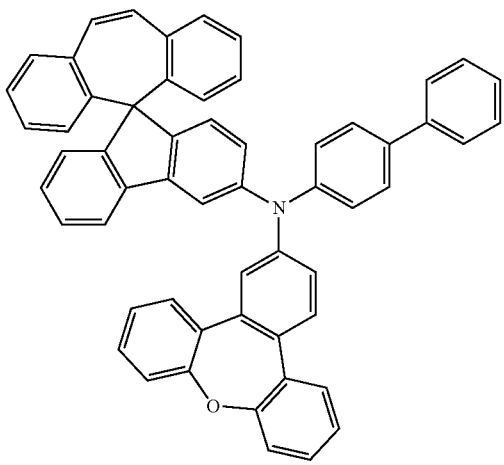
(118)
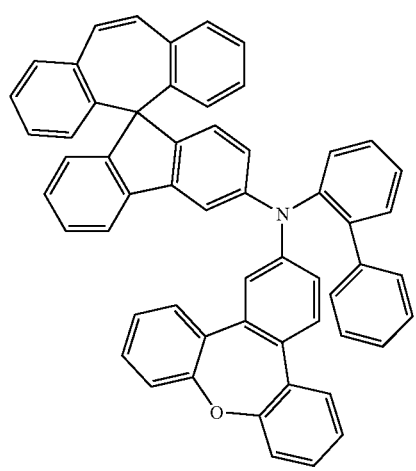
-continued
(119)
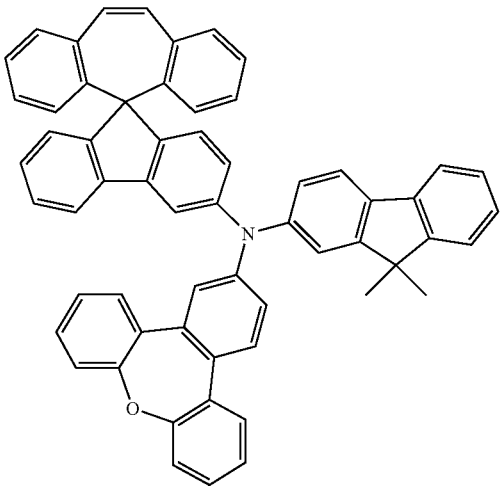
(126)
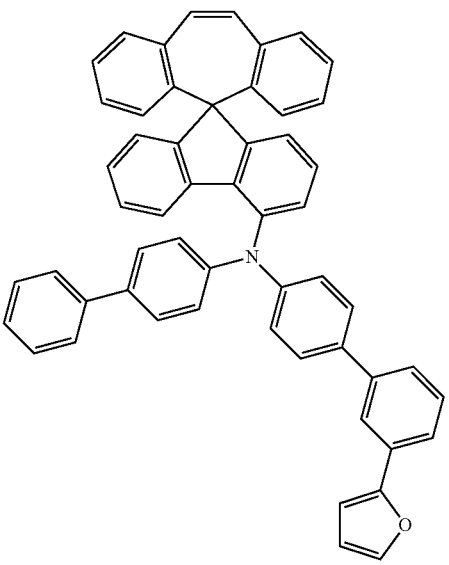
(132)
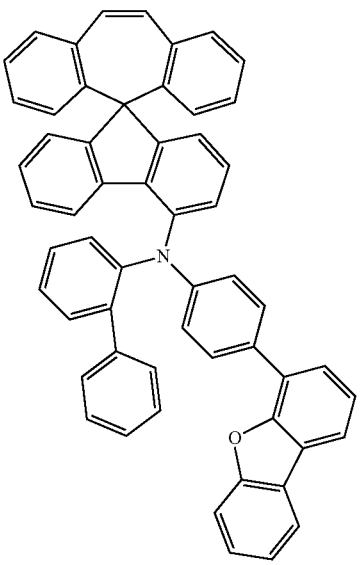

(133)
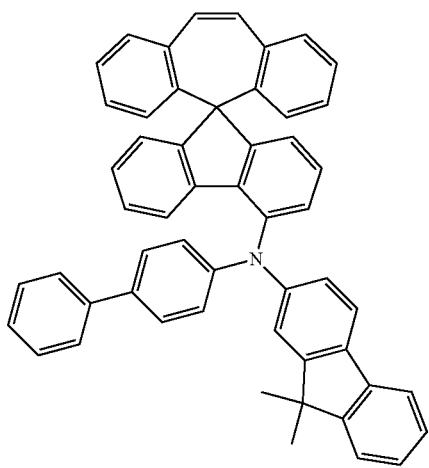
(138)
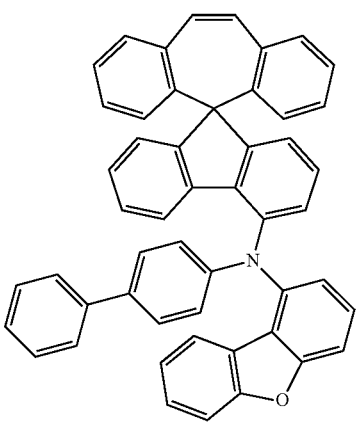
(136)
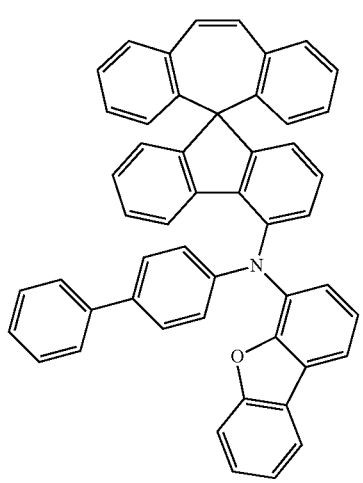
(140)
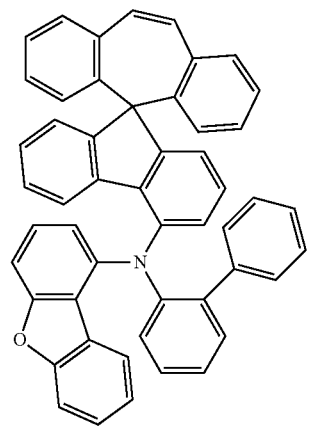
(137)
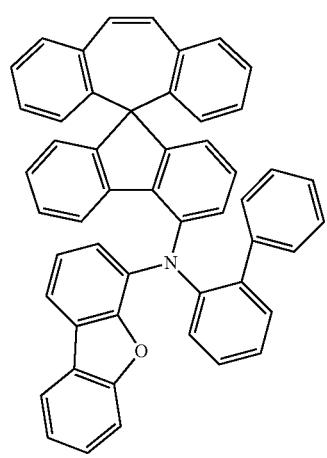
(141)
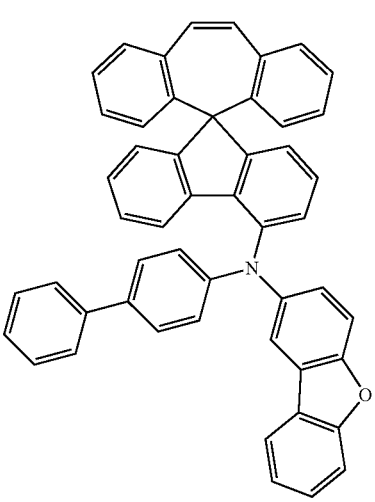

(143)
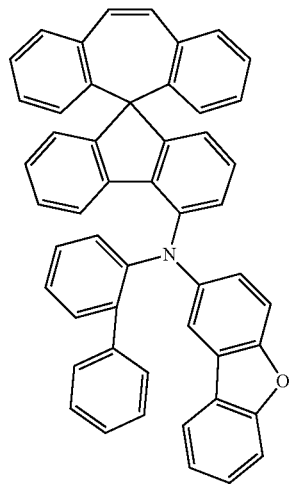
(148)
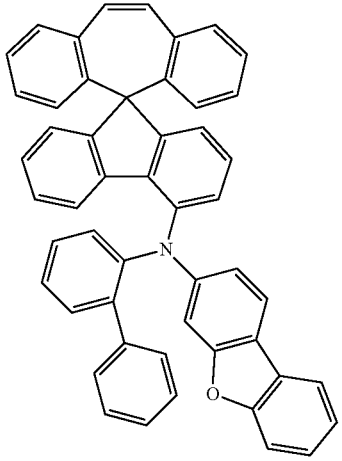
(144)
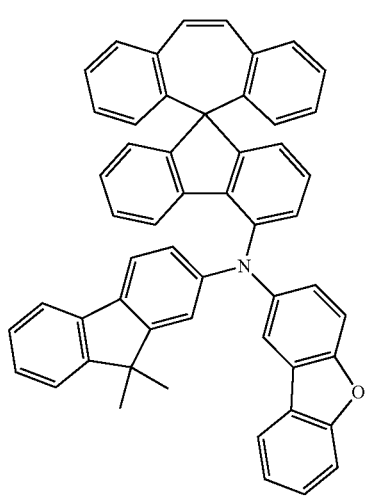
(149)
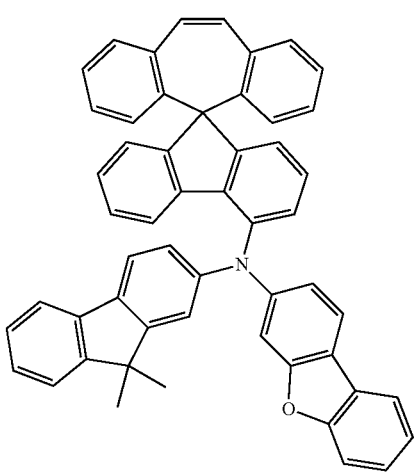
(146)
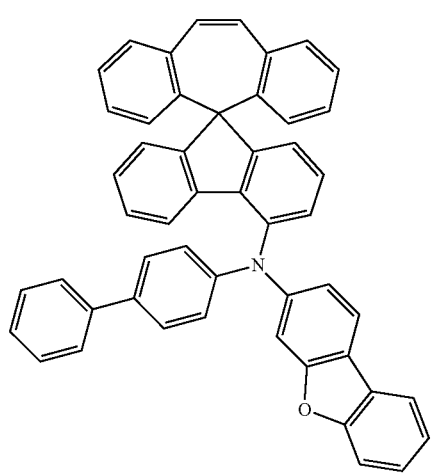
(151)
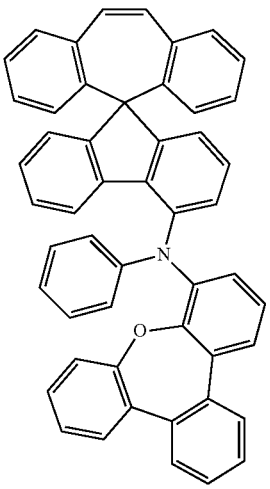

(152)
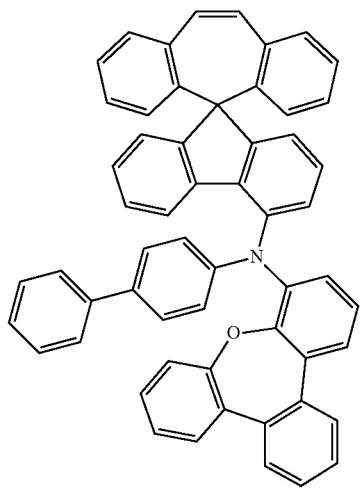
(154)
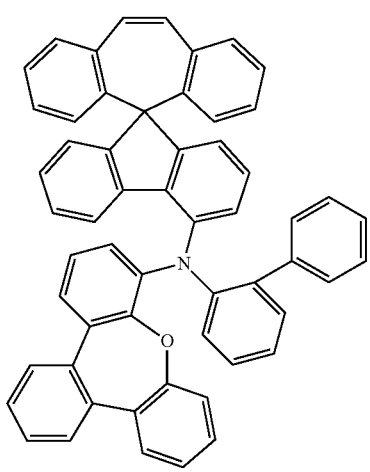
(155)
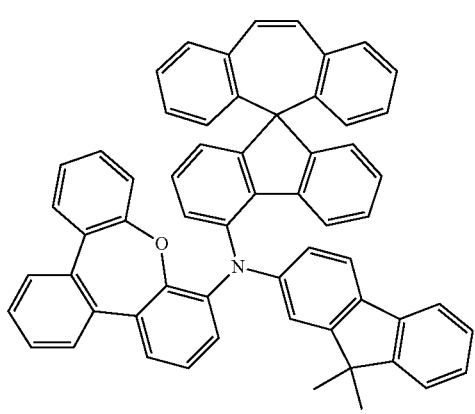
(157)
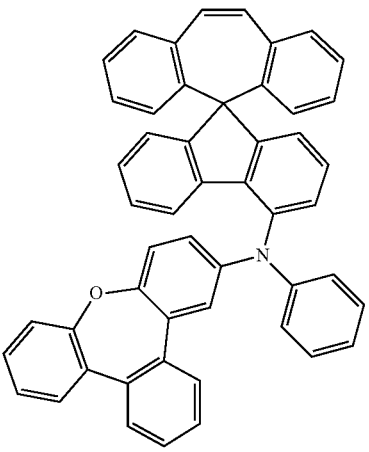
(158)
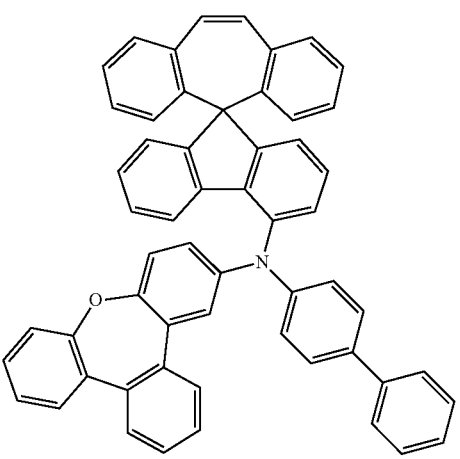
(160)
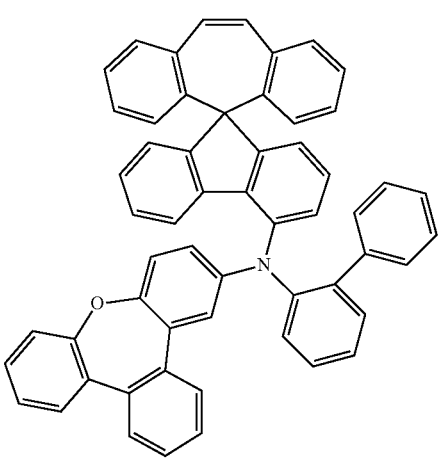

(161)
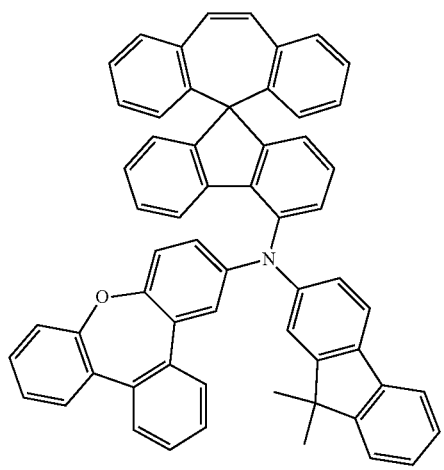
(166)
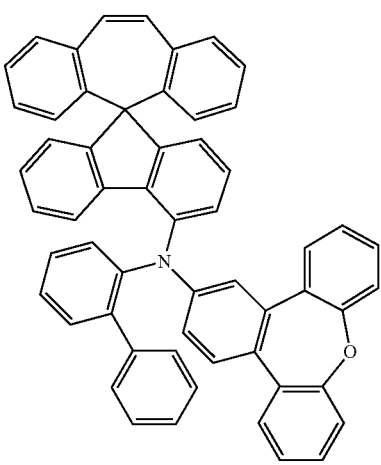
(163)
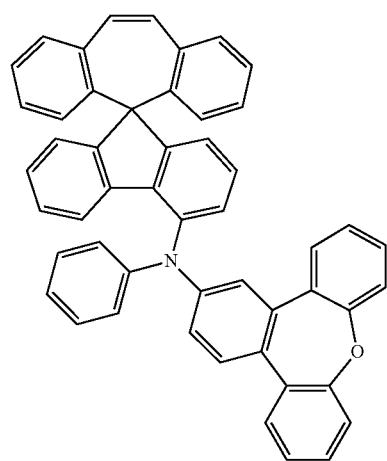
(167)
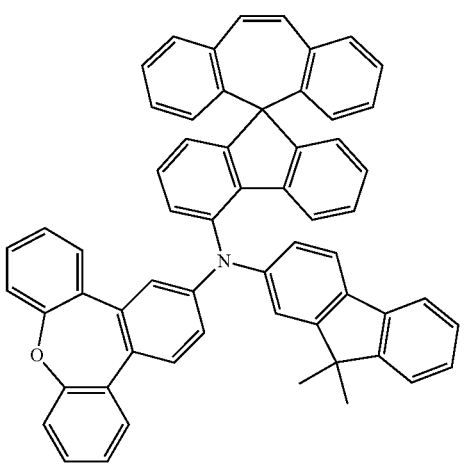
(164)
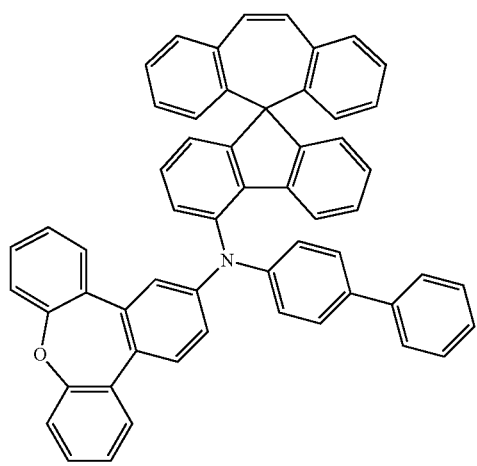
(169)
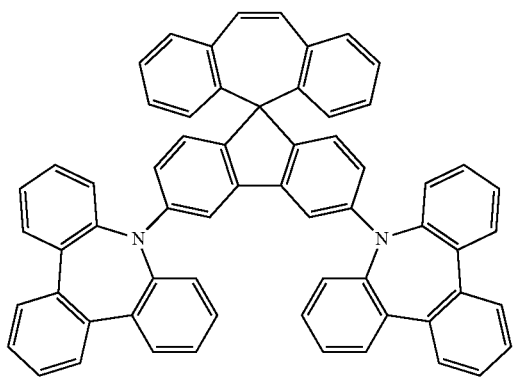

147
-continued
(174)
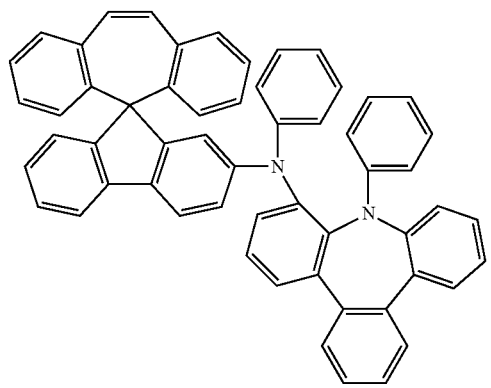
(175)
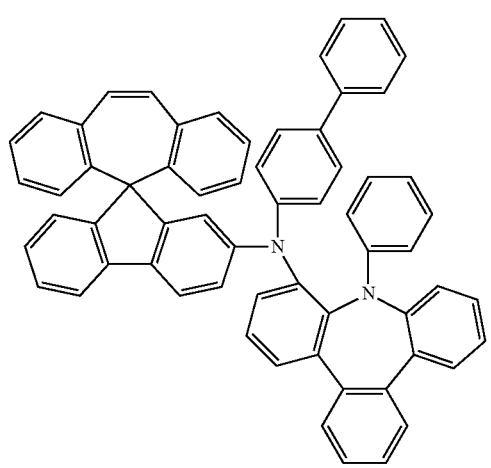
(176)
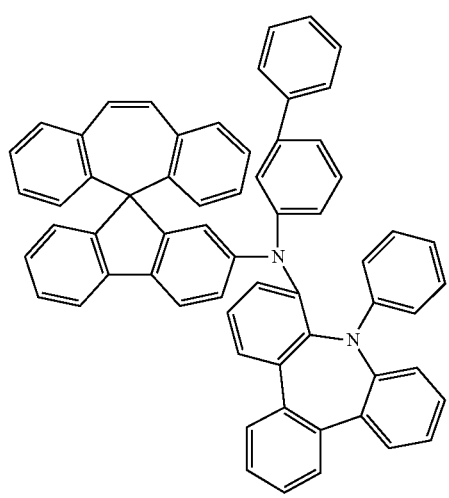
148
-continued
(177)
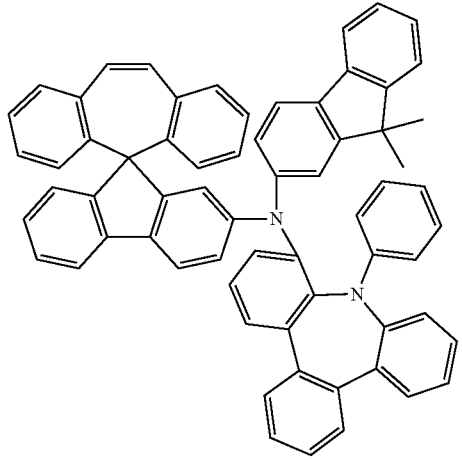
(178)
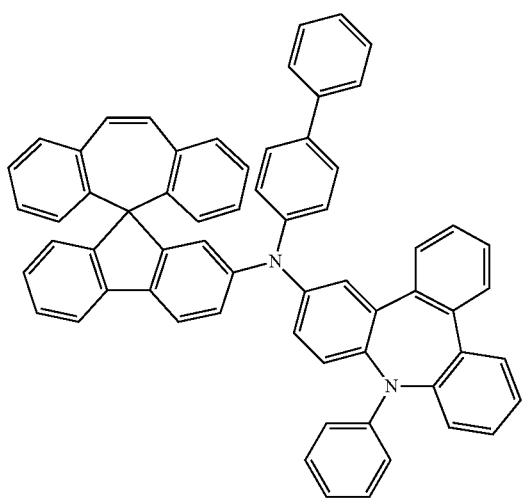
(179)

(180)
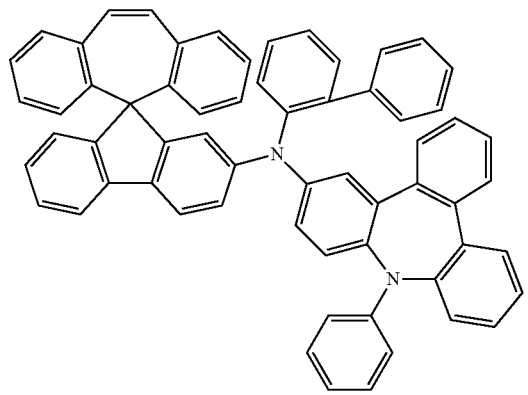
(181)
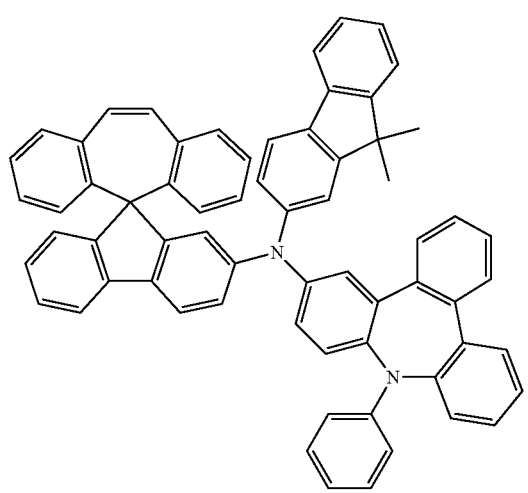
(182)
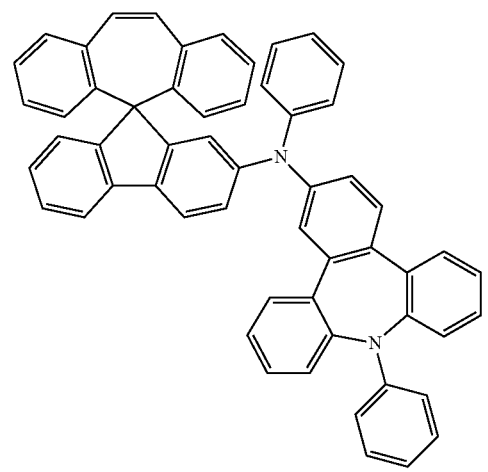
(183)
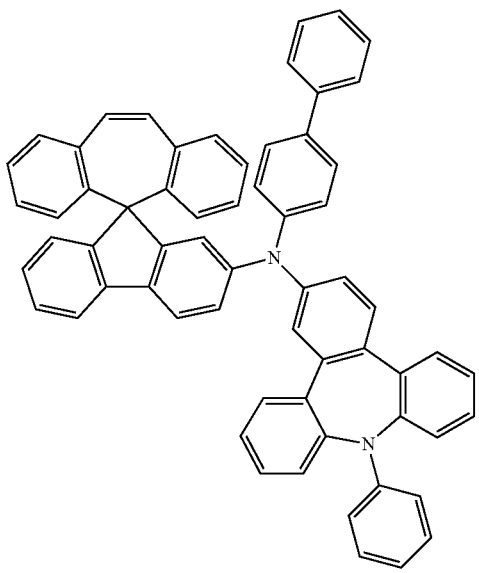
(184)
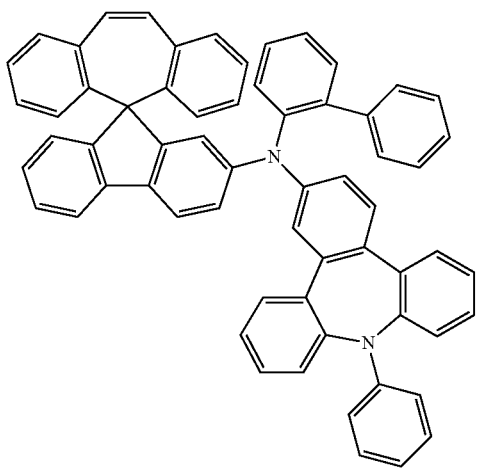
(185)
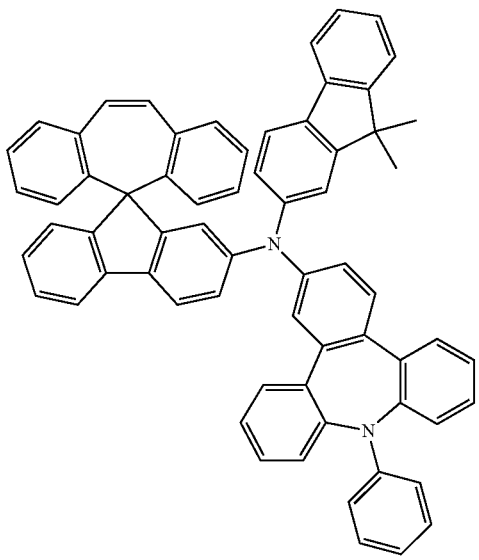

(186)
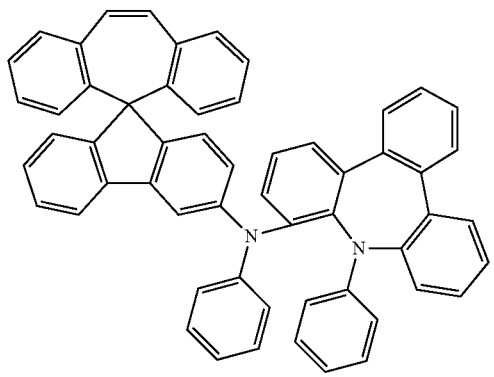
(187)
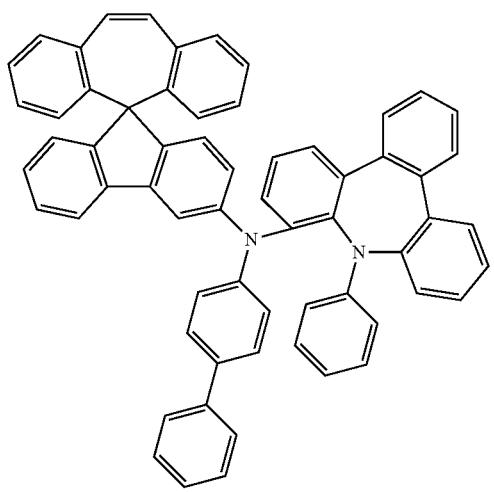
(189)
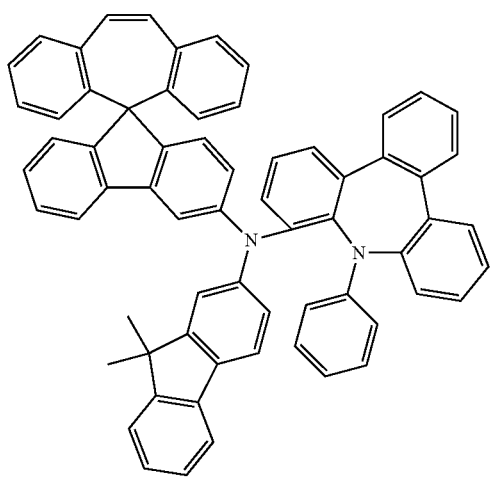
(190)
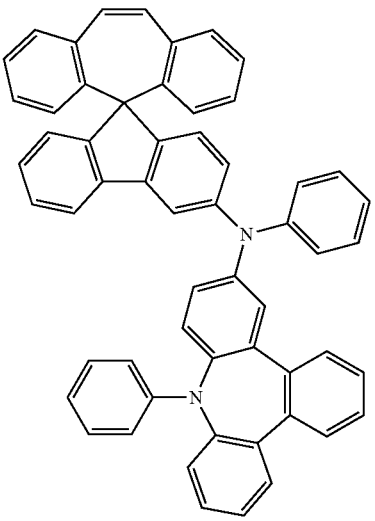
(191)
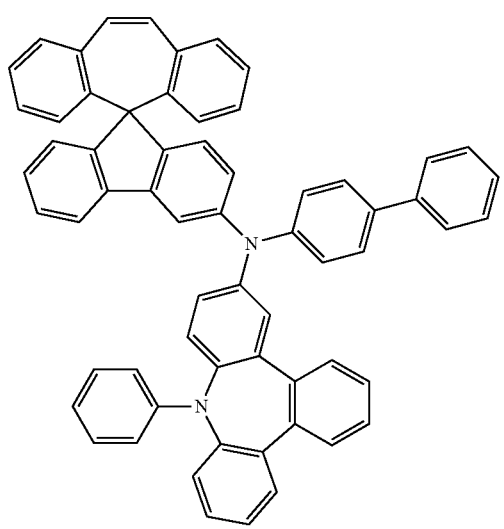
(192)
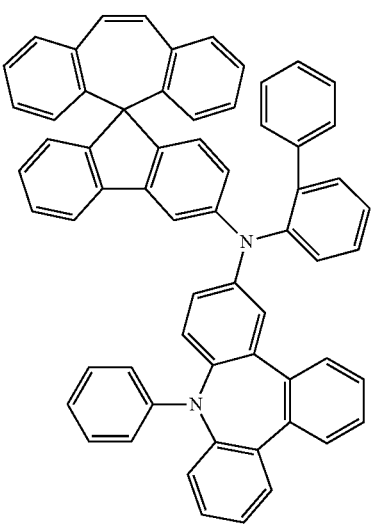

(193)
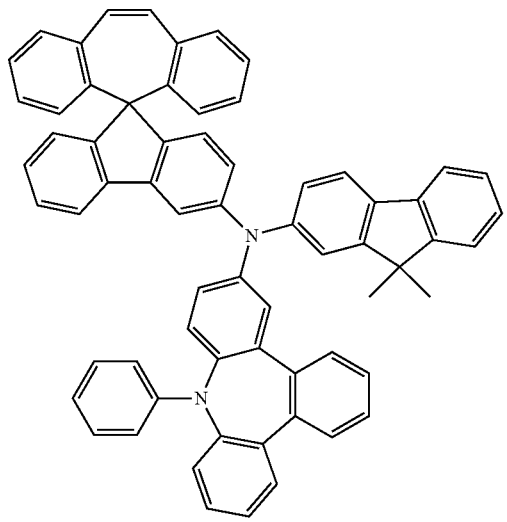
(194)
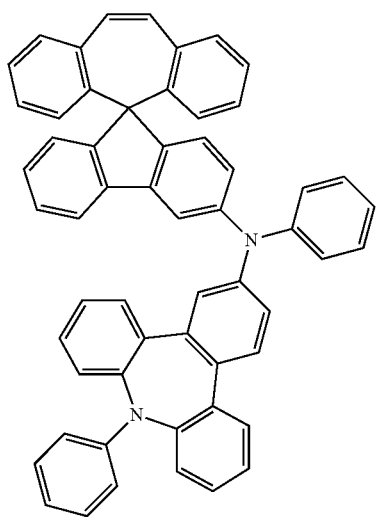
(195)
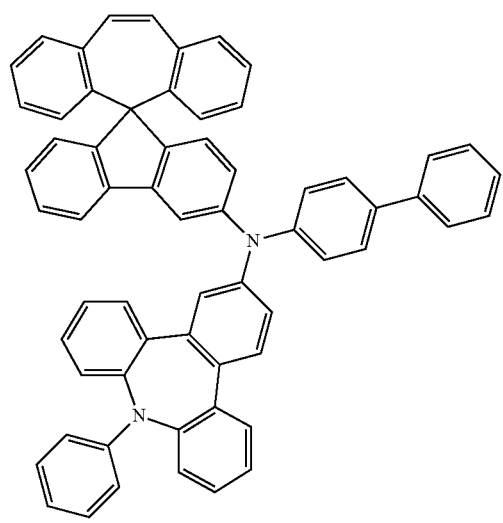
(196)
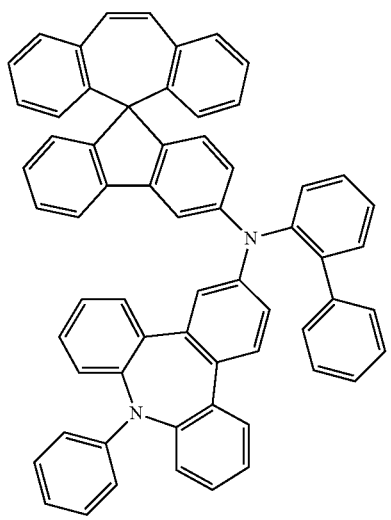
(197)
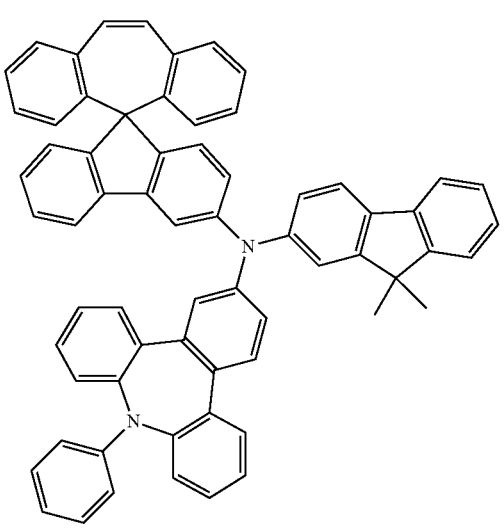
(198)
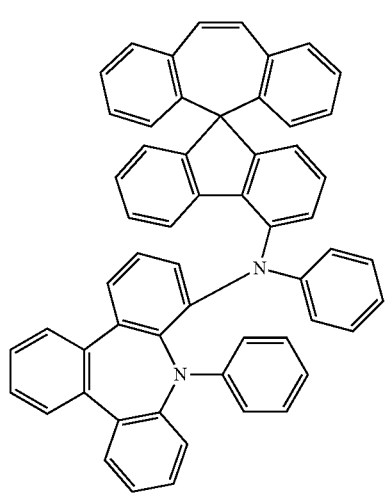

(199)
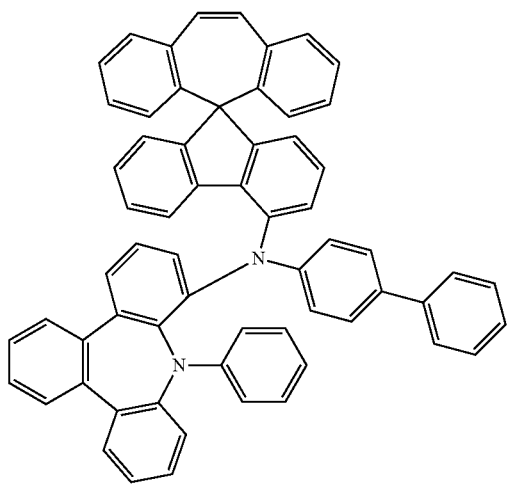
(201)
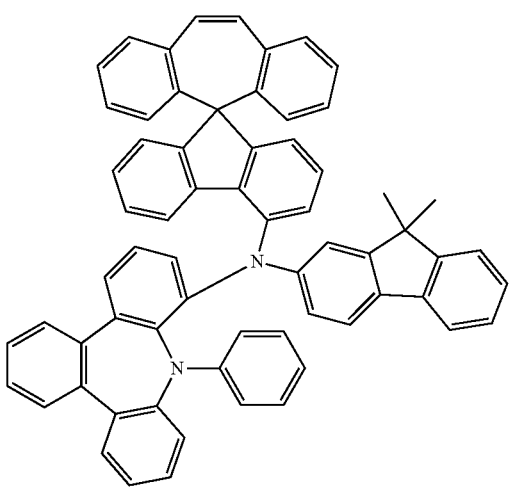
(202)
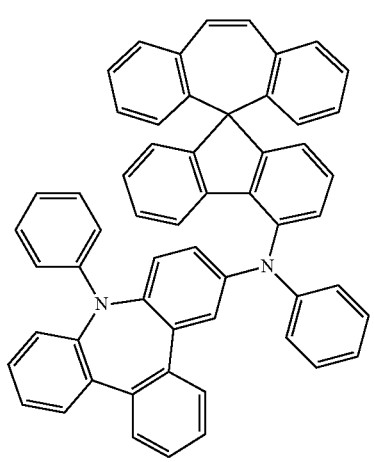
(203)
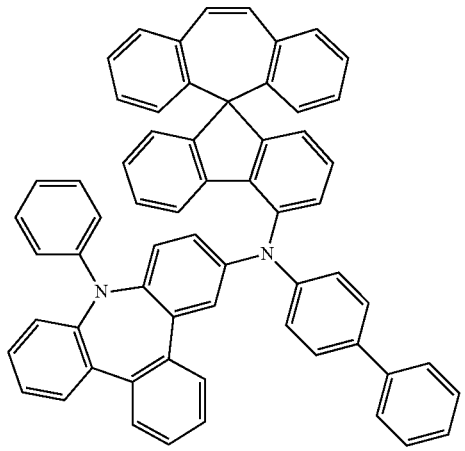
(204)
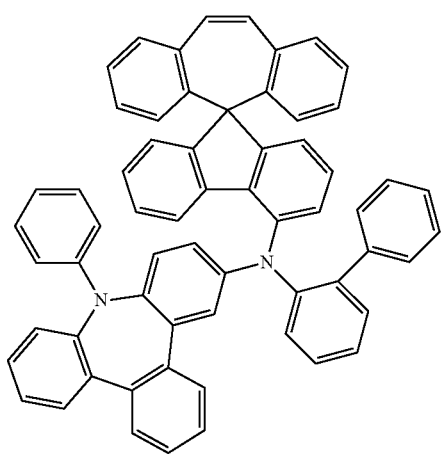
(205)
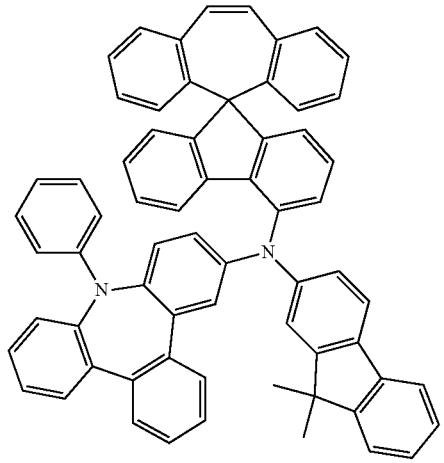

-continued (206)

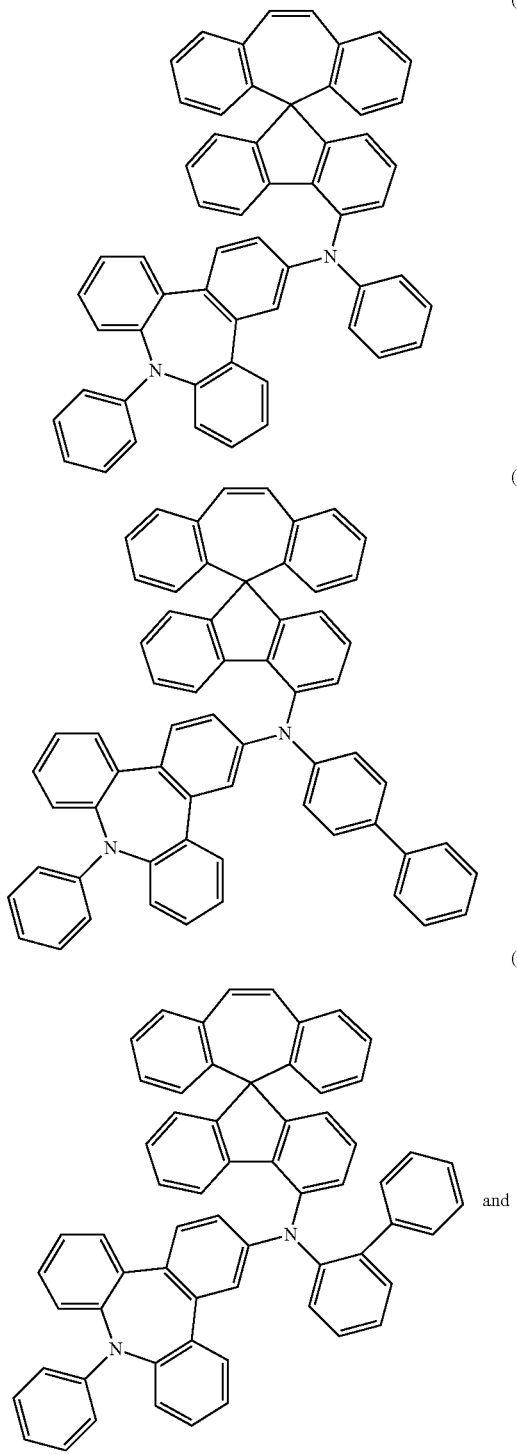

(207)

(208)

-continued (209)

7. An organic electronic device, comprising:
a first electrode;
a second electrode; and
an organic layer disposed between the first electrode and the second electrode, wherein the organic layer comprises the compound of claim 1.

8. The organic electronic device of claim 7, wherein the organic electronic device is an organic light emitting device.

9. The organic electronic device of claim 8, wherein the organic layer includes a hole transporting layer; and the hole transporting layer comprises the compound of claim 1.

10. The organic electronic device of claim 8, wherein the organic layer includes a hole injection layer; and the hole injection layer comprises the compound of claim 1.

11. The organic electronic device of claim 8, wherein the organic layer includes an electron blocking layer; and the electron blocking layer comprises the compound of claim 1.

* * * * *